(12) United States Patent
Byun et al.

(10) Patent No.: US 9,780,314 B2
(45) Date of Patent: Oct. 3, 2017

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si, Chungcheongnam-do (KR)

(72) Inventors: Jihun Byun, Cheonan-si (KR); Yeonhee Choi, Cheonan-si (KR); Kayoung Eom, Icheon-si (KR); Hyeryeong Kim, Cheonan-si (KR); Yuri Kim, Wonju-si (KR); Junghwan Park, Seoul (KR); Hakyoung Lee, Incheon (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 118 days.

(21) Appl. No.: 14/772,613

(22) PCT Filed: Feb. 27, 2014

(86) PCT No.: PCT/KR2014/001635
§ 371 (c)(1),
(2) Date: Sep. 3, 2015

(87) PCT Pub. No.: WO2014/137104
PCT Pub. Date: Sep. 12, 2014

(65) Prior Publication Data
US 2016/0020408 A1    Jan. 21, 2016

(30) Foreign Application Priority Data

Mar. 7, 2013  (KR) .......................... 10-2013-0024669

(51) Int. Cl.
*H01L 51/00* (2006.01)
*C07D 471/04* (2006.01)
*C07D 487/04* (2006.01)
*C09K 11/06* (2006.01)
*H01L 51/50* (2006.01)

(52) U.S. Cl.
CPC ........ *H01L 51/0072* (2013.01); *C07D 471/04* (2013.01); *C07D 487/04* (2013.01); *C09K 11/06* (2013.01); *H01L 51/006* (2013.01); *H01L 51/0052* (2013.01); *H01L 51/0058* (2013.01); *H01L 51/0059* (2013.01); *H01L 51/0061* (2013.01); *H01L 51/0067* (2013.01); *H01L 51/0071* (2013.01); *H01L 51/0073* (2013.01); *H01L 51/0074* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *H01L 51/5016* (2013.01); *H01L 51/5056* (2013.01); *H01L 51/5072* (2013.01); *H01L 51/5088* (2013.01); *H01L 51/5092* (2013.01); *Y02E 10/549* (2013.01)

(58) Field of Classification Search
None
See application file for complete search history.

(56) References Cited

FOREIGN PATENT DOCUMENTS

| | | | |
|---|---|---|---|
| KR | 10-2008-0109000 | A | 12/2008 |
| KR | 10-2010-0012781 | A | 2/2010 |
| KR | 10-2010-0027950 | A | 3/2010 |
| KR | 10-2011-0049665 | A | 5/2011 |
| KR | 10-2011-0058250 | A | 6/2011 |

*Primary Examiner* — J. L. Yang
(74) *Attorney, Agent, or Firm* — Vorys, Sater, Seymour & Pease LLP; Mih Suhn Koh

(57) ABSTRACT

The present invention provides a novel compound capable of improving light emitting efficiency, stability, and lifespan of the element, an organic element using the same, and an electric device for the same.

9 Claims, 1 Drawing Sheet

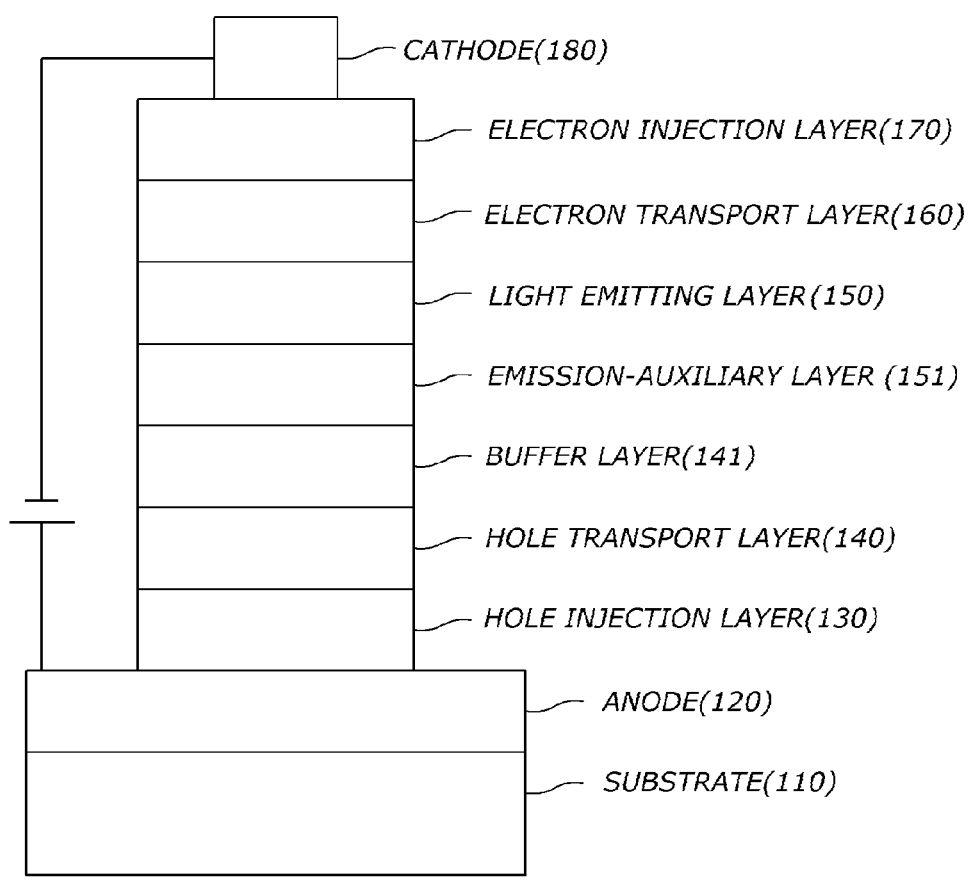

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This application is a National Phase Application filed under 35 U.S.C. §371 as a national stage of PCT/KR2014/001635, filed on Feb. 27, 2014, an application claiming priority from and the benefit under 35 U.S.C. §119(a) of Korean Patent Application No. 10-2013-0024669, filed on Mar. 7, 2013, the contents of which are hereby incorporated by reference for all purposes as if fully set forth herein.

BACKGROUND

Technical Field

The present invention relates to compounds for organic electric elements, organic electric elements using the same, and electronic devices thereof.

Background Art

In general, an organic emitting phenomenon refers to a phenomenon in which electric energy is converted into light energy of an organic material. An organic electric element utilizing the organic emitting phenomenon usually has a structure including an anode, a cathode, and an organic material layer interposed therebetween. In many cases, the organic material layer has a multi-layered structure including multiple layers made of different materials in order to improve the efficiency and stability of an organic electric element, and for example, may include a hole injection layer, a hole transport layer, a light emitting layer, an electron transport layer, an electron injection layer, or the like.

A material used as an organic material layer in an organic electric element may be classified into a light emitting material and a charge transport material, for example, a hole injection material, a hole transport material, an electron transport material, an electron injection material, and the like according to its function.

In addition, it is required to develop a hole injection layer material that retards penetration/diffusion of metal oxides from an anode electrode (ITO) into an organic layer, which is one cause for the shortened life span of an organic electric element, and has stability against Joule heat generated during the operation of an organic electric element, that is, a high glass transition temperature.

Also, it has been reported that a low glass transition temperature of a hole transport layer material has a great effect on the lifespan of an organic electric element because the uniformity of a thin film surface is broken during the operation of the element. In general, deposition is a main method of forming an OLED, and thus there is an actual need to develop a material that is durable to such a deposition method, that is, a highly heat-resistant material.

In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed. Accordingly, there is a continuous need to develop new materials for an organic material layer.

SUMMARY

In order to solve one or more of the above-mentioned problems in prior art, an aspect of the present invention is to provide a compound which allows an organic electric element to have high luminous efficiency, low driving voltage and high heat-resistant and to be improved in color purity and life span, an organic electric element using the same, and an electronic device including the organic electric element.

In accordance with an aspect of the present invention, a compound represented by the following formula 1 is provided:

[Formula 1]

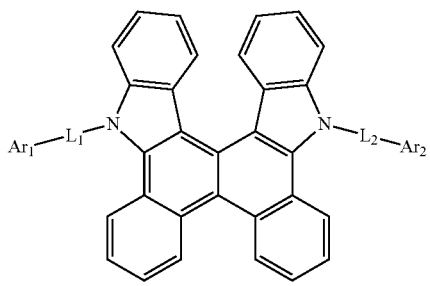

In accordance with another aspect of the present invention, an organic electric elements comprising the compound represented by the formula 1 above and electronic devices comprising the organic electric element are provided.

By using the compound according to embodiments of the present invention, an organic electric element according to one or more embodiments of the present invention not only has high luminous efficiency, low driving voltage and high heat-resistant and, but can also be significantly improved in color purity, luminous efficiency, and life span.

BRIEF DESCRIPTION OF THE DRAWINGS

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

Unless otherwise stated, the term "halo" or "halogen" as used herein includes fluorine, chlorine, bromine, or iodine.

Unless otherwise stated, the term "alkyl" or "alkyl group" as used herein has, but not limited to, a single bond of 1 to 60 carbon atoms.

Unless otherwise stated, the term "alkenyl" or "alkynyl" as used herein has, but not limited to, double or triple bonds of 2 to 60 carbon atoms.

Unless otherwise stated, the term "cycloalkyl" as used herein means, but not limited to, alkyl forming a ring having 3 to 60 carbon atoms.

Unless otherwise stated, the term "alkoxyl group" as used herein has, but not limited to, and has 1 to 60 carbon atoms.

Unless otherwise stated, the term "aryl group" or "arylene group" as used herein has, but not limited to, 6 to 60 carbon atoms.

Herein, the aryl group or arylene group means a monocyclic or polycyclic aromatic group, and may also be formed in conjunction with an adjacent group. Examples of "aryl group" or "arylene group" may include a phenyl group, a biphenyl group, a fluorene group, or a spirofluorene group.

Unless otherwise stated, the term "heteroalkyl" as used herein means alkyl containing one or more heteroatoms. Unless otherwise stated, the term "heteroaryl group" or "heteroarylene group" as used herein means, but not limited to, an aryl or an arylene group having 2 to 60 carbon atoms and containing one or more heteroatoms, includes both monocyclic and polycyclic rings, and may also be formed in conjunction with an adjacent group.

Unless otherwise stated, the term "Heterocycloalkyl", "heterocyclic group" as used herein contains one or more heteroatoms, has 2 to 60 carbon atoms, includes both monocyclic and polycyclic rings, and may be formed in conjunction with an adjacent group. Also, the heterocyclic group may mean alicyclic and/or aromatic group containing heteroatoms.

Unless otherwise stated, the term "heteroatom" as used herein represents at least one of N, O, S, P, and Si.

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "ring" means an aliphatic ring having 3 to 60 carbon atoms, an aromatic ring having 6 to 60 carbon atoms, a hetero ring having 2 to 60 carbon atoms, or a fused ring formed by the combination of them, and includes a saturated or unsaturated ring.

Hetero compounds other than the above-mentioned hetero compounds or hetero radicals each contain, but not limited to, one or more heteroatoms.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer between the first electrode 120 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further comprise at least one protective layer formed on at least one of the sides of the first and second electrodes, which is a side opposite to the organic material layer.

The organic electric element according to an embodiment of the present invention may be manufactured using a PVD (physical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

Further, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

The compound according to an aspect of the present invention is represented by Formula 1 below:

[Formula 1]

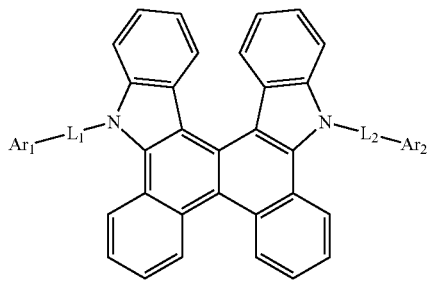

In Formula 1 above, $Ar_1$ and $Ar_2$ may be independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, a $C_6$-$C_{60}$ aryloxy group, $C_3$-$C_{60}$ cycloalkyl group, and —N(R')(R"). Herein, R' and R" can be independently selected from the group consisting of a $C_6$-$C_{60}$ aryl group, a fluorenyl group, and a $C_2$-$C_{60}$ heterocyclic group containing at least one heteroatom selected from the group consisting of O, N, S, Si, and P.

$L_1$ and $L_2$ may be independently selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, and a bivalent aliphatic hydrocarbon group. Herein, each of an arylene group, a fluorenylene group, a heterocyclic group, a fused ring group and an aliphatic hydrocarbon group may be optionally substituted by one or more substituents selected from the group consisting of a nitro group, a nitrile group, halogen group, a $C_1$-$C_{20}$ alkyl group, a $C_6$-$C_{20}$ aryl group, a $C_2$-$C_{20}$ heterocyclic group, a $C_1$-$C_{20}$ alkoxy group, and amino group.

Specifically, the compound represented by Formula 1 above may be represented by one of the following Formulas:

[Formula 2]

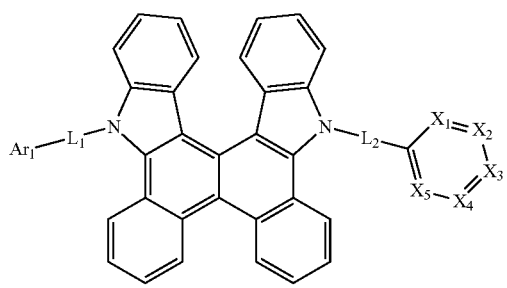

[Formula 3]

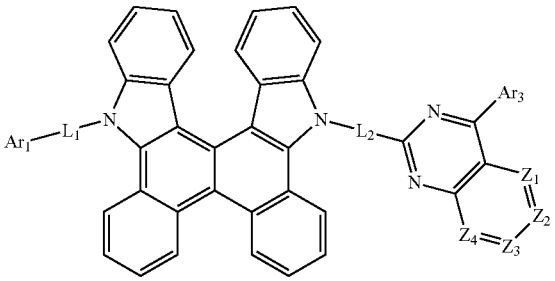

[Formula 4]

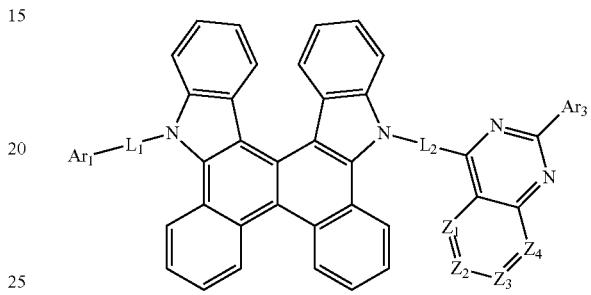

In Formula 2 to 4, $Ar_1$, $L_1$ and $L_2$ are as defined in Formula 1 above.

In addition, $Ar_3$ may be selected from the group consisting of a $C_6$-$C_{60}$ aryl group, a $C_2$-$C_{20}$ alkenyl group, a $C_2$-$C_{60}$ heterocyclic group containing at least one heteroatom selected from the group consisting of O, N, S, Si, and P, a $C_1$-$C_{50}$ alkyl group, and a fluorenyl group.

$X_1$ to $X_5$ and $Z_1$ to $Z_4$ are independently $CR_1$ or N. Herein, $R_1$ may be selected from the group consisting of a hydrogen, a $C_6$-$C_{60}$ aryl group, a fluorenyl group, and $C_2$-$C_{60}$ heterocyclic group containing at least one heteroatom selected from the group consisting of O, N, S, Si, and P.

Meanwhile, $Ar_1$ to $Ar_3$, R', R" and $R_1$ can be substituted by other substituents.

That is, an aryl group, a fluorenyl group, a heterocyclic group, an alkyl group, a cycloalkyl group, an alkenyl group, an aryloxy group and an alkoxy group may be respectively substituted by one or more substituents selected from the group consisting of deuterium, halogen, a silane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

Herein, in the case of an aryl group above, the aryl group may have 6 to 60 carbon atoms, preferably, 6 to 30 carbon atoms and more preferably, 6 to 20 carbon atoms, in the case of an heterocyclic group above, the heterocyclic group may have 2 to 60, preferably, 2 to 40 and more preferably, 2 to 30, in the case of an arylene group above, the arylene group may have 6 to 60 carbon atoms, preferably, 6 to 30 carbon atoms and more preferably, 6 to 20 carbon atoms, and in the case of an alkyl group above, the alkyle group may have 1 to 50 carbon atoms, preferably, 1 to 30 carbon atoms and more preferably, 1 to 20 carbon atoms, and much more preferably, 1 to 10 carbon atoms.

Specifically, the compound represented by Formula 1 above may be represented by one of the following compounds:

P-1
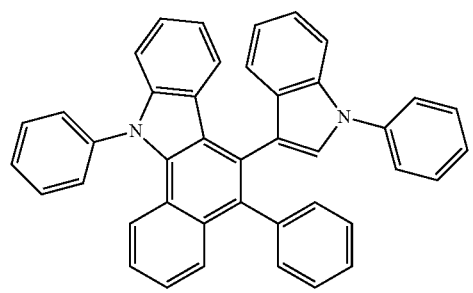
P-2
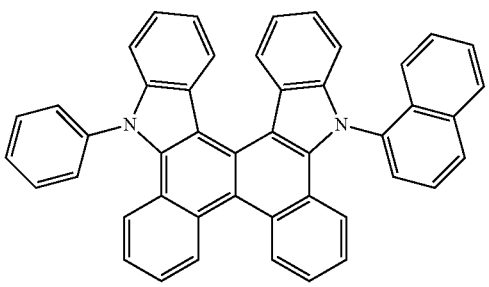
P-3
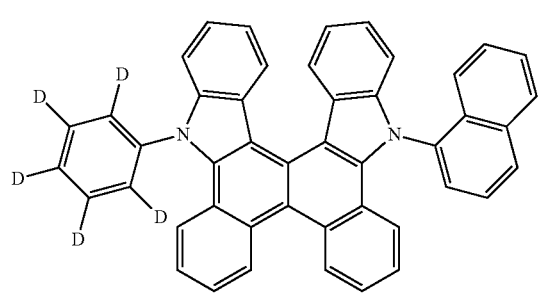
P-4
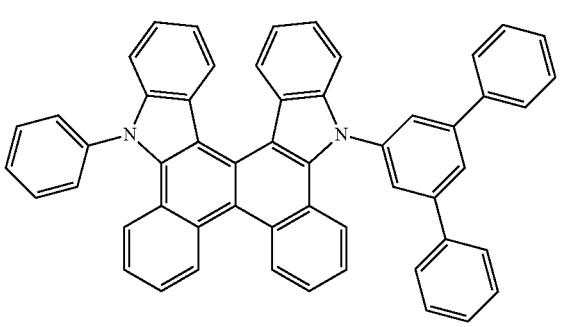
P-5
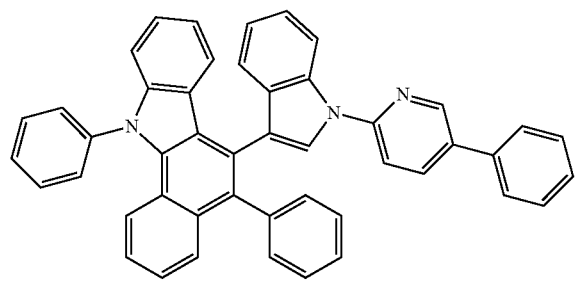
P-6
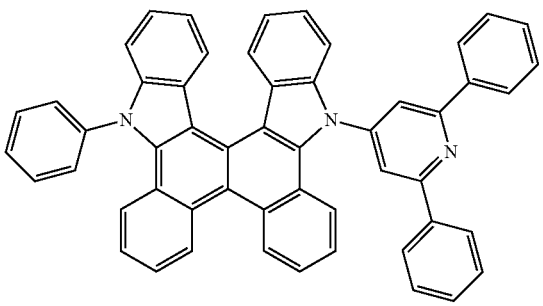
P-7
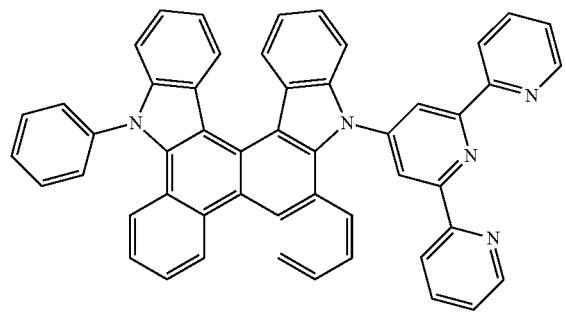
P-8
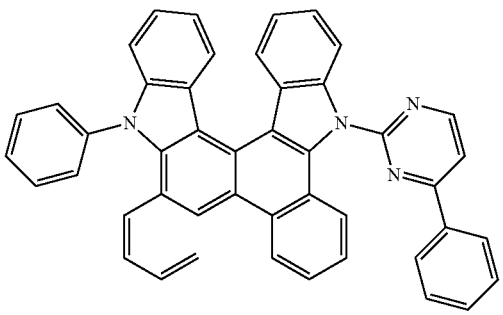
P-9
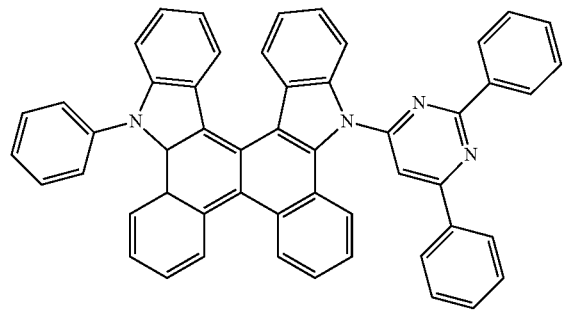
P-10
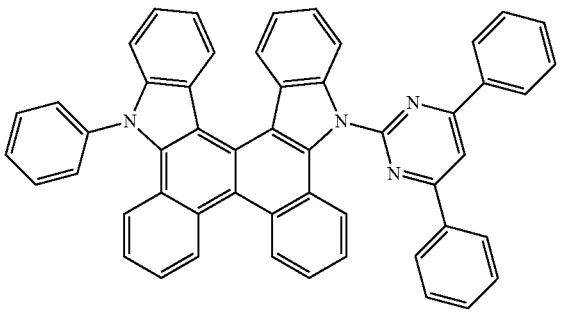

-continued
P-11
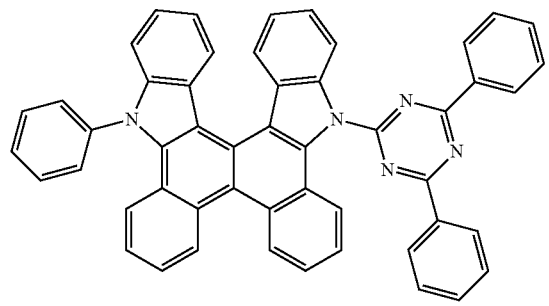
P-12
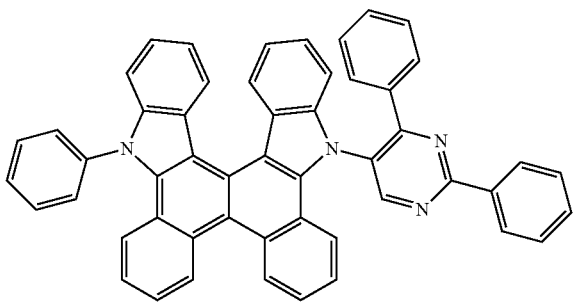
P-13
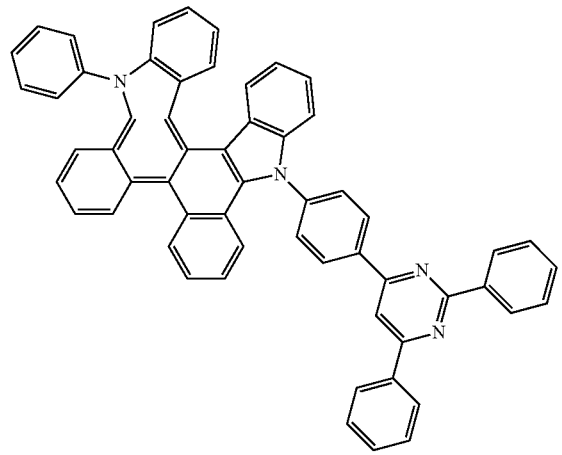
P-14
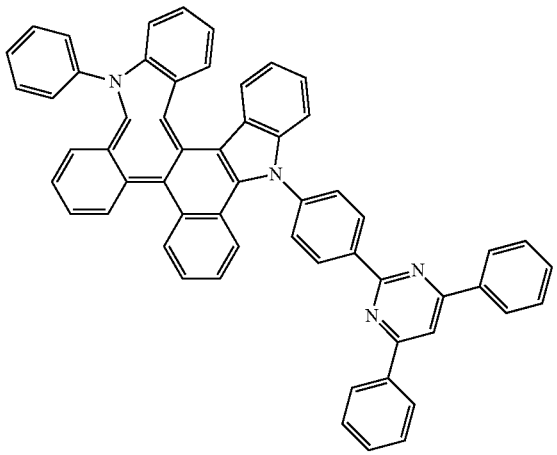
P-15
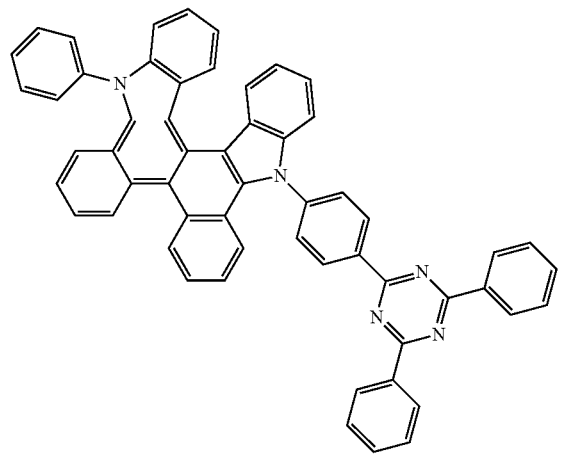
P-16
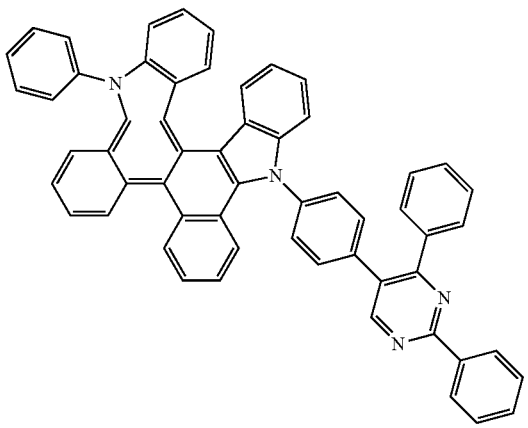

-continued
P-17
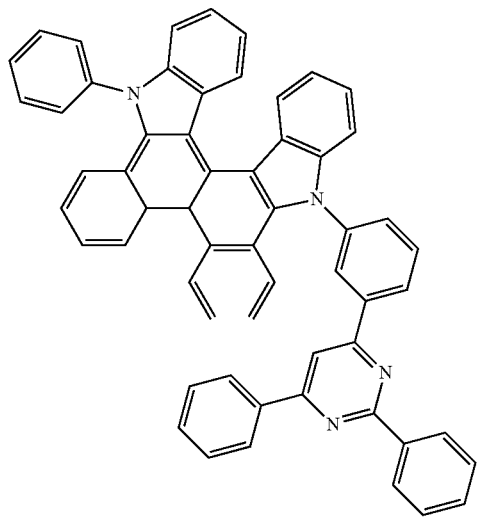
P-18
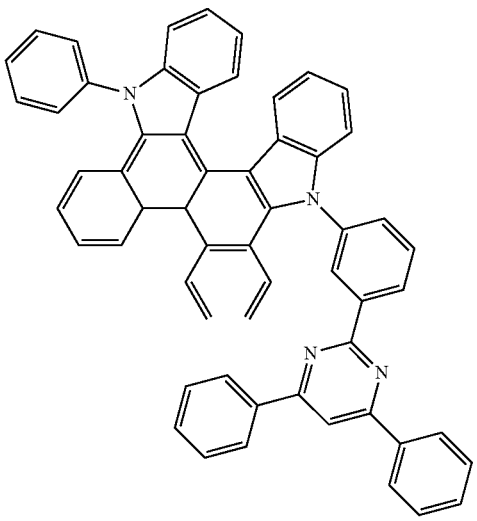
P-19
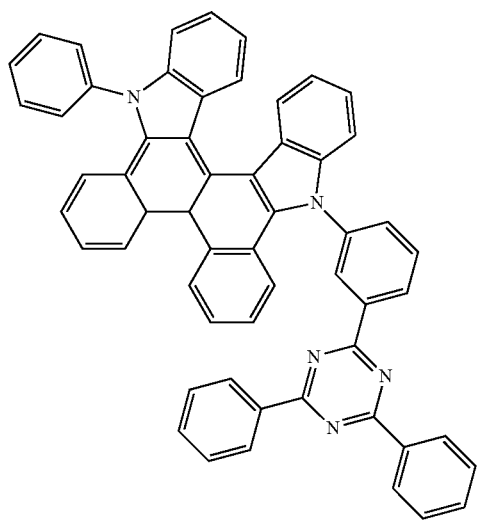
P-20
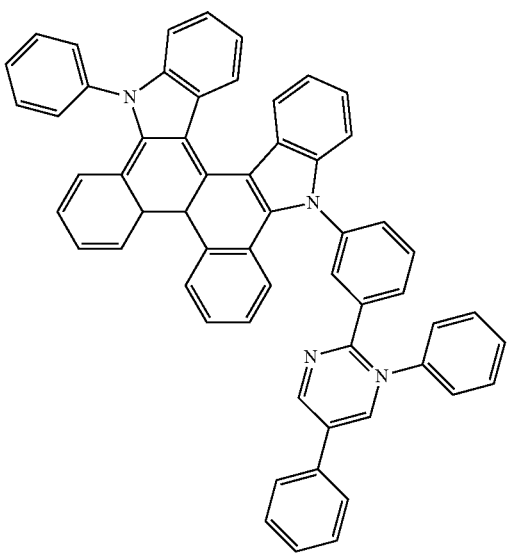
P-21
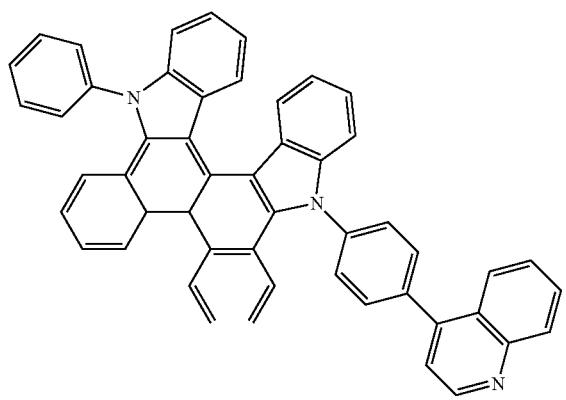
P-22
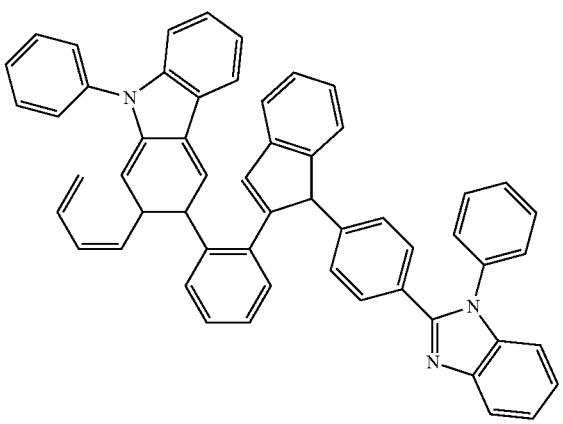

-continued
P-23
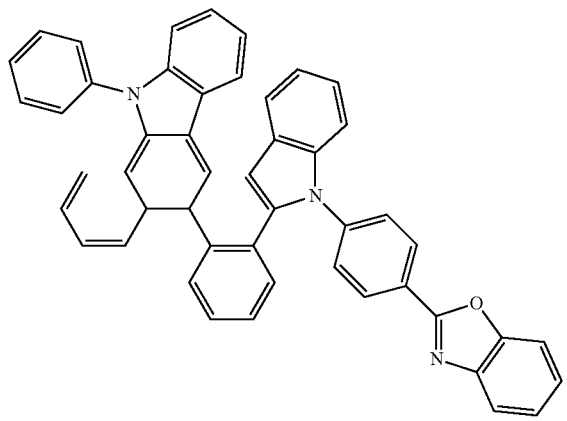
P-24
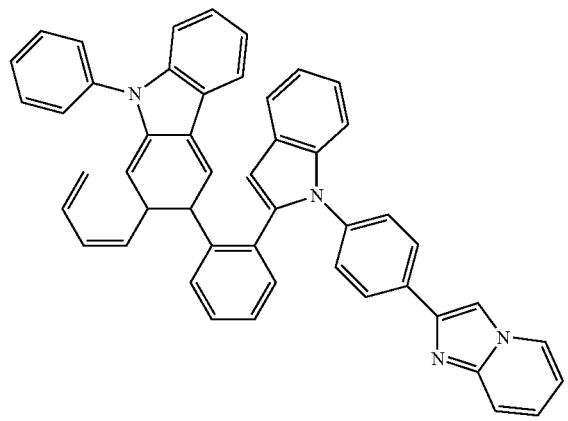
P-25
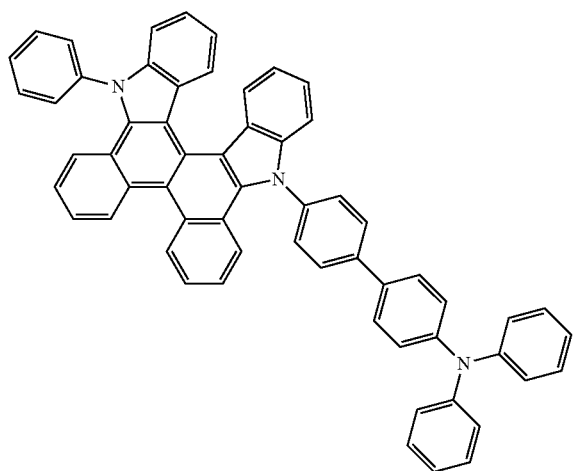
P-26
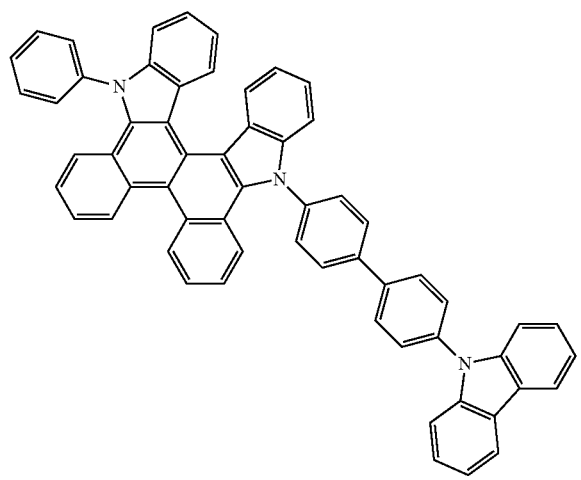
P-27
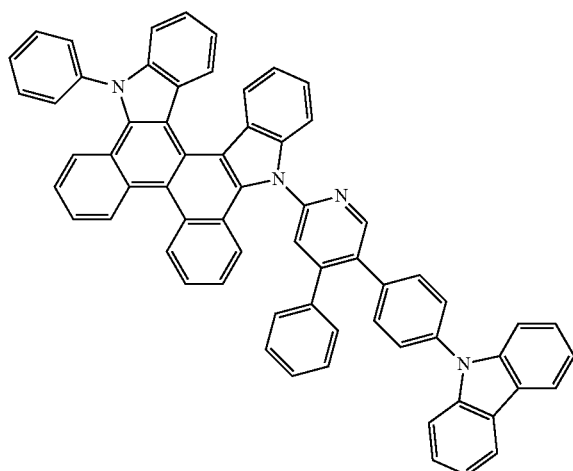
P-28
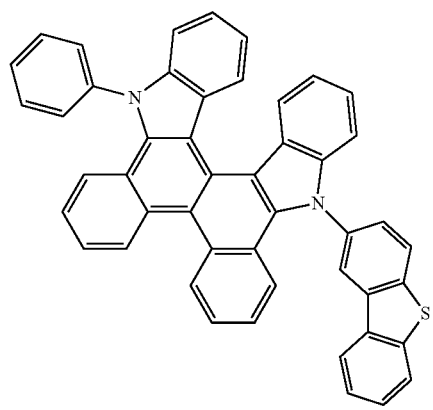

-continued
P-29
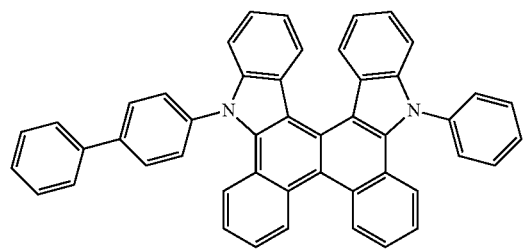
P-30
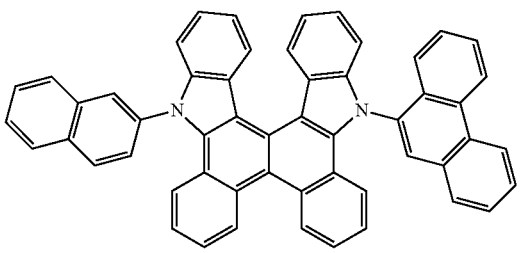
P-31
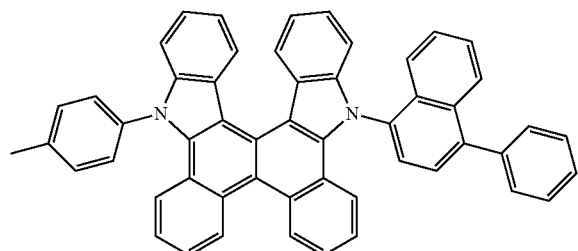
P-32
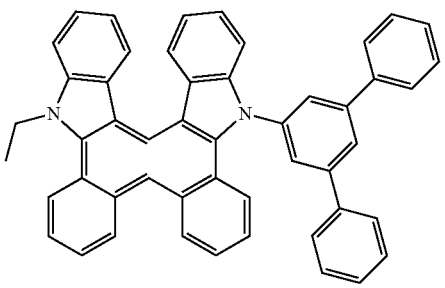
P-33
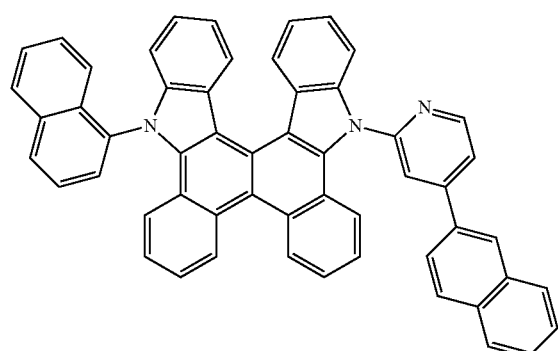
P-34
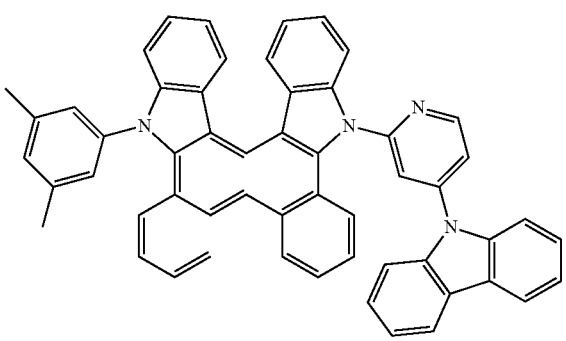
P-35
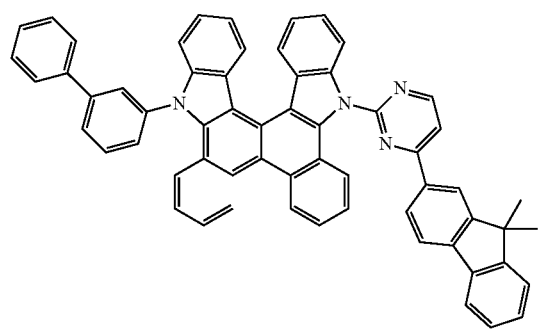
P-36
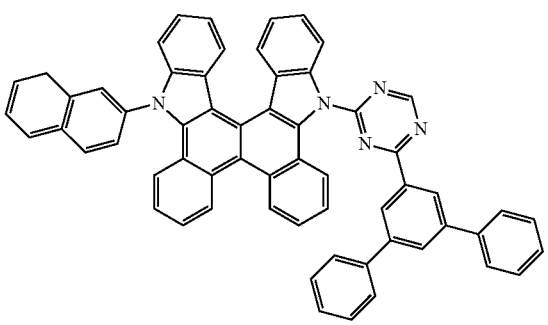
P-37
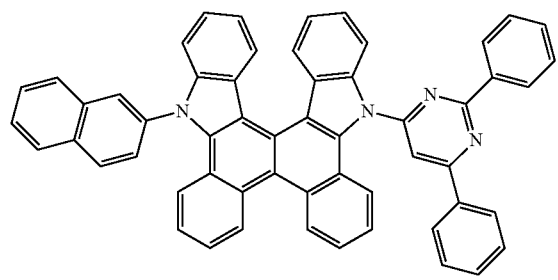
P-38
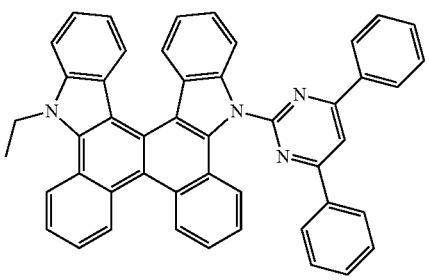

-continued
P-39
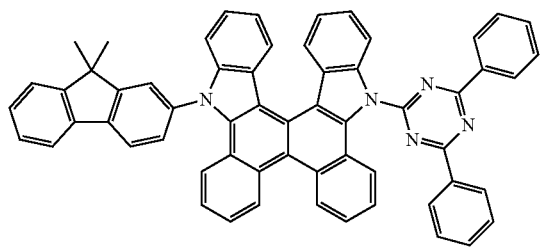
P-40
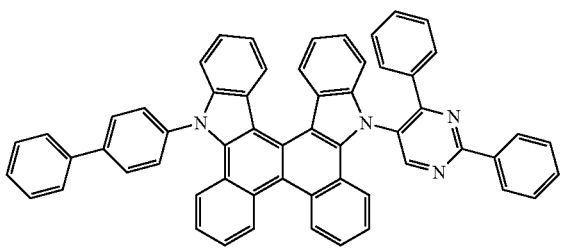
P-41
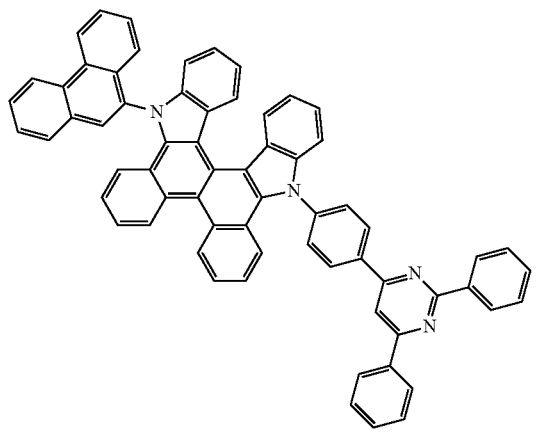
P-42
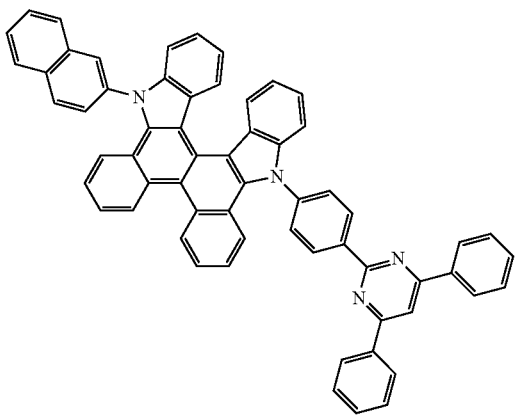
P-43
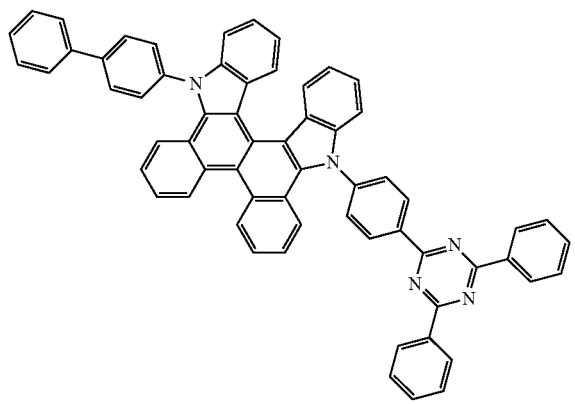
P-44
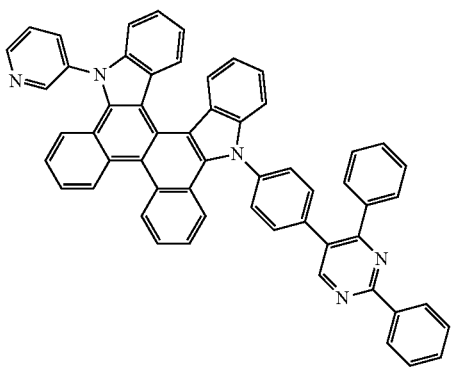
P-45
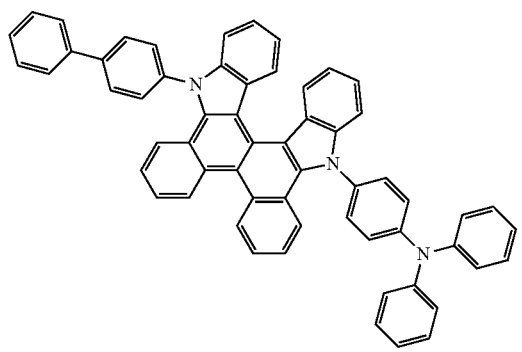
P-46
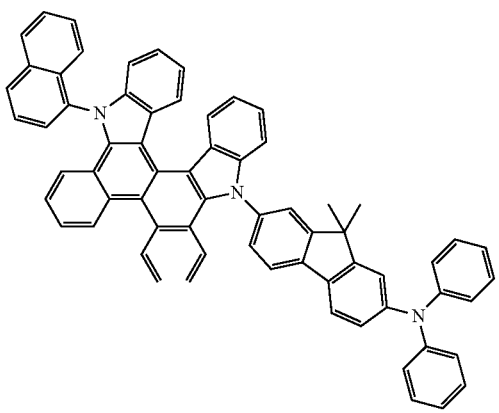

-continued
P-47
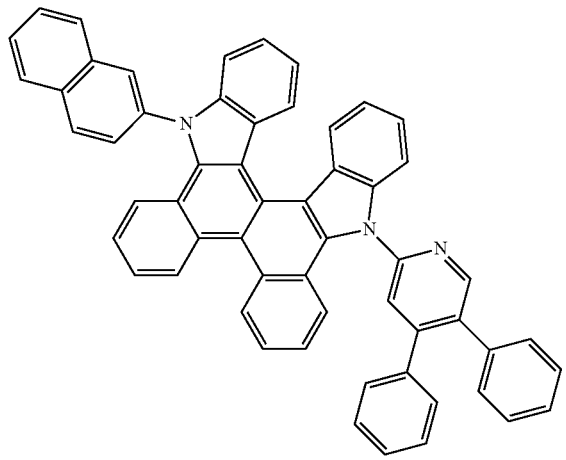
P-48
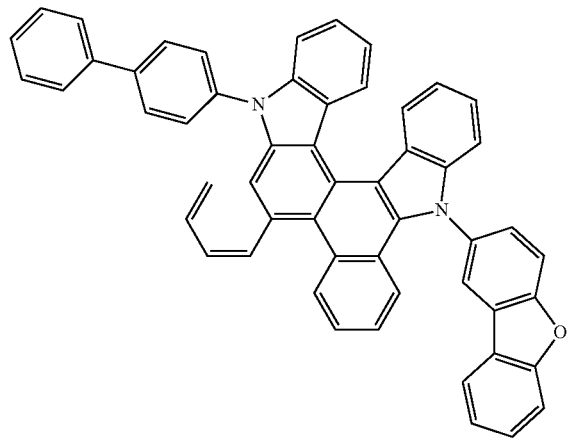
P-49
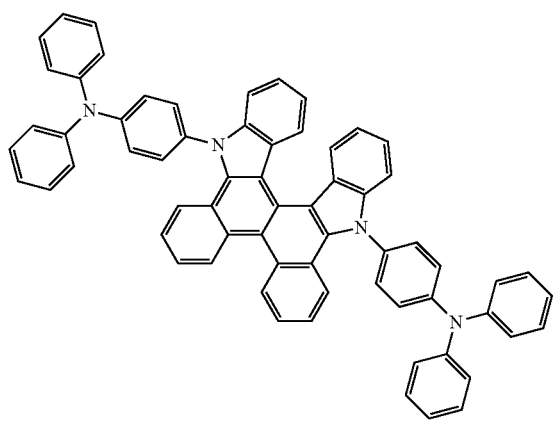
P-50
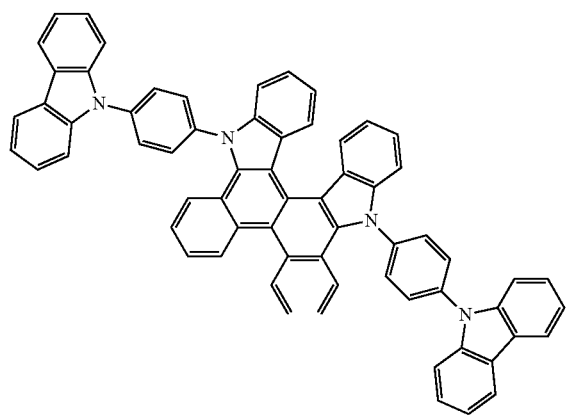
P-51
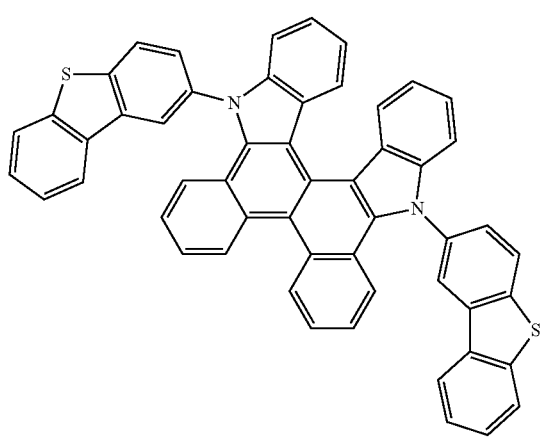

-continued
P-52
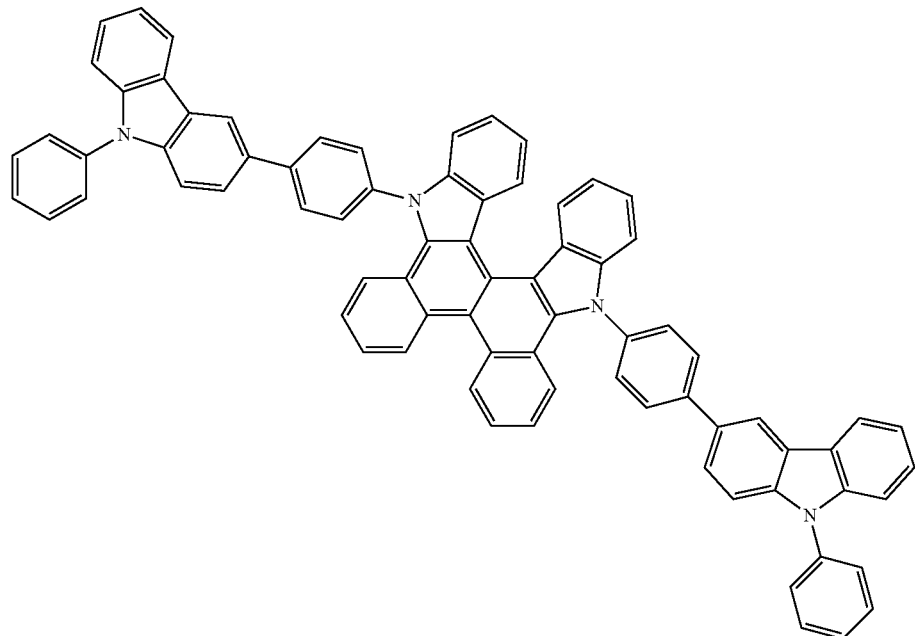
P-53
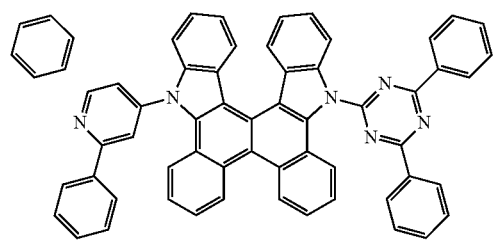
P-54
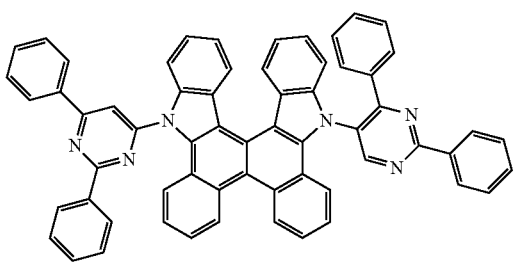
P-55
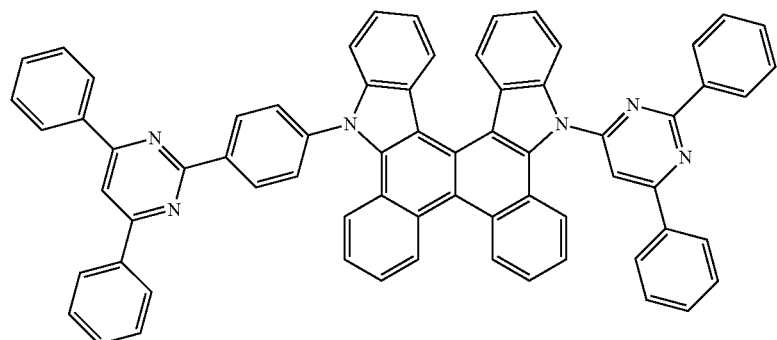
P-56
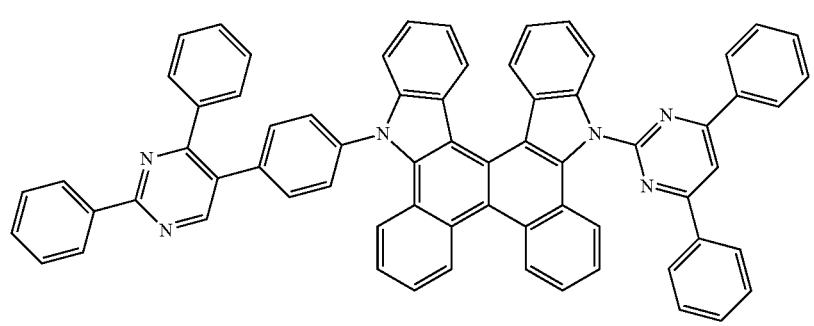

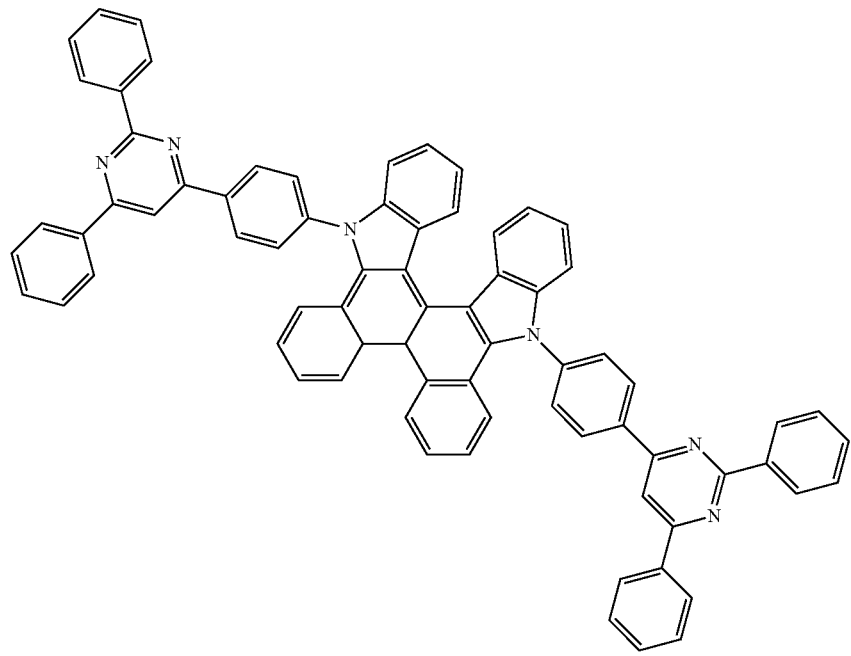
P-57
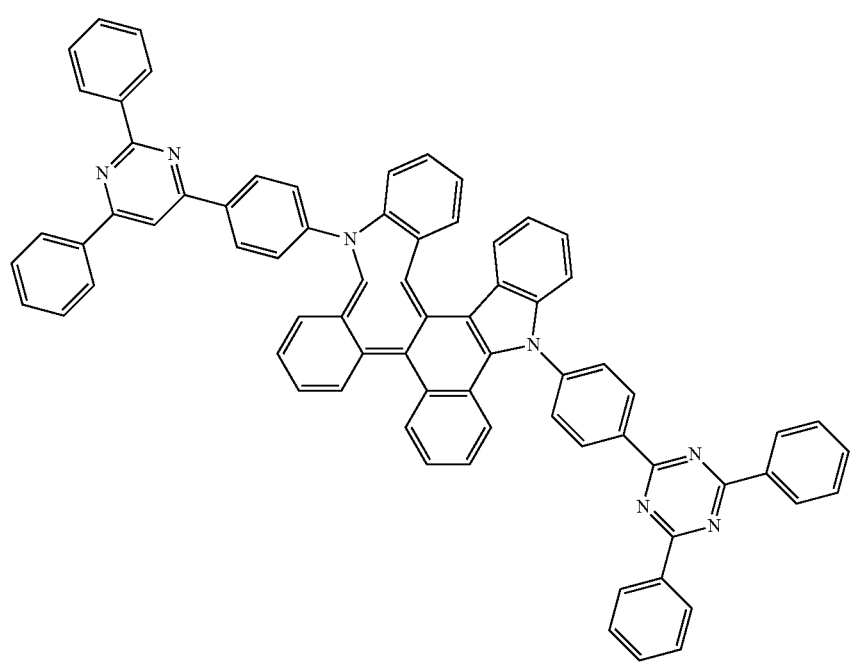
P-58

-continued
P-59
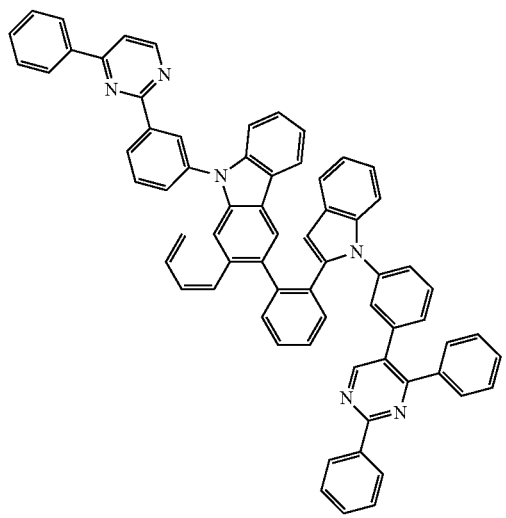
P-60
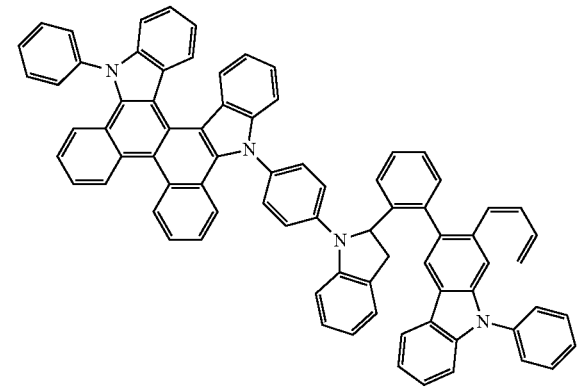
P-61
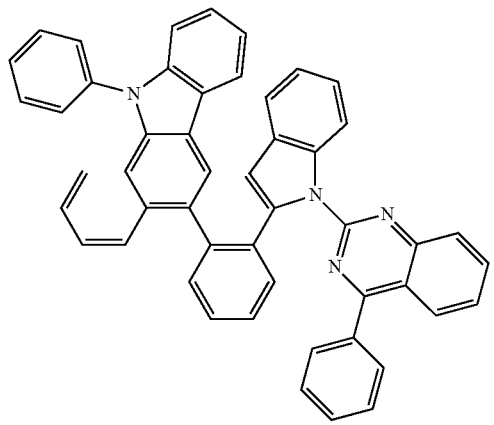
P-62
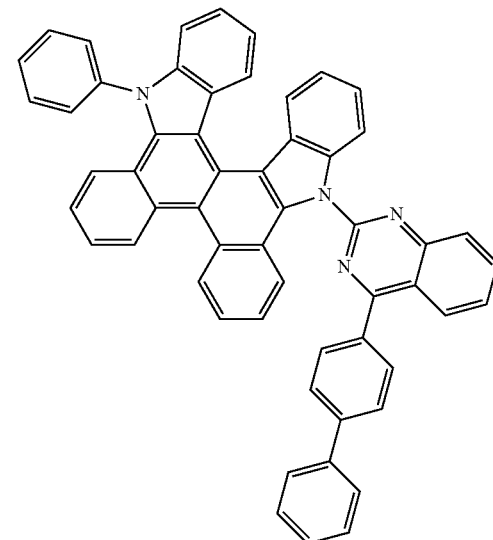
P-63
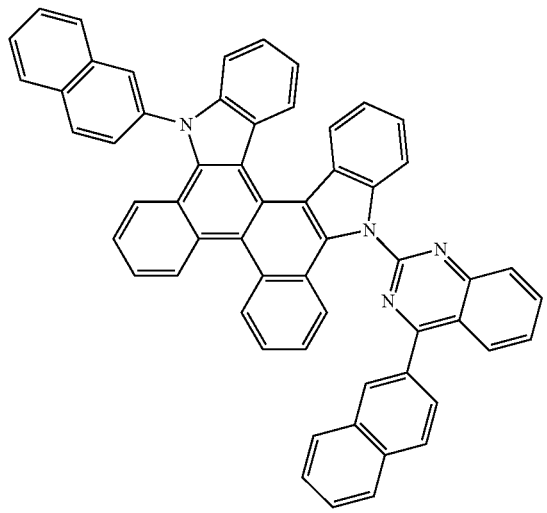
P-64
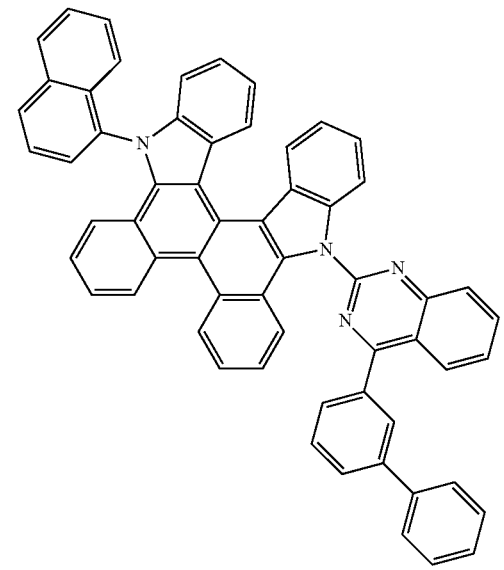

-continued
P-65
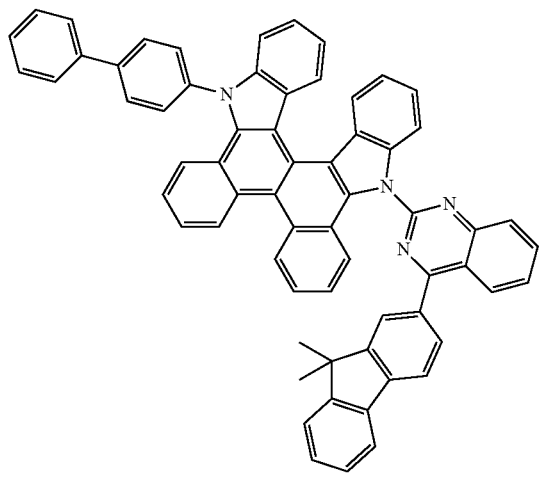
P-66
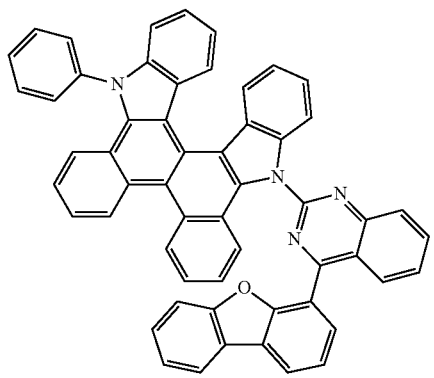
P-67
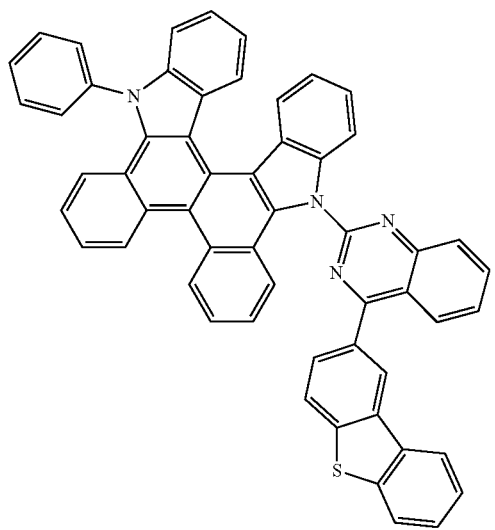
P-68
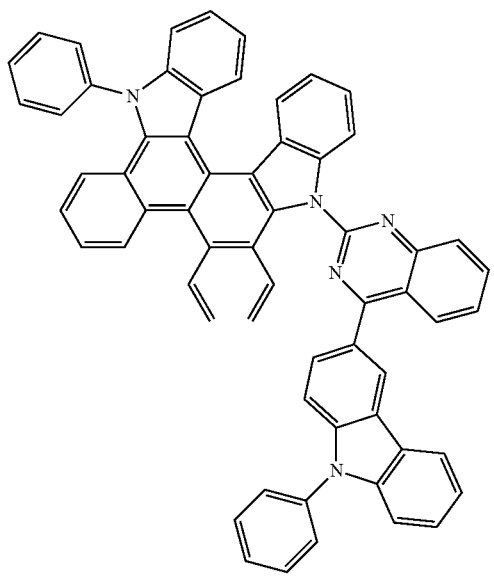
P-69
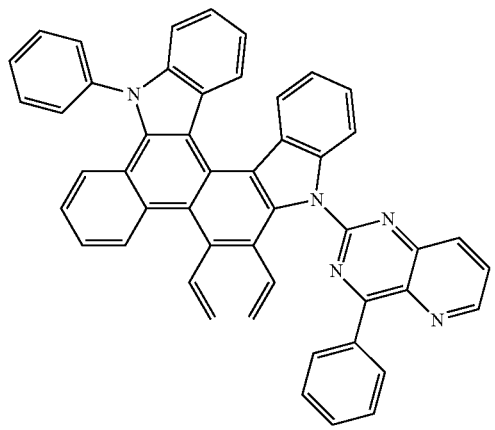
P-70
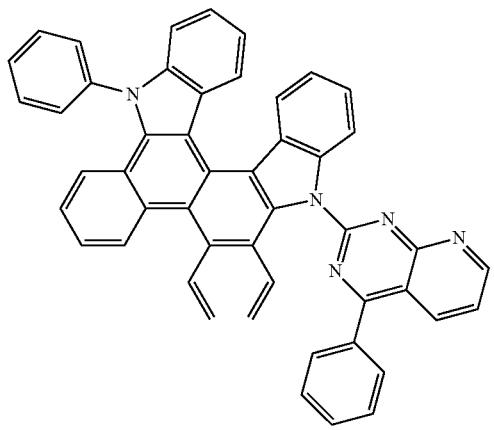

-continued
P-71
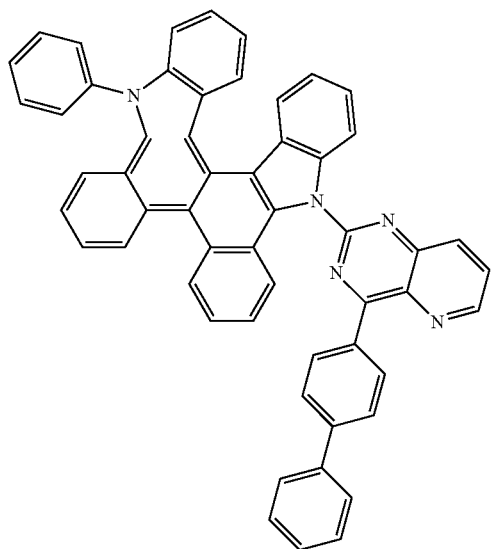
P-72
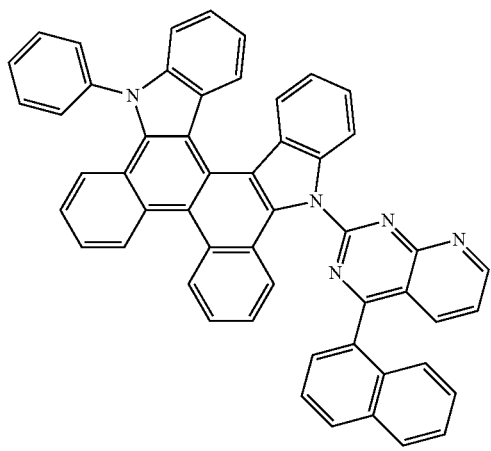
P-73
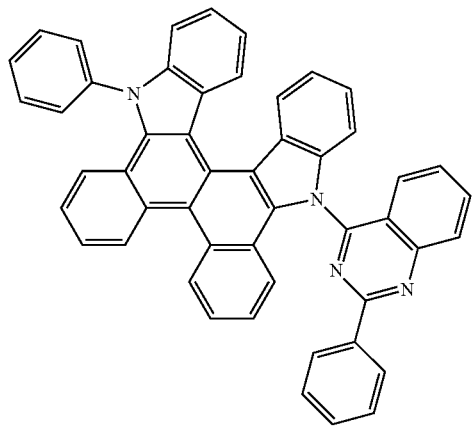
P-74
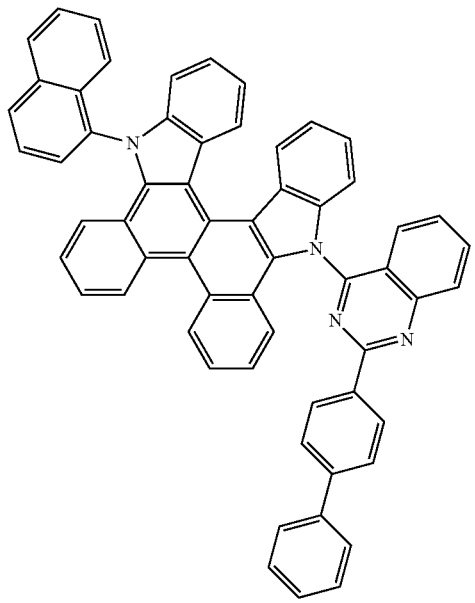

-continued
P-75
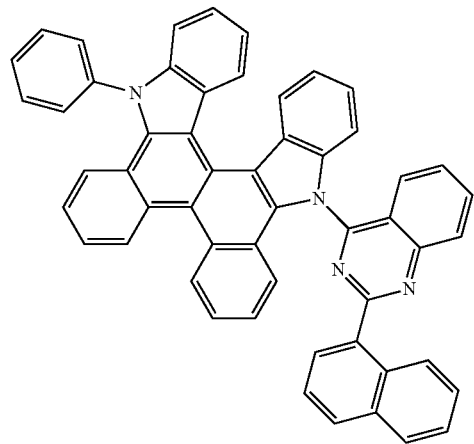
P-76
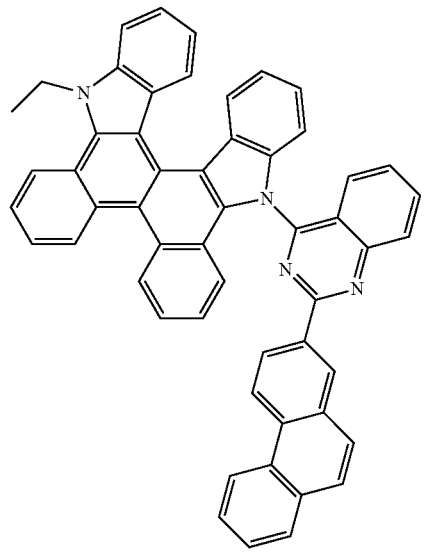
P-77
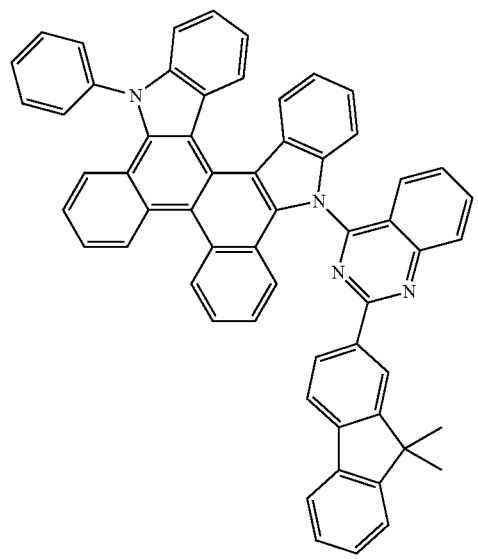
P-78
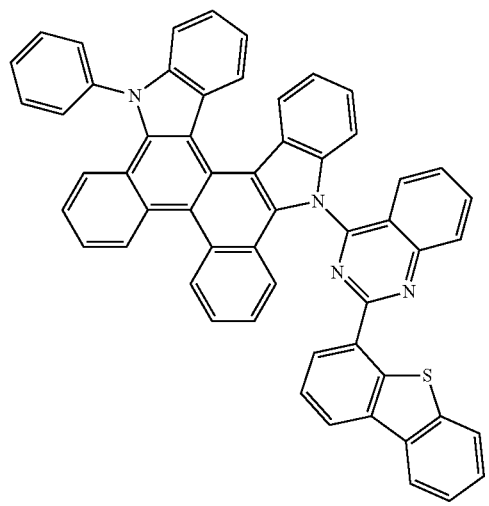

-continued
P-79
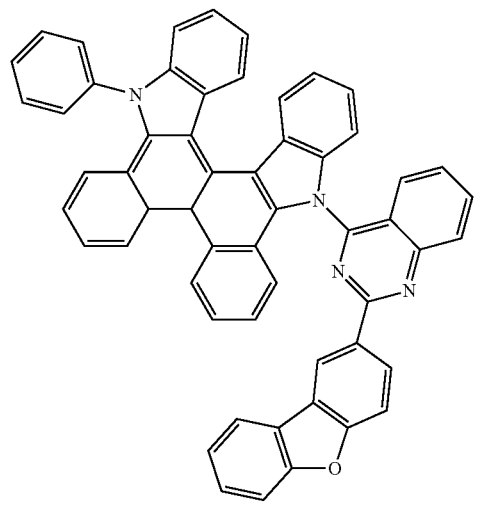
P-80
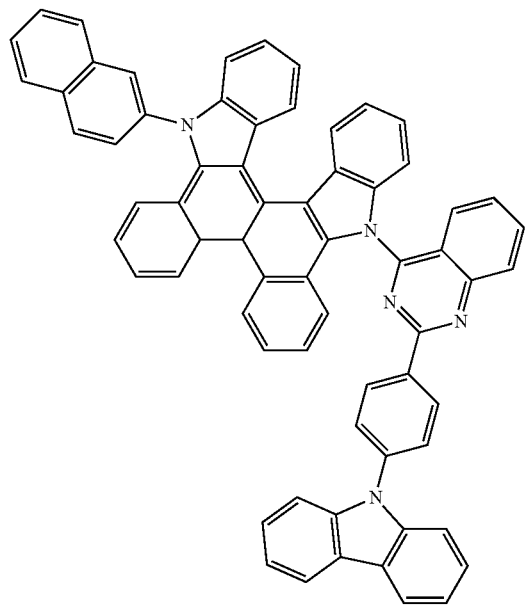
P-81
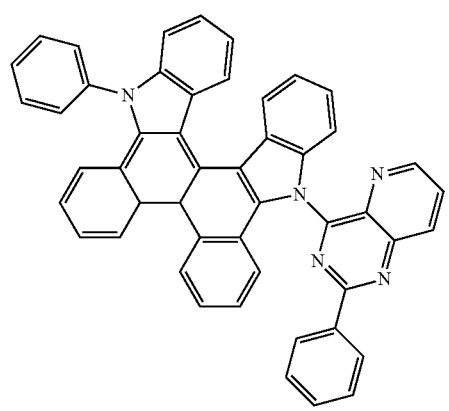
P-82
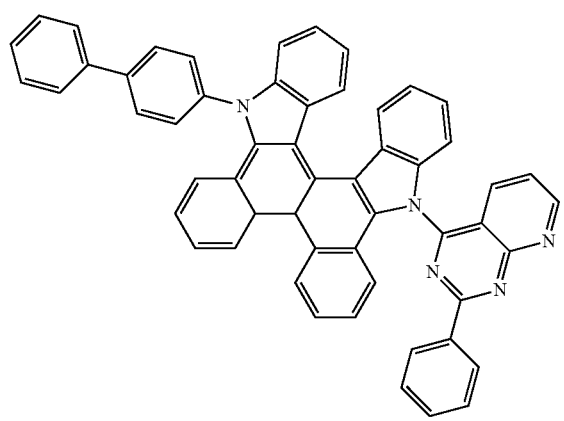
P-83
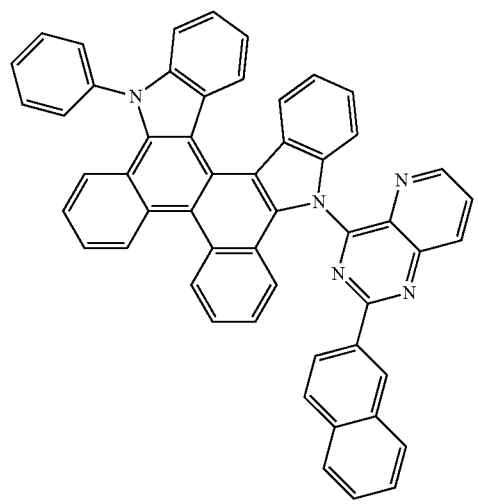
P-84
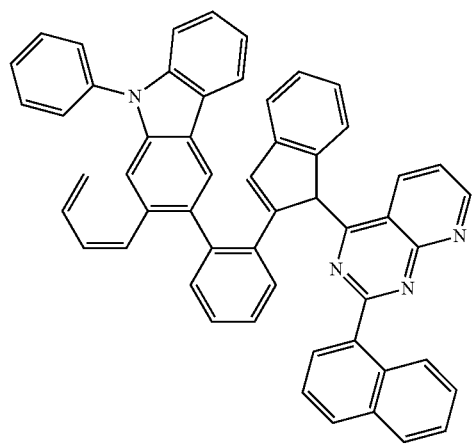

-continued
P-85
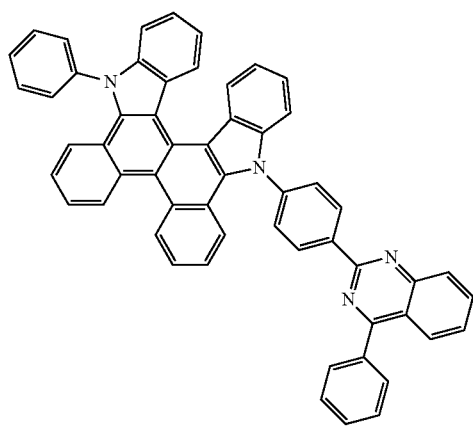
P-86
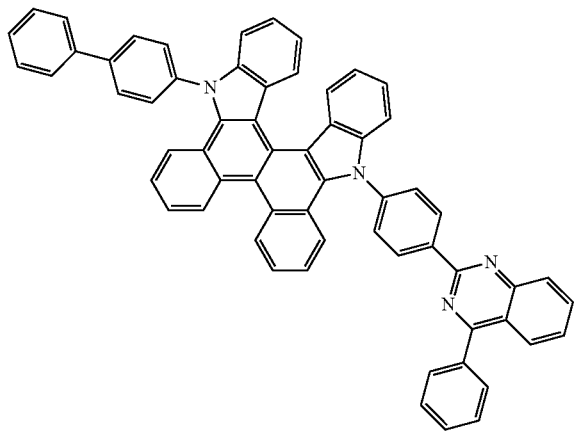
P-87
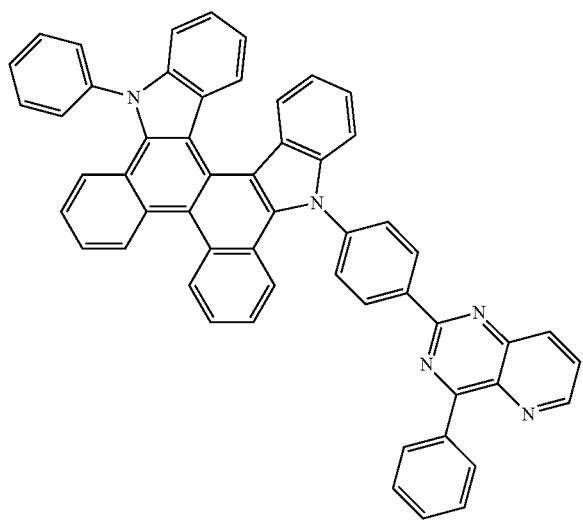
P-88
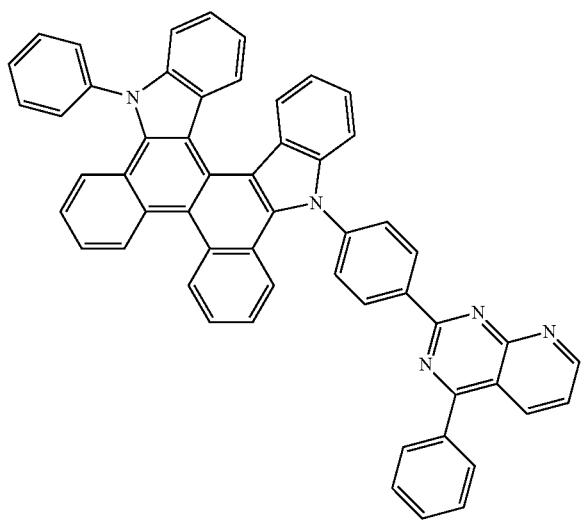
P-89
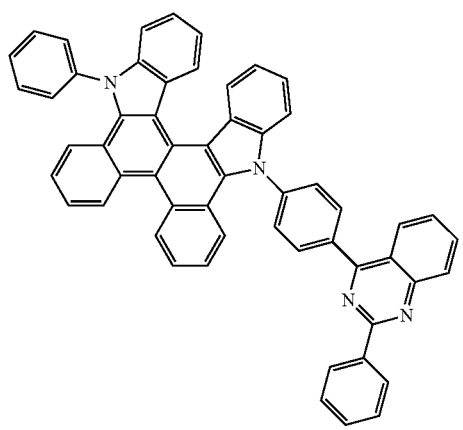
P-90
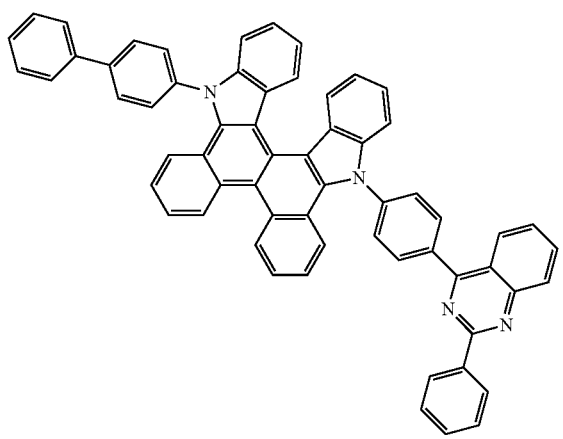

P-91

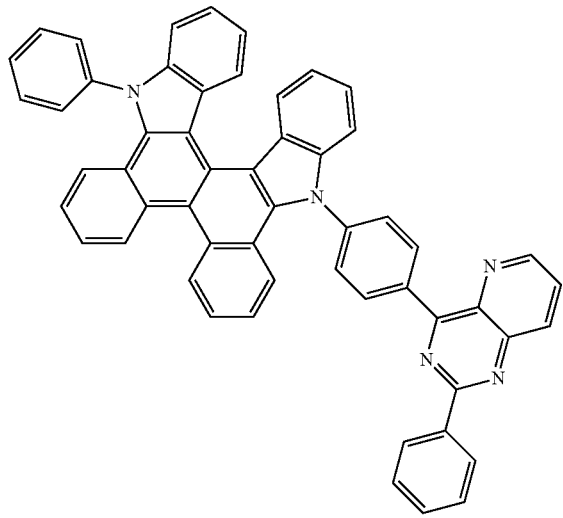

P-92

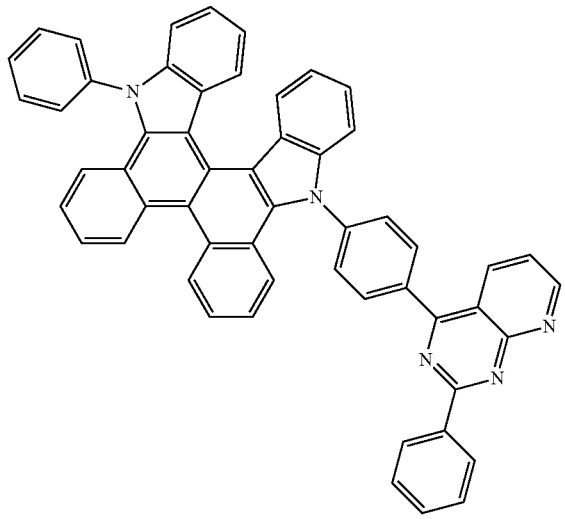

Hereinafter, Synthesis Examples of the inventive compound represented by Formula 1 according to the present invention and Preparation Examples of an organic electric element will be described in detail by way of example. However, the following examples are only for illustrative purposes and are not intended to limit the scope of the invention.

Synthesis Example

The final product according to the present invention may be synthesized by reacting Sub 1 and Sub 2 as illustrated in, but not limited to, the following Reaction Scheme 1.

⟨Reaction scheme 1⟩

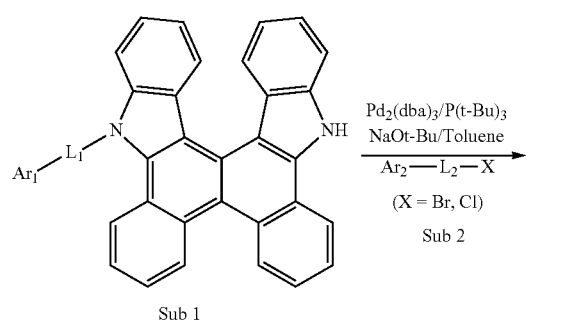

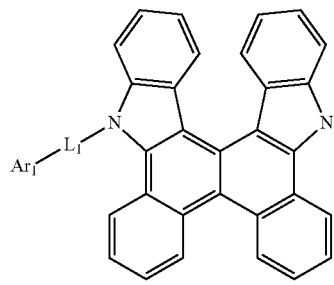

Final Products

1. Synthesis Method of Sub 1

Sub 1 of Reaction Scheme 1 can be synthesized according to, but not limited to, the following Reaction Scheme 2.

⟨Reaction Scheme 2⟩

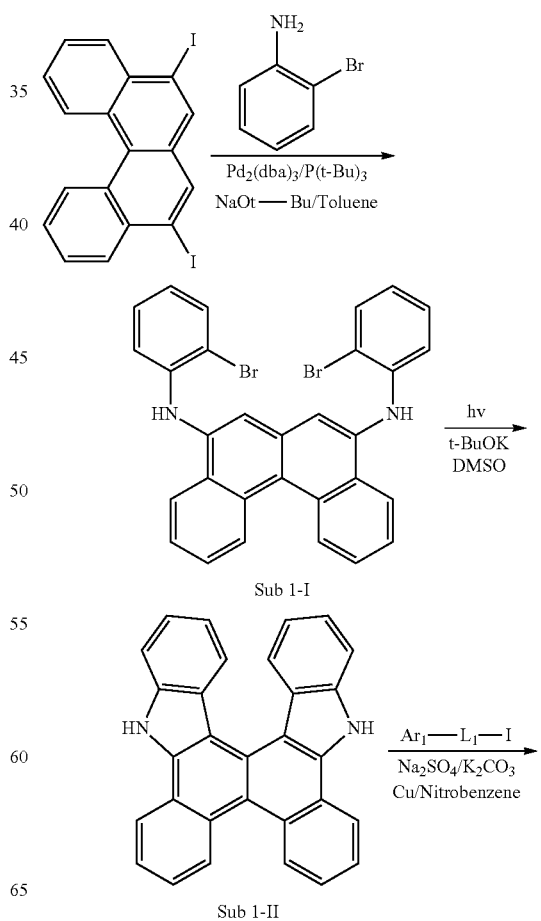

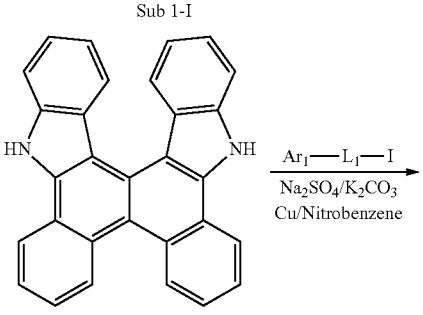

Sub 1-II

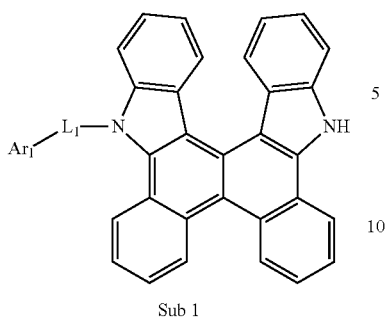

Sub 1

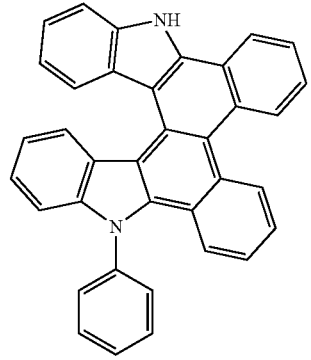

Sub 1-2

To a solution of iodobenzene (16.32 g, 80 mmol), the starting material, in nitrobenzene in a round bottom flask were added Sub 1-II (32.51 g, 80 mmol), Na$_2$SO$_4$ (11.36 g, 80 mmol), K$_2$CO$_3$ (16.56 g, 120 mmol), Cu (1.52 g, 24 mmol), and the solution was stirred at 200° C. Upon completion of the reaction, nitrobenzene was distilled off, and the reaction product was extracted with CH$_2$Cl$_2$ and water. The extracted organic layer was dried with MgSO$_4$ and concentrated, and then the produced organic material was purified by a silica gel column chromatography and recrystallization to obtain 17.75 g of the product (yield: 46%).

(2) Synthesis Method of Sub 1-6

⟨Reaction Scheme 4⟩

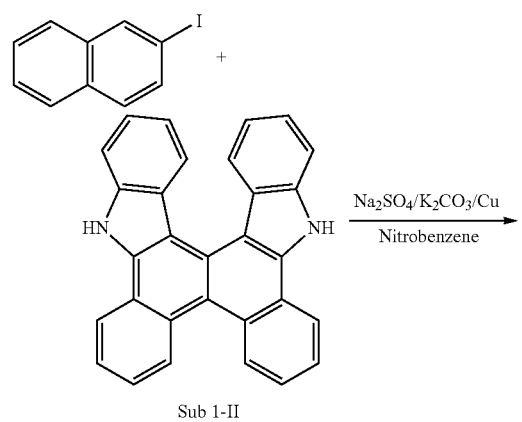

Sub 1-II

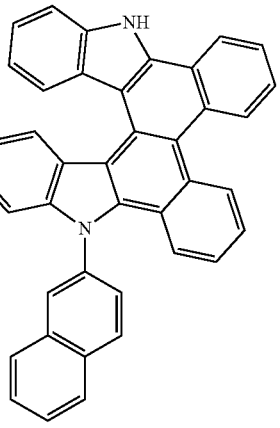

Sub 1-6

Synthesis Method of Sub 1-1

To a solution of 5,8-diiodobenzo[c]phenanthrene (108.41 g, 225.8 mmol; a starting material) in toluene in a round bottom flask, were added 2-bromoaniline (116.53 g, 677.4 mmol), Pd$_2$(dba)$_3$ (6.2 g, 6.8 mmol), 50% P(t-Bu)$_3$ (8.8 ml, 18.1 mmol), NaOt-Bu (65.11 g, 677.4 mmol), and the solution was stirred at room temperature. Upon completion of the reaction, the reaction solution was extracted with CH$_2$Cl$_2$ and water. The extract of organic layer was dried over MgSO$_4$ and concentrated to a product of organic material. The product was purified by a silica gel column chromatography and recrystallization to obtain 79.57 g of the product (yield: 62%).

Synthesis Method of Intermediate for Sub 1-II

A solution of t-BuOK (62.84 g, 560.1 mmol) in DMSO (deoxygenated) was stirred for 5 minutes, then the obtained Sub 1-I (79.57 g, 140 mmol) was added to the solution, followed by UV-irradiation. Upon completion of the reaction, it was quenched by adding water and ammonium nitrate. The solution was extracted with CH$_2$Cl$_2$ and water. The organic layer extract was dried with MgSO$_4$ and concentrated to produce a product. The produced organic material was purified by a silica gel column and recrystallization to obtain 36.99 g of the product (yield: 65%).

(1) Synthesis Method of Sub 1-2

⟨Reaction Scheme 3⟩

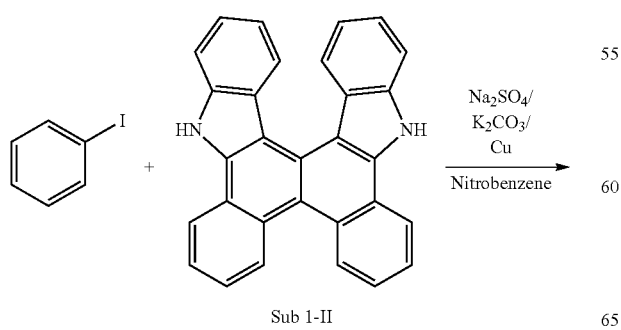

Sub 1-II 2-iodonaphthalene (11.45 g, 45.1 mmol), Sub 1-II (18.32 g, 45.1 mmol), Na₂SO₄ (6.4 g, 45.1 mmol), K₂CO₃ (9.33 g, 67.6 mmol), Cu (0.86 g, 13.5 mmol) and nitrobenzene were used to obtain 10.08 g of the product following the same synthesis method for Sub 1-2, (yield: 42%).

(3) Synthesis Method of Sub 1-8

⟨Reaction Scheme 5⟩

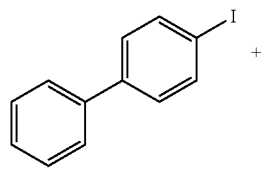

+

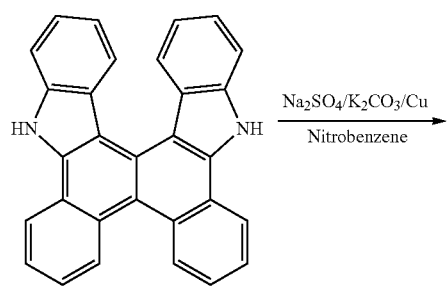
Sub 1-II

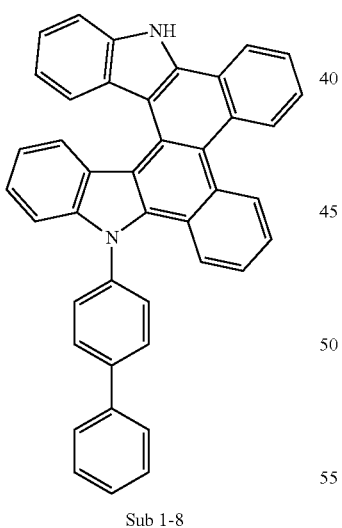
Sub 1-8

4-iodo-1,1'-biphenyl (13.73 g, 49 mmol), Sub 1-II (19.93 g, 49 mmol), Na₂SO₄ (6.96 g, 49 mmol), K₂CO₃ (10.15 g, 73.5 mmol), Cu (0.93 g, 14.7 mmol) and nitrobenzene were used to obtain 12.33 g of the product following the same synthesis method for Sub 1-2 (yield: 45%).

Examples for Sub 1 compounds include, but are not limited to, the following compounds, and FD-MS data of the compounds are given in Table 1 below:

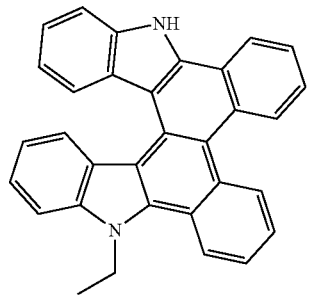
Sub 1-1

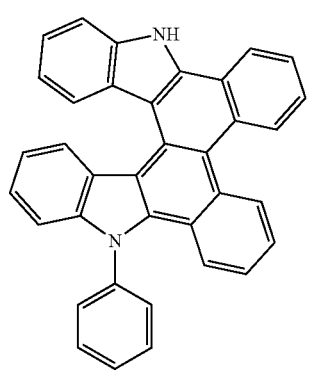
Sub 1-2

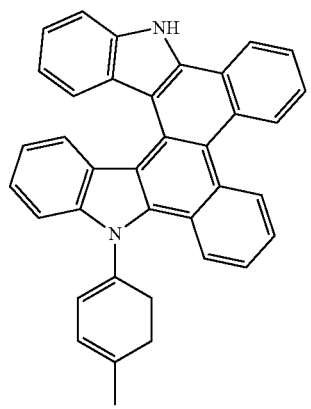
Sub 1-3

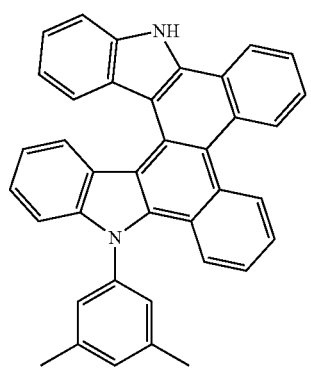
Sub 1-4

Sub 1-5
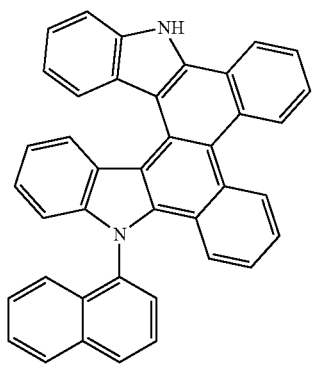
Sub 1-6
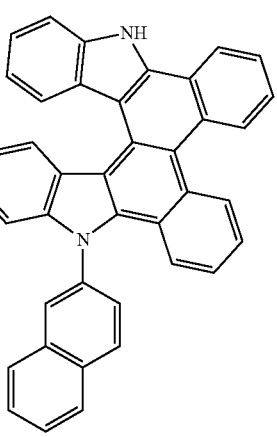
Sub 1-7
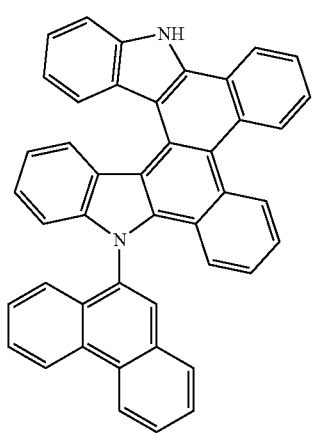
Sub 1-8
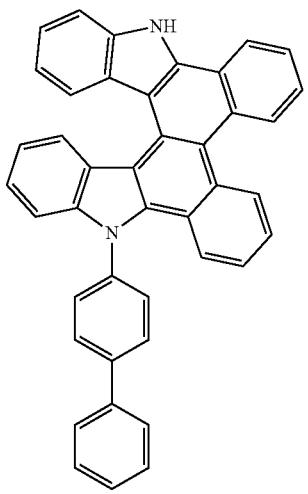
Sub 1-9
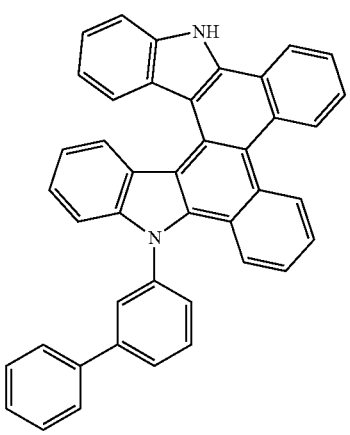
Sub 1-10
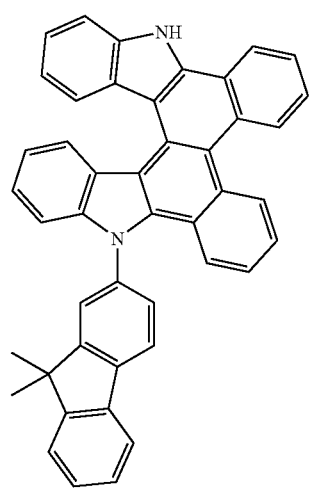

-continued
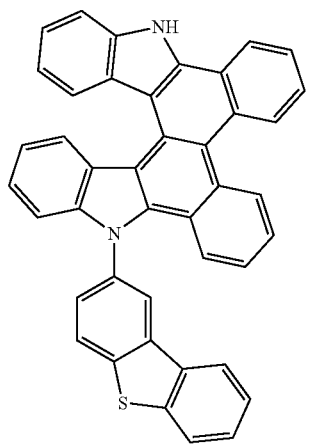
Sub 1-11
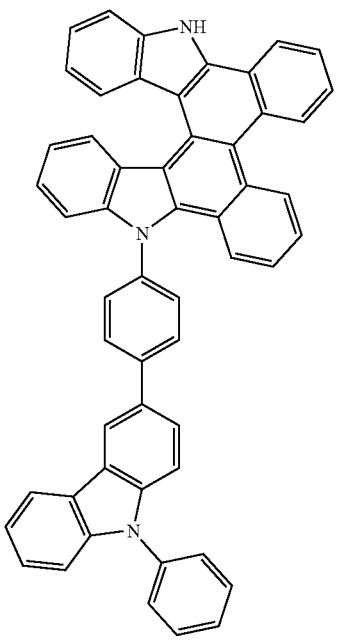
Sub 1-14
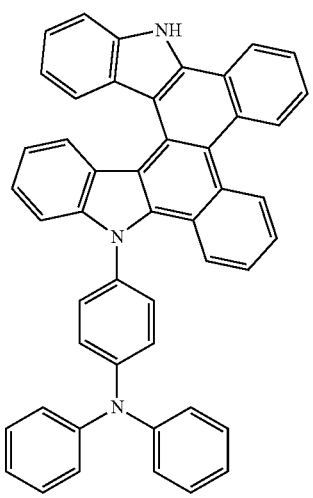
Sub 1-12
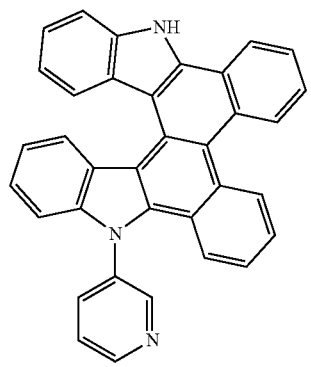
Sub 1-15
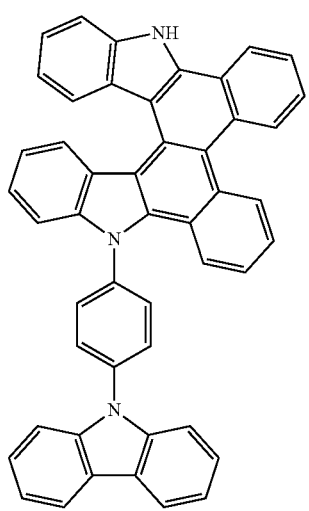
Sub 1-13
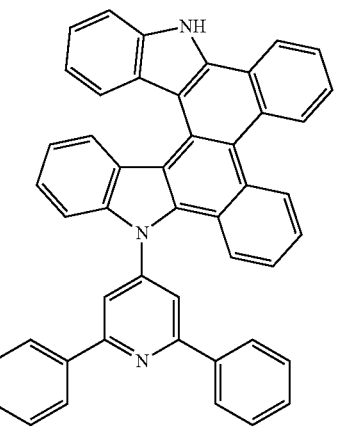
Sub 1-16

Sub 1-17

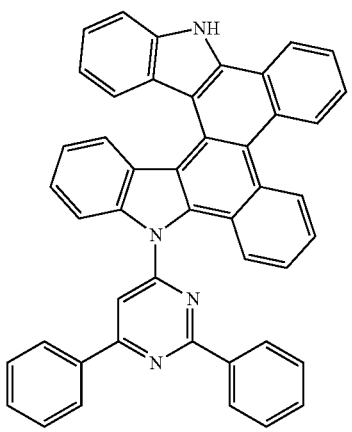

Sub 1-18

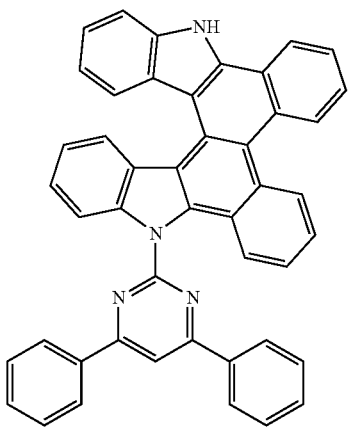

Sub 1-19

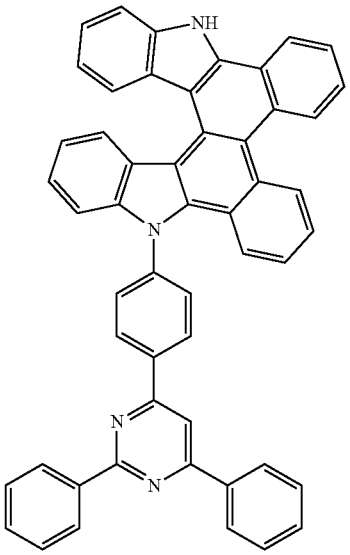

Sub 1-20

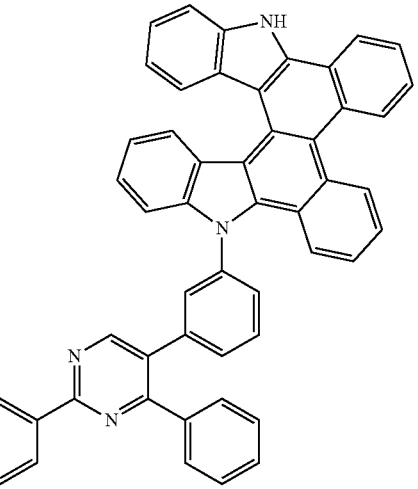

TABLE 1

| Compound | FD-MS | Compound | FD-MS |
|---|---|---|---|
| Sub 1-1 | m/z = 434.18($C_{32}H_{22}N_2$ = 434.53) | Sub 1-2 | m/z = 482.18($C_{36}H_{22}N_2$ = 482.57) |
| Sub 1-3 | m/z = 496.19($C_{37}H_{24}N_2$ = 496.60) | Sub 1-4 | m/z = 510.21($C_{38}H_{26}N_2$ = 510.63) |
| Sub 1-5 | m/z = 532.19($C_{40}H_{24}N_2$ = 532.63) | Sub 1-6 | m/z = 532.19($C_{40}H_{24}N_2$ = 532.63) |
| Sub 1-7 | m/z = 582.21($C_{44}H_{26}N_2$ = 582.69) | Sub 1-8 | m/z = 558.21($C_{42}H_{26}N_2$ = 558.67) |
| Sub 1-9 | m/z = 558.21($C_{42}H_{26}N_2$ = 558.67) | Sub 1-10 | m/z = 598.24($C_{45}H_{30}N_2$ = 598.73) |
| Sub 1-11 | m/z = 588.17($C_{42}H_{24}N_2$ = 588.72) | Sub 1-12 | m/z = 649.25($C_{48}H_{31}N_2$ = 649.78) |
| Sub 1-13 | m/z = 647.24($C_{48}H_{29}N_3$ = 647.76) | Sub 1-14 | m/z = 723.27($C_{54}H_{33}N_3$ = 723.86) |
| Sub 1-15 | m/z = 483.17($C_{35}H_{21}N_3$ = 483.56) | Sub 1-16 | m/z = 635.24($C_{47}H_{29}N_3$ = 635.75) |
| Sub 1-17 | m/z = 636.23($C_{46}H_{28}N_4$ = 636.74) | Sub 1-18 | m/z = 636.23($C_{46}H_{28}N_4$ = 636.74) |
| Sub 1-19 | m/z = 712.26($C_{52}H_{32}N_4$ = 712.84) | Sub 1-20 | m/z = 712.26($C_{52}H_{32}N_4$ = 712.84) |

2. Synthesis Method of Sub 2
Examples for Ar$_2$-L$_2$-X (X=Br, Cl) of Sub 2 compounds include, but are not limited to, the following compounds, and FD-MS data of the compounds are given in Table 2 below:
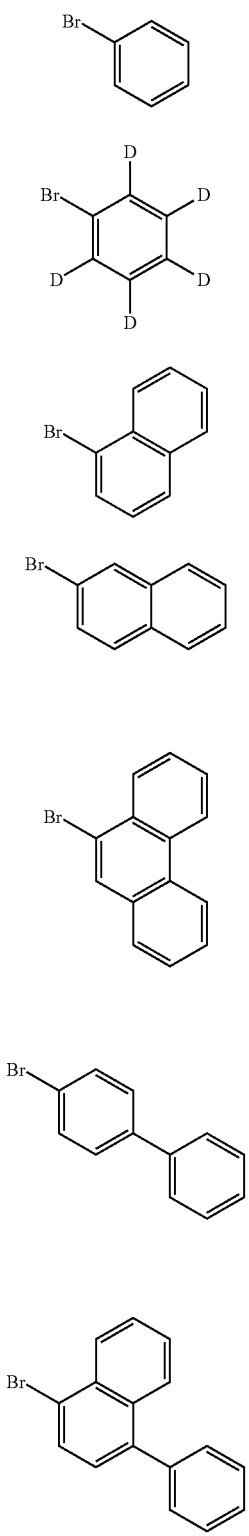
Sub 2-1
Sub 2-2
Sub 2-3
Sub 2-4
Sub 2-5
Sub 2-6
Sub 2-7
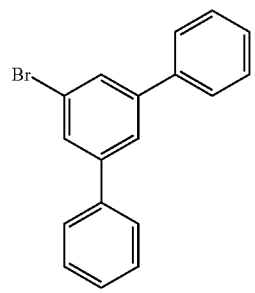
Sub 2-8
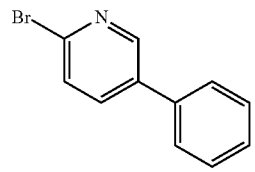
Sub 2-9
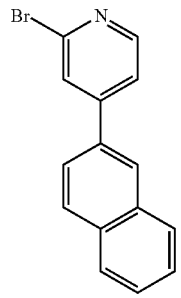
Sub 2-10
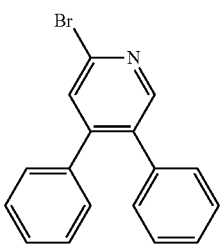
Sub 2-11
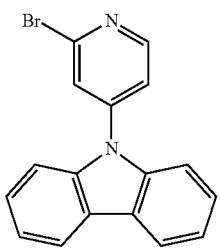
Sub-2-12

-continued
Sub-2-13
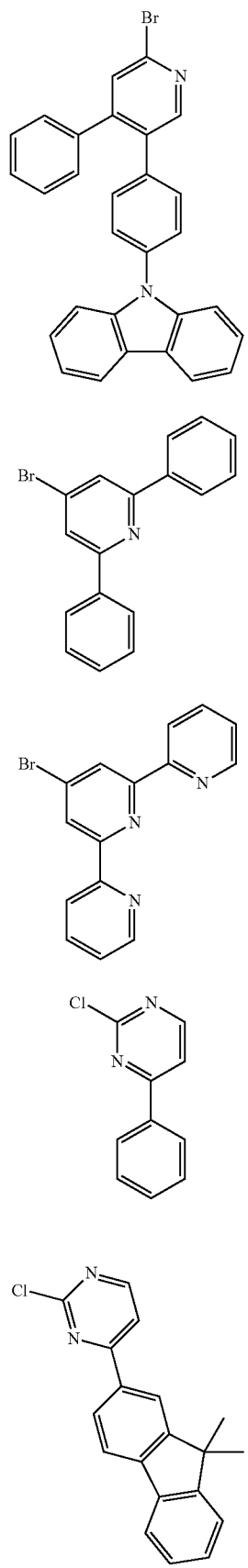
Sub-2-14
Sub-2-15
Sub-2-16
Sub-2-17
-continued
Sub 2-18
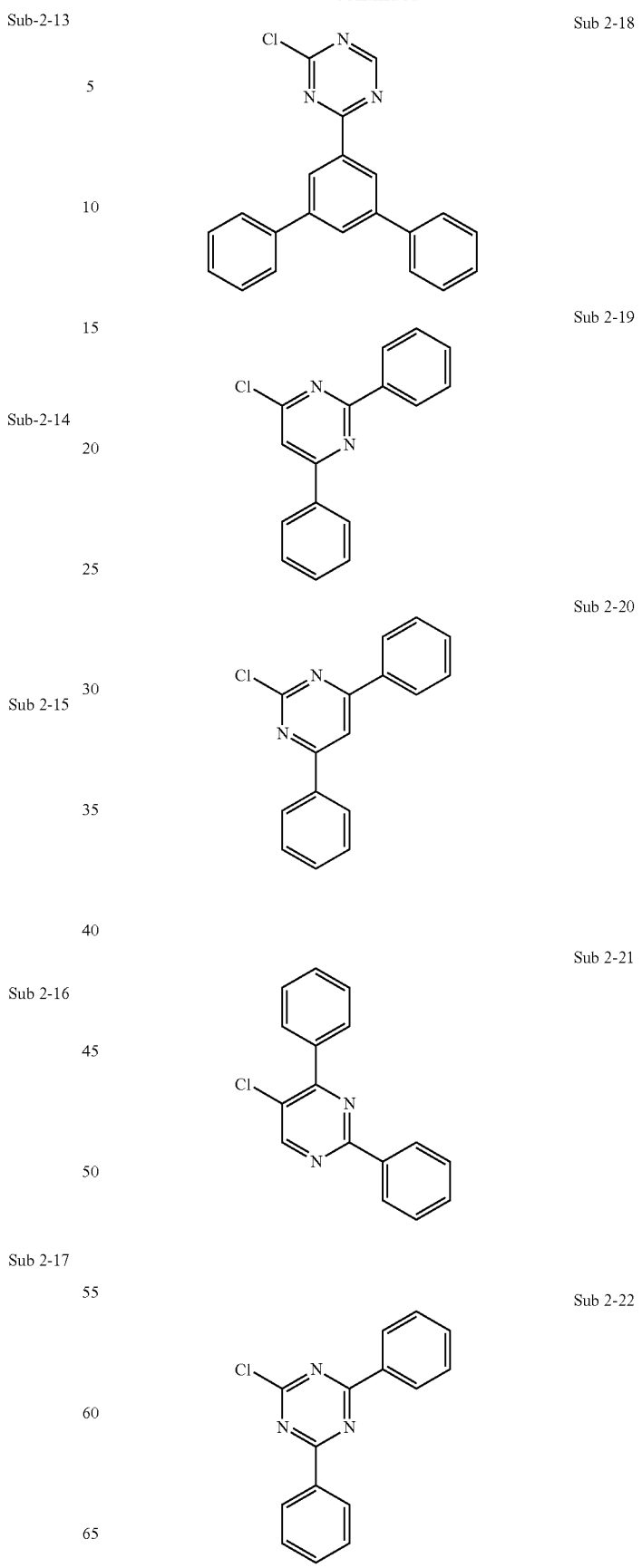
Sub 2-19
Sub 2-20
Sub 2-21
Sub 2-22

Sub 2-23
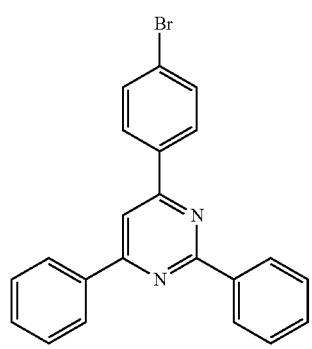
Sub 2-24
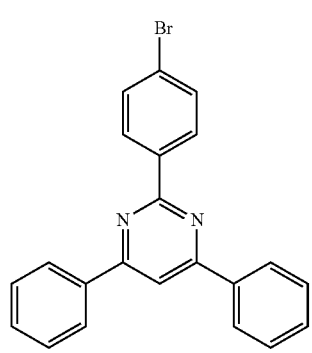
Sub 2-25
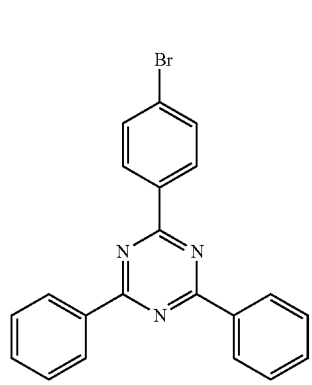
Sub 2-26
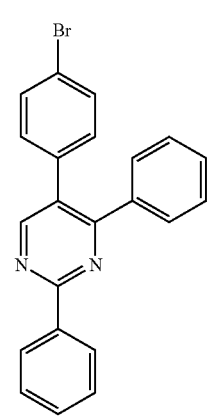
Sub 2-27
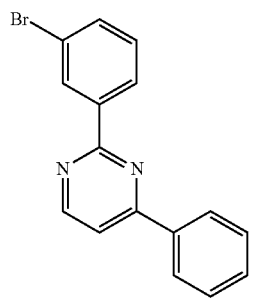
Sub 2-28
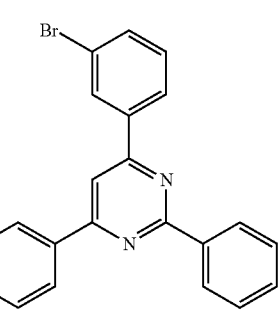
Sub 2-29
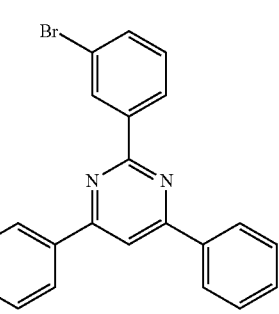
Sub 2-30
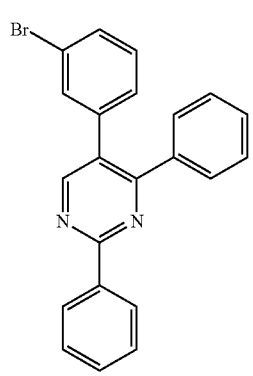
Sub 2-31
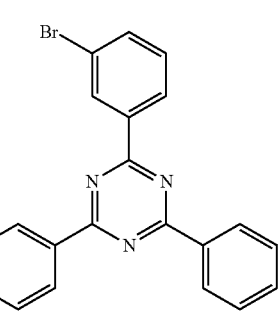

Sub 2-32
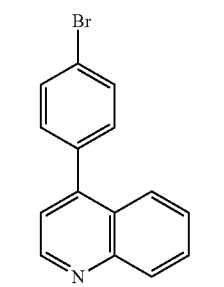
Sub 2-33
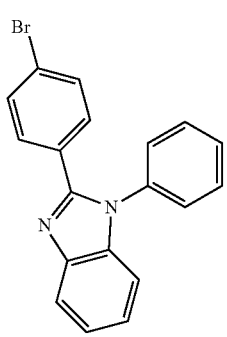
Sub 2-34
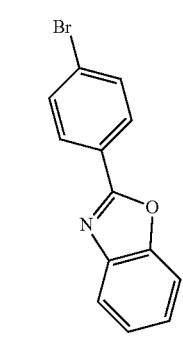
Sub 2-35
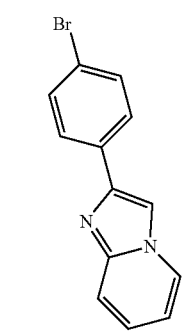
Sub 2-36
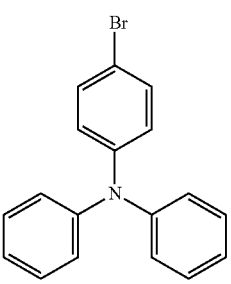
Sub 2-37
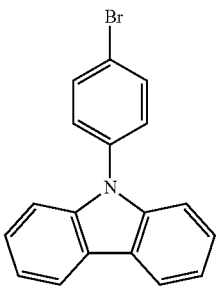
Sub 2-38
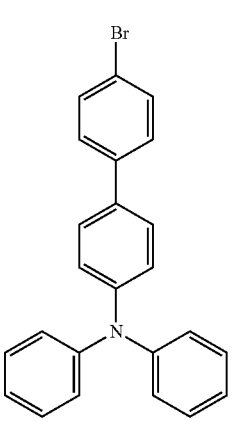
Sub 2-39
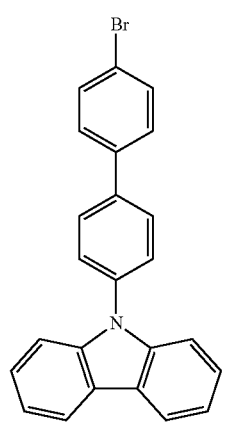
Sub 2-40
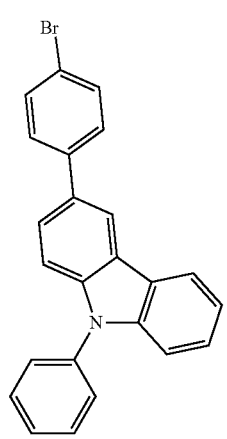

-continued
Sub 2-41
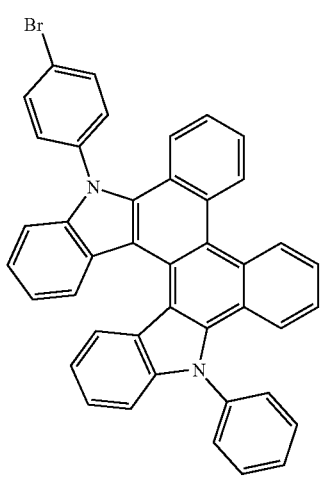
Sub 2-42
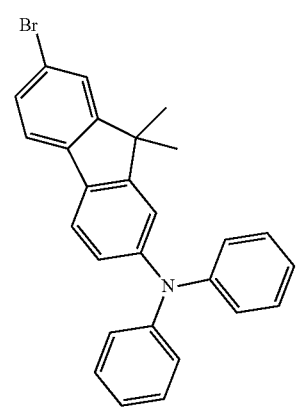
Sub 2-43
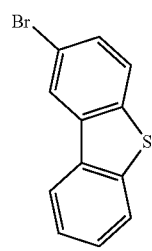
Sub 2-44
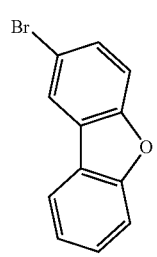
Sub 2-45
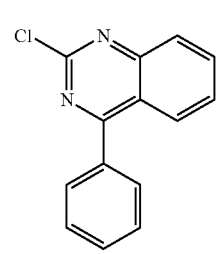
-continued
Sub 2-46
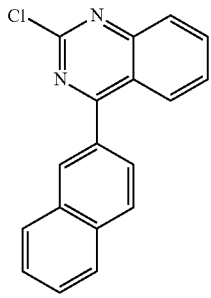
Sub 2-47
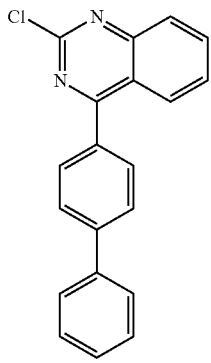
Sub 2-48
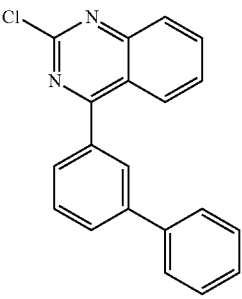
Sub 2-49
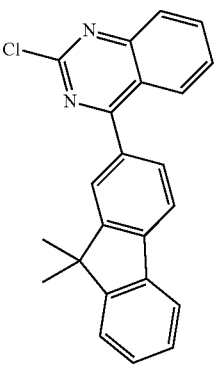
Sub 2-50
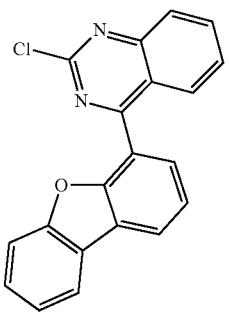

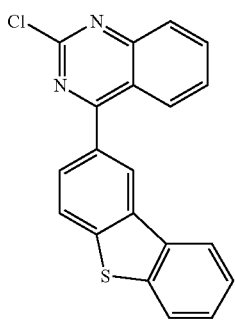
Sub 2-51
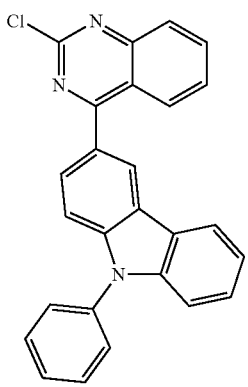
Sub 2-52
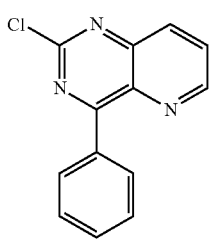
Sub 2-53
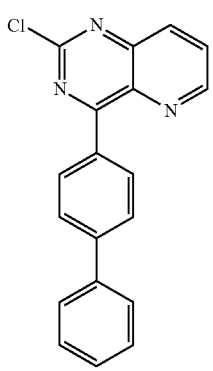
Sub 2-54
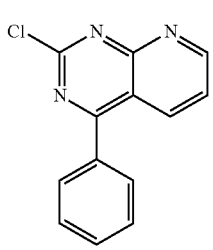
Sub 2-55
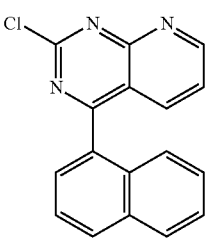
Sub 2-56
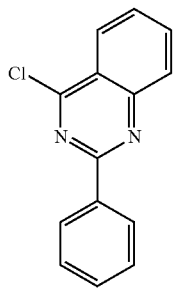
Sub 2-57
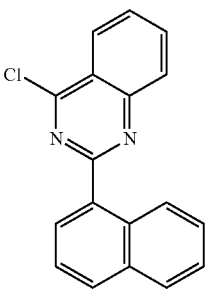
Sub 2-58
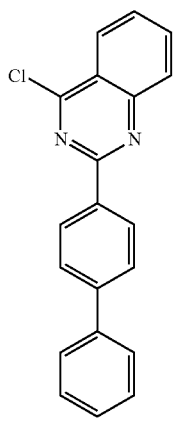
Sub 2-59

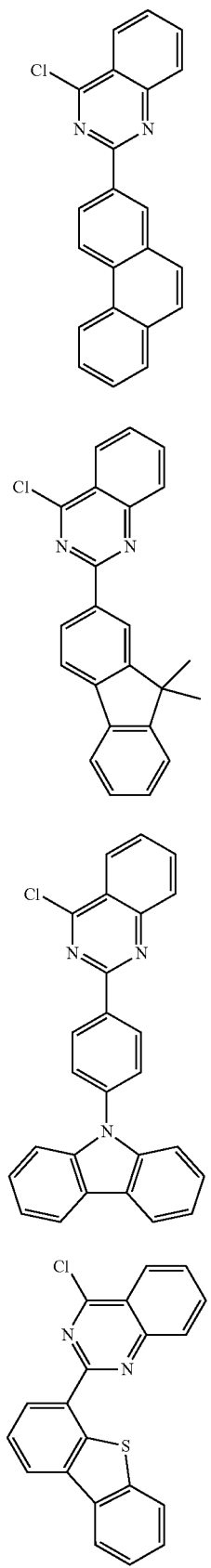
Sub 2-60
Sub 2-61
Sub 2-62
Sub 2-63
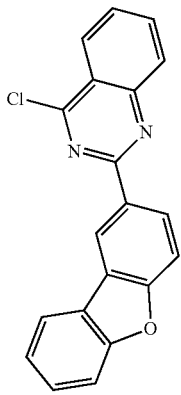
Sub 2-64
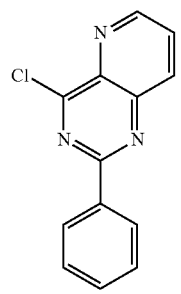
Sub 2-65
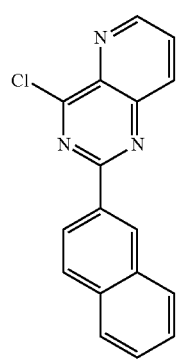
Sub 2-66
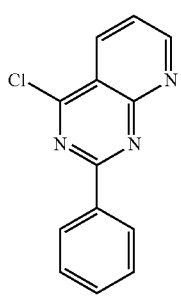
Sub 2-67
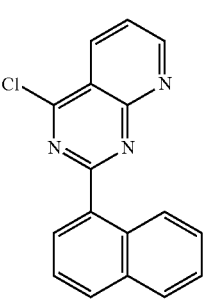
Sub 2-68

-continued

Sub 2-69
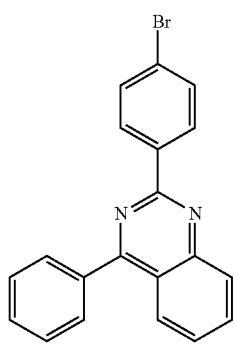

Sub 2-70
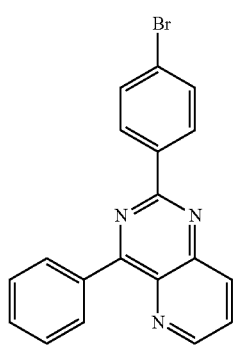

Sub 2-71
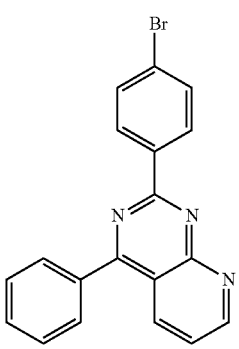

-continued

Sub 2-72
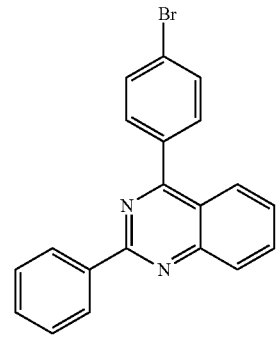

Sub 2-73
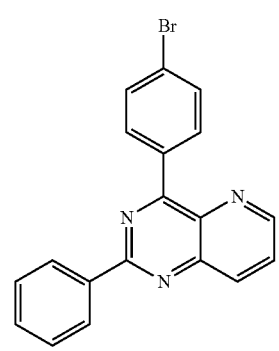

Sub 2-74
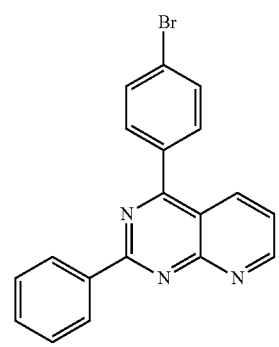

TABLE 2

| Compound | FD-MS | Compound | FD-MS |
|---|---|---|---|
| Sub 2-1 | m/z = 155.96($C_6H_5Br$ = 157.01) | Sub 2-2 | m/z = 160.99($C_6D_5Br$ = 162.04) |
| Sub 2-3 | m/z = 205.97($C_{10}H_7Br$ = 207.07) | Sub 2-4 | m/z = 205.97($C_{10}H_7Br$ = 207.07) |
| Sub 2-5 | m/z = 255.99($C_{14}H_9Br$ = 257.13) | Sub 2-6 | m/z = 231.99($C_{12}H_9Br$ = 233.10) |
| Sub 2-7 | m/z = 282.00($C_{16}H_{11}Br$ = 283.16) | Sub 2-8 | m/z = 308.02($C_{18}H_{13}Br$ = 309.20) |
| Sub 2-9 | m/z = 232.98($C_{11}H_8BrN$ = 234.09) | Sub 2-10 | m/z = 283.00($C_{15}H_{10}BrN$ = 284.15) |
| Sub 2-11 | m/z = 309.02($C_{17}H_{12}BrN$ = 310.19) | Sub 2-12 | m/z = 322.01($C_{17}H_{11}BrN_2$ = 323.19) |
| Sub 2-13 | m/z = 474.07($C_{29}H_{19}BrN_2$ = 475.38) | Sub 2-14 | m/z = 309.02($C_{17}H_{12}BrN$ = 310.19) |
| Sub 2-15 | m/z = 311.01($C_{15}H_{10}BrN_3$ = 312.16) | Sub 2-16 | m/z = 190.03($C_{10}H_7ClN_2$ = 190.63) |
| Sub 2-17 | m/z = 306.09($C_{19}H_{15}ClN_2$ = 306.79) | Sub 2-18 | m/z = 343.09($C_{21}H_{14}ClN_3$ = 343.81) |
| Sub 2-19 | m/z = 266.06($C_{16}H_{11}ClN_2$ = 266.72) | Sub 2-20 | m/z = 266.06($C_{16}H_{11}ClN_2$ = 266.72) |
| Sub 2-21 | m/z = 266.06($C_{16}H_{11}ClN_2$ = 266.72) | Sub 2-22 | m/z = 267.06($C_{15}H_{10}ClN_3$ = 267.71) |
| Sub 2-23 | m/z = 386.04($C_{22}H_{15}BrN_2$ = 387.27) | Sub 2-24 | m/z = 386.04($C_{22}H_{15}BrN_2$ = 387.27) |
| Sub 2-25 | m/z = 387.04($C_{21}H_{14}BrN_3$ = 388.26) | Sub 2-26 | m/z = 386.04($C_{22}H_{15}BrN_2$ = 387.27) |
| Sub 2-27 | m/z = 310.01($C_{16}H_{11}BrN_2$ = 311.18) | Sub 2-28 | m/z = 386.04($C_{22}H_{15}BrN_2$ = 387.27) |
| Sub 2-29 | m/z = 386.04($C_{22}H_{15}BrN_2$ = 387.27) | Sub 2-30 | m/z = 386.04($C_{22}H_{15}BrN_2$ = 387.27) |
| Sub 2-31 | m/z = 387.04($C_{21}H_{14}BrN_3$ = 388.26) | Sub 2-32 | m/z = 283.00($C_{15}H_{10}BrN$ = 284.15) |
| Sub 2-33 | m/z = 348.03($C_{19}H_{13}BrN_2$ = 349.22) | Sub 2-34 | m/z = 272.98($C_{13}H_8BrNO$ = 274.11) |
| Sub 2-35 | m/z = 271.99($C_{13}H_9BrN_2$ = 273.13) | Sub 2-36 | m/z = 323.03($C_{18}H_{14}BrN$ = 324.21) |
| Sub 2-37 | m/z = 321.02($C_{18}H_{12}BrN$ = 322.20) | Sub 2-38 | m/z = 399.06($C_{24}H_{18}BrN$ = 400.31) |
| Sub 2-39 | m/z = 397.05($C_{24}H_{16}BrN$ = 398.29) | Sub 2-40 | m/z = 397.05($C_{24}H_{16}BrN$ = 398.29) |
| Sub 2-41 | m/z = 636.12($C_{42}H_{25}BrN_2$ = 637.57) | Sub 2-42 | m/z = 439.09($C_{27}H_{22}BrN$ = 440.37) |
| Sub 2-43 | m/z = 261.95($C_{12}H_7BrS$ = 263.15) | Sub 2-44 | m/z = 245.97($C_{12}H_7BrO$ = 247.09) |
| Sub 2-45 | m/z = 240.05($C_{14}H_9ClN_2$ = 240.69) | Sub 2-46 | m/z = 290.06($C_{18}H_{11}ClN_2$ = 290.75) |

TABLE 2-continued

| Compound | FD-MS | Compound | FD-MS |
|---|---|---|---|
| Sub 2-47 | m/z = 316.08($C_{20}H_{13}ClN_2$ = 316.78) | Sub 2-48 | m/z = 316.08($C_{20}H_{13}ClN_2$ = 316.78) |
| Sub 2-49 | m/z = 356.11($C_{23}H_{17}ClN_2$ = 356.85) | Sub 2-50 | m/z = 330.06($C_{20}H_{11}ClN_2O$ = 330.77) |
| Sub 2-51 | m/z = 346.03($C_{20}H_{11}ClN_2S$ = 346.83) | Sub 2-52 | m/z = 405.10($C_{26}H_{16}ClN_3$ = 405.88) |
| Sub 2-53 | m/z = 241.04($C_{13}H_8ClN_3$ = 241.68) | Sub 2-54 | m/z = 317.07($C_{19}H_{12}ClN_3$ = 317.77) |
| Sub 2-55 | m/z = 241.04($C_{13}H_8ClN_3$ = 241.68) | Sub 2-56 | m/z = 291.06($C_{17}H_{10}ClN_3$ = 291.73) |
| Sub 2-57 | m/z = 240.05($C_{14}H_9ClN_2$ = 240.69) | Sub 2-58 | m/z = 290.06($C_{18}H_{11}ClN_2$ = 290.75) |
| Sub 2-59 | m/z = 316.08($C_{20}H_{13}ClN_2$ = 316.78) | Sub 2-60 | m/z = 340.08($C_{22}H_{13}ClN_2$ = 340.81) |
| Sub 2-61 | m/z = 356.11($C_{23}H_{17}ClN_2$ = 356.85) | Sub 2-62 | m/z = 405.10($C_{26}H_{16}ClN_3$ = 405.88) |
| Sub 2-63 | m/z = 346.03($C_{20}H_{11}ClN_2S$ = 346.83) | Sub 2-64 | m/z = 330.06($C_{20}H_{11}ClN_2O$ = 330.77) |
| Sub 2-65 | m/z = 241.04($C_{13}H_8ClN_3$ = 241.68) | Sub 2-66 | m/z = 291.06($C_{17}H_{10}ClN_3$ = 291.73) |
| Sub 2-67 | m/z = 241.04($C_{13}H_8ClN_3$ = 241.68) | Sub 2-68 | m/z = 291.06($C_{17}H_{10}ClN_3$ = 291.73) |
| Sub 2-69 | m/z = 360.03($C_{20}H_{13}BrN_2$ = 361.23) | Sub 2-70 | m/z = 361.02($C_{19}H_{12}BrN_3$ = 362.22) |
| Sub 2-71 | m/z = 361.02($C_{19}H_{12}BrN_3$ = 362.22) | Sub 2-72 | m/z = 360.03($C_{20}H_{13}BrN_2$ = 361.23) |
| Sub 2-73 | m/z = 361.02($C_{19}H_{12}BrN_3$ = 362.22) | Sub 2-74 | m/z = 361.02($C_{19}H_{12}BrN_3$ = 362.22) |

3. Synthesis Method of Product

To a solution of Sub 1 (1 eq.) in toluene in round bottom flask were added Sub 2 (1.2 eq.), $Pd_2(dba)_3$ (0.03 eq.), P(t-Bu)$_3$ (0.08 eq.), and NaOt-Bu (3 eq.) and stirred at 100° C. Upon completion of the reaction, the reaction solution was extracted with $CH_2Cl_2$ and water. The extract of organic layer was dried with $MgSO_4$ and concentrated, and then the produced organic material was purified by a silica gel column and recrystallization to obtain the final products.

(1) Synthesis Method of P-11

⟨Reaction Scheme 6⟩

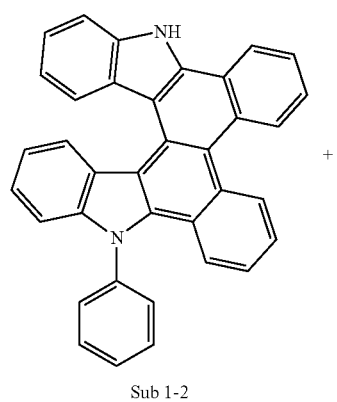

Sub 1-2

+

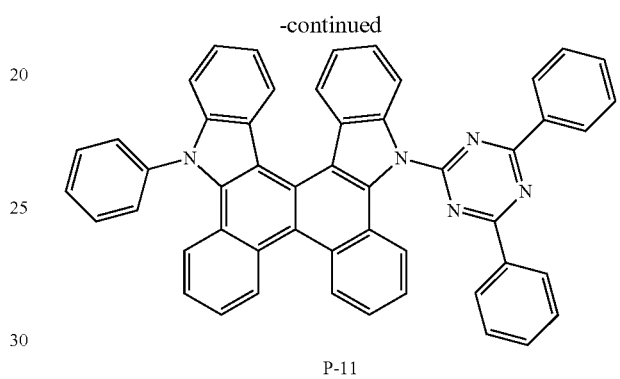

P-11

To a solution of the obtained Sub 1-2 (5.21 g, 10.8 mmol) in toluene in a round bottom flask were added Sub 2-22 (3.47 g, 13 mmol), $Pd_2(dba)_3$ (0.3 g, 0.3 mmol), 50% P(t-Bu)$_3$ (0.4 ml, 0.9 mmol), NaOt-Bu (3.11 g, 32.4 mmol) and stirred at 100° C. Upon completion of the reaction, the reaction solution was extracted with $CH_2Cl_2$ and water. The extract of organic layer was dried with $MgSO_4$ and concentrated, and then the produced organic material was purified by a silica gel column and recrystallization to obtain 6.32 g of the products (yield: 82%).

(2) Synthesis Method of P-22

⟨Reaction Scheme 7⟩

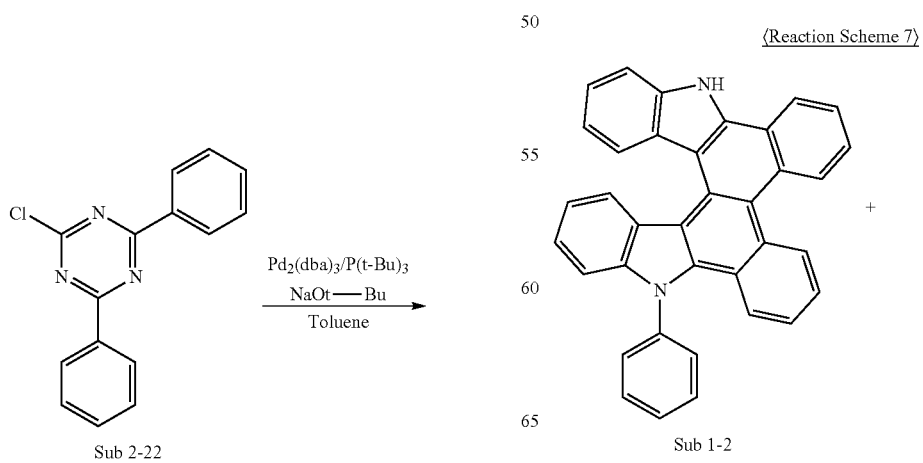

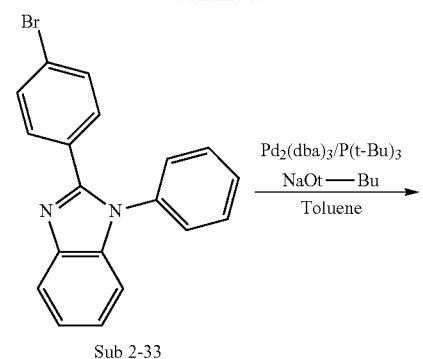

Sub 2-33

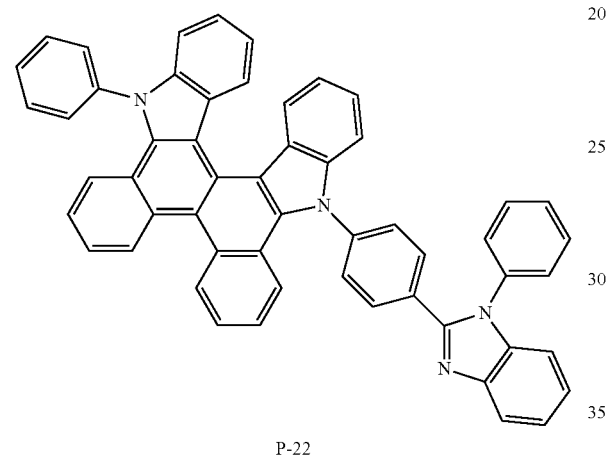

P-22

The obtained Sub 1-2 (5.92 g, 12.3 mmol), Sub 2-33 (5.14 g, 14.7 mmol), Pd$_2$(dba)$_3$ (0.34 g, 0.4 mmol), 50% P(t-Bu)$_3$ (0.5 ml, 1 mmol), NaOt-Bu (3.54 g, 36.8 mmol) and toluene were used to obtain 7.09 g of the product following the same synthesis method for P-11 (yield: 77%).

(3) Synthesis Method of P-42

⟨Reaction Scheme 8⟩

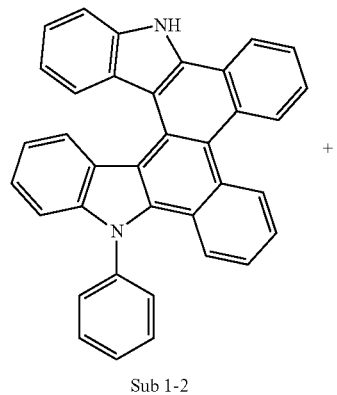

Sub 1-2

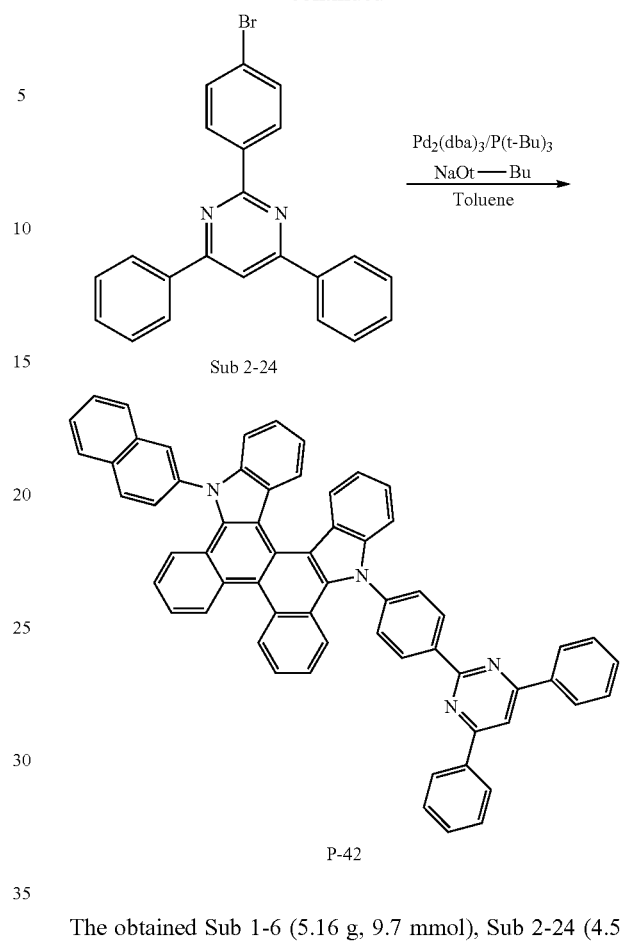

Sub 2-24

P-42

The obtained Sub 1-6 (5.16 g, 9.7 mmol), Sub 2-24 (4.5 g, 11.6 mmol), Pd$_2$(dba)$_3$ (0.27 g, 0.3 mmol), 50% P(t-Bu)$_3$ (0.4 ml, 0.8 mmol), NaOt-Bu (2.79 g, 29.1 mmol) and toluene were used to obtain 6.5 g of the product following the same synthesis method for P-11 (yield: 80%).

(4) Synthesis Method of P-45

⟨Reaction Scheme 9⟩

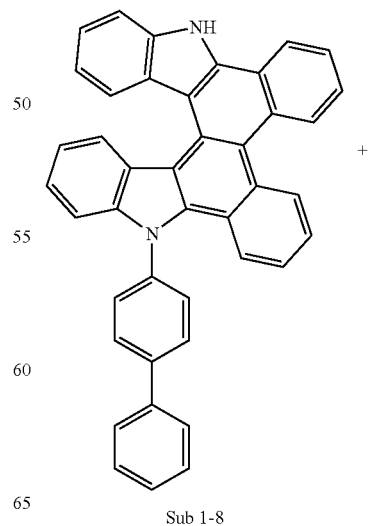

Sub 1-8

-continued

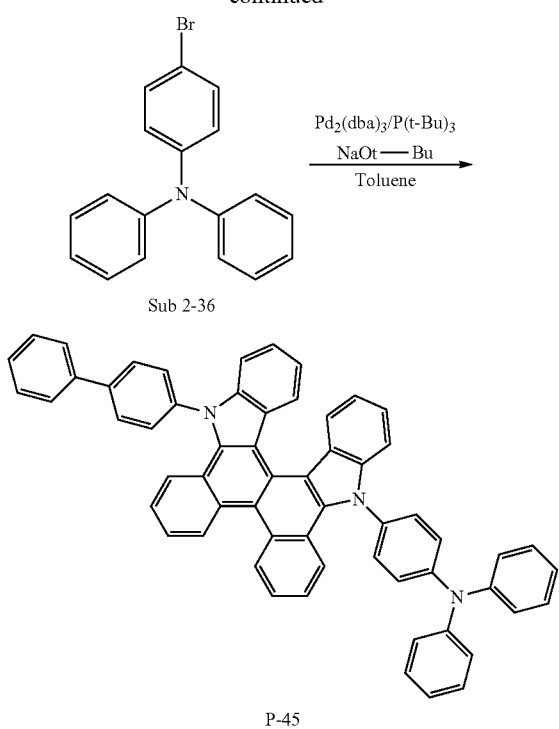

Sub 2-36

P-45

The obtained Sub 1-8 (5.74 g, 10.3 mmol), Sub 2-36 (4 g, 12.3 mmol), Pd₂(dba)₃ (0.28 g, 0.3 mmol), 50% P(t-Bu)₃ (0.4 ml, 0.8 mmol), NaOt-Bu (2.96 g, 30.8 mmol) and toluene were used to obtain 6.92 g of the product following the same synthesis method for P-11 (yield: 84%).

(5) Synthesis Method of P-61

⟨Reaction Scheme 10⟩

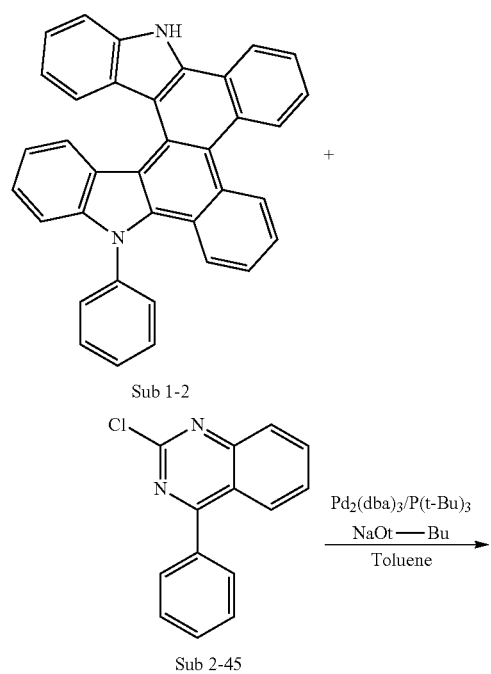

Sub 1-2

Sub 2-45

-continued

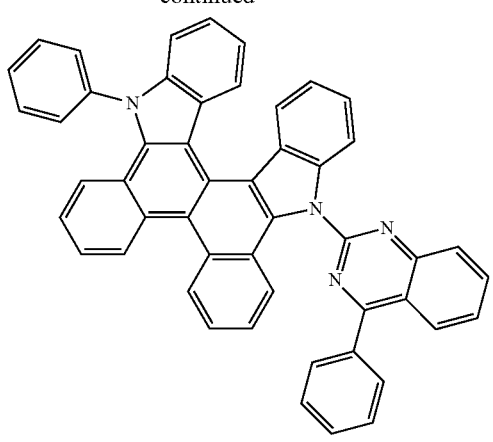

P-61

The obtained Sub 1-2 (5.48 g, 11.4 mmol), Sub 2-45 (3.28 g, 13.6 mmol), Pd₂(dba)₃ (0.31 g, 0.3 mmol), 50% P(t-Bu)₃ (0.4 ml, 0.9 mmol), NaOt-Bu (3.27 g, 34.1 mmol) and toluene were used obtain 5.69 g of the product following the same synthesis method for P-11 (yield: 73%).

(6) Synthesis Method of P-90

⟨Reaction Scheme 11⟩

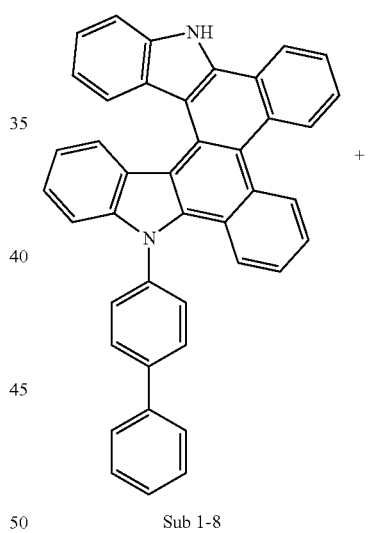

Sub 1-8

Sub 2-72

-continued

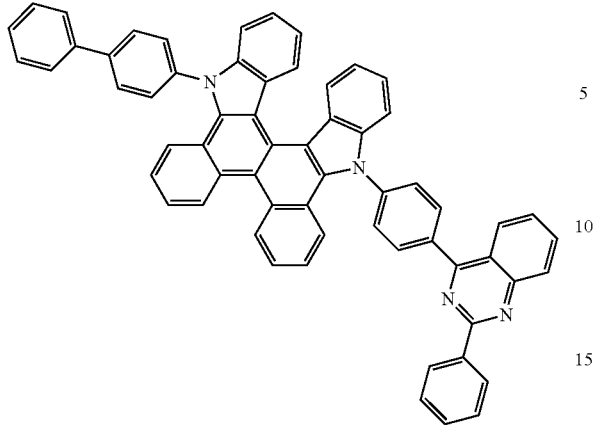

P-90

The obtained Sub 1-8 (5.23 g, 9.4 mmol), Sub 2-72 (4.06 g, 11.2 mmol), Pd$_2$(dba)$_3$ (0.26 g, 0.3 mmol), 50% P(t-Bu)$_3$ (0.4 ml, 0.7 mmol), NaOt-Bu (2.7 g, 28.1 mmol) and toluene were used to obtain 6.05 g of the product following the same synthesis method for P-11 (yield: 77%).

FD-MS data of the compounds P-1 to P-92 prepared in the Synthesis Examples of the present invention are given in Table 3 below.

TABLE 3

| Compound | FD-MS | Compound | FD-MS |
| --- | --- | --- | --- |
| P-1 | m/z = 558.21($C_{42}H_{26}N_2$ = 558.67) | P-2 | m/z = 608.23($C_{46}H_{28}N_2$ = 608.73) |
| P-3 | m/z = 613.26($C_{46}H_{23}D_5N_2$ = 613.76) | P-4 | m/z = 710.27($C_{54}H_{34}N_2$ = 710.86) |
| P-5 | m/z = 635.24($C_{47}H_{29}N_3$ = 635.75) | P-6 | m/z = 711.27($C_{53}H_{33}N_3$ = 711.85) |
| P-7 | m/z = 713.26($C_{51}H_{31}N_5$ = 713.83) | P-8 | m/z = 636.23($C_{46}H_{28}N_4$ = 636.74) |
| P-9 | m/z = 712.26($C_{52}H_{32}N_4$ = 712.84) | P-10 | m/z = 712.26($C_{52}H_{32}N_4$ = 712.84) |
| P-11 | m/z = 713.26($C_{51}H_{31}N_5$ = 713.83) | P-12 | m/z = 712.26($C_{52}H_{32}N4$ = 712.84) |
| P-13 | m/z = 788.29($C_{58}H_{36}N_4$ = 788.93) | P-14 | m/z = 788.29($C_{58}H_{36}N_4$ = 788.93) |
| P-15 | m/z = 789.29($C_{57}H_{35}N_5$ = 789.92) | P-16 | m/z = 788.29($C_{58}H_{36}N_4$ = 788.93) |
| P-17 | m/z = 788.29($C_{58}H_{36}N_4$ = 788.93) | P-18 | m/z = 788.29($C_{58}H_{36}N_4$ = 788.93) |
| P-19 | m/z = 789.29($C_{57}H_{35}N_5$ = 789.92) | P-20 | m/z = 788.29($C_{58}H_{36}N_4$ = 788.93) |
| P-21 | m/z = 685.25($C_{51}H_{31}N_3$ = 685.81) | P-22 | m/z = 750.28($C_{55}H_{34}N_4$ = 750.89) |
| P-23 | m/z = 675.23($C_{49}H_{29}N_3O$ = 675.77) | P-24 | m/z = 674.25($C_{49}H_{30}N_4$ = 674.79) |
| P-25 | m/z = 801.31($C_{60}H_{39}N_3$ = 801.97) | P-26 | m/z = 799.30($C_{60}H_{37}N_3$ = 799.96) |
| P-27 | m/z = 876.33($C_{65}H_{40}N_4$ = 877.04) | P-28 | m/z = 664.20($C_{48}H_{28}N_2S$ = 664.81) |
| P-29 | m/z = 634.24($C_{48}H_{30}N_2$ = 634.77) | P-30 | m/z = 708.26($C_{54}H_{32}N_2$ = 708.85) |
| P-31 | m/z = 698.27($C_{53}H_{34}N_2$ = 698.85) | P-32 | m/z = 662.27($C_{50}H_{34}N_2$ = 662.82) |
| P-33 | m/z = 735.27($C_{55}H_{33}N_3$ = 735.87) | P-34 | m/z = 752.29($C_{55}H_{36}N_4$ = 752.90) |
| P-35 | m/z = 828.33($C_{61}H_{40}N_4$ = 829.00) | P-36 | m/z = 839.30($C_{61}H_{37}N_5$ = 839.98) |
| P-37 | m/z = 762.28($C_{56}H_{34}N_4$ = 762.90) | P-38 | m/z = 664.26($C_{48}H_{32}N_4$ = 664.79) |
| P-39 | m/z = 829.32($C_{60}H_{39}N_5$ = 829.99) | P-40 | m/z = 788.29($C_{58}H_{36}N_4$ = 788.93) |
| P-41 | m/z = 888.33($C_{66}H_{40}N_4$ = 889.05) | P-42 | m/z = 838.31($C_{62}H_{38}N_4$ = 838.99) |
| P-43 | m/z = 865.32($C_{63}H_{39}N_5$ = 866.02) | P-44 | m/z = 789.29($C_{57}H_{35}N_5$ = 789.92) |
| P-45 | m/z = 801.31($C_{60}H_{39}N_3$ = 801.97) | P-46 | m/z = 891.36($C_{67}H_{45}N_3$ = 892.09) |
| P-47 | m/z = 761.28($C_{57}H_{35}N_3$ = 761.91) | P-48 | m/z = 724.25($C_{54}H_{32}N_2O$ = 724.84) |
| P-49 | m/z = 892.36($C_{66}H_{44}N_4$ = 893.08) | P-50 | m/z = 888.33($C_{66}H_{40}N_4$ = 889.05) |
| P-51 | m/z = 770.19($C_{54}H_{30}N_2S_2$ = 770.96) | P-52 | m/z = 1040.39($C_{78}H_{48}N_4$ = 1041.24) |
| P-53 | m/z = 866.32($C_{62}H_{38}N_6$ = 867.01) | P-54 | m/z = 866.32($C_{62}H_{38}N_6$ = 867.01) |
| P-55 | m/z = 942.35($C_{68}H_{42}N_6$ = 943.10) | P-56 | m/z = 942.35($C_{68}H_{42}N_6$ = 943.10) |
| P-57 | m/z = 1018.38($C_{74}H_{46}N_6$ = 1019.20) | P-58 | m/z = 1019.37($C_{73}H_{45}N_7$ = 1020.19) |
| P-59 | m/z = 942.35($C_{68}H_{42}N_6$ = 943.10) | P-60 | m/z = 1038.37($C_{78}H_{46}N_4$ = 1039.23) |
| P-61 | m/z = 686.25($C_{50}H_{30}N_4$ = 686.80) | P-62 | m/z = 762.28($C_{56}H_{34}N_4$ = 762.90) |
| P-63 | m/z = 786.28($C_{58}H_{34}N_4$ = 786.92) | P-64 | m/z = 812.29($C_{60}H_{36}N_4$ = 812.95) |
| P-65 | m/z = 878.34($C_{65}H_{42}N_4$ = 879.06) | P-66 | m/z = 776.26($C_{56}H_{32}N_4O$ = 776.88) |
| P-67 | m/z = 792.23($C_{56}H_{32}N_4S$ = 792.95) | P-68 | m/z = 851.30($C_{62}H_{37}N_5$ = 851.99) |
| P-69 | m/z = 687.24($C_{49}H_{29}N_5$ = 687.79) | P-70 | m/z = 687.24($C_{49}H_{29}N_5$ = 687.79) |
| P-71 | m/z = 763.27($C_{55}H_{33}N_5$ = 763.88) | P-72 | m/z = 737.26($C_{53}H_{31}N_5$ = 737.85) |
| P-73 | m/z = 686.25($C_{50}H_{30}N_4$ = 686.80) | P-74 | m/z = 812.29($C_{60}H_{36}N_4$ = 812.95) |
| P-75 | m/z = 736.26($C_{54}H_{32}N_2$ = 736.86) | P-76 | m/z = 738.28($C_{54}H_{34}N_4$ = 738.87) |
| P-77 | m/z = 802.31($C_{59}H_{38}N_4$ = 802.96) | P-78 | m/z = 792.23($C_{56}H_{32}N_4S$ = 792.95) |
| P-79 | m/z = 776.26($C_{56}H_{32}N_4O$ = 776.88) | P-80 | m/z = 901.32($C_{66}H_{39}N_5$ = 902.05) |
| P-81 | m/z = 687.24($C_{49}H_{29}N_5$ = 687.79) | P-82 | m/z = 763.27($C_{55}H_{33}N_5$ = 763.88) |
| P-83 | m/z = 737.26($C_{53}H_{31}N_5$ = 737.85) | P-84 | m/z = 737.26($C_{53}H_{31}N_5$ = 737.85) |
| P-85 | m/z = 762.28($C_{56}H_{34}N_4$ = 762.90) | P-86 | m/z = 838.31($C_{62}H_{38}N_4$ = 838.99) |

TABLE 3-continued

| Compound | FD-MS | Compound | FD-MS |
|---|---|---|---|
| P-87 | m/z = 763.27($C_{55}H_{33}N_5$ = 763.88) | P-88 | m/z = 763.27($C_{55}H_{33}N_5$ = 763.88) |
| P-89 | m/z = 762.28($C_{56}H_{34}N_4$ = 762.90) | P-90 | m/z = 838.31($C_{62}H_{38}N_4$ = 838.99) |
| P-91 | m/z = 763.27($C_{55}H_{33}N_5$ = 763.88) | P-92 | m/z = 763.27($C_{55}H_{33}N_5$ = 763.88) |

Illustrative synthesis methods for the present invention as represented by Formula 1, as explained herein above, are all based on the Buchwald-Hartwig cross coupling reaction, Intramolecular C—C bond formation ($S_N1$) reaction (*J. Org. Chem.* 2009, 74, 4490) and Ullman reaction. So, a person skilled in the relevant field of technology would easily understand that the above reactions can be applied to the compounds of Formula 1 having other substituents ($L_1$, $L_2$, $Ar_1$, $Ar_2$ and so on) than those specifically described in the reactions.

For example, in the reaction 2, the reaction of Sub 1-I to Sub 1-II is based on the Intramolecular C—C bond formation ($S_N1$) reaction, the reaction of Sub 1-II to Sub 1 is based on the Ullmann reaction, and the reaction from starting material to Sub 1-I and the synthesis method for products (reaction 6 to reaction 11) are based on the Buchwald-Hartwig cross coupling reaction. Therefore, these reactions can be applied to other compounds of Formula 1 having different substituents than those specifically described in the reactions.

Fabrication and Evaluation of Organic Electronic Element

[Example 1] Green Organic Light Emitting Diode (a Phosphorescent Host)

Organic light emitting diodes (OLEDs) were fabricated according to a conventional method by using a compound (one of the compounds P-1 to P-60) of the present invention as a phosphorescent host material.

First, an ITO layer (anode) was formed on a glass substrate, and a film of 4,4',4"-tris[N-(2-naphthyl)-N-phenylamino]-triphenylamine (hereinafter abbreviated as "2-TNATA") was vacuum-deposited on the ITO layer to form a hole injection layer with a thickness of 60 nm. Subsequently, 4,4-bis[N-(1-naphthyl)-N-phenylamino]biphenyl (hereinafter abbreviated as "NPD") was vacuum-deposited with a thickness of 60 nm on the hole injection layer to form a hole transport layer. Subsequently, a light emitting layer with a thickness of 30 nm was deposited on the hole transport layer by doping the hole transport layer with the compound P-1 of the present invention as a host material and tris(2-phenylpyridine)-iridium (hereinafter abbreviated as "Ir(ppy)$_3$") as a dopant material in a weight ratio of 95:5. Next, a film of ((1,1'-bisphenyl)-4-olato)bis(2-methyl-8-quinolinolato)aluminum (hereinafter abbreviated as "BAlq") was vacuum-deposited with a thickness of 10 nm on the light emitting layer to form a hole blocking layer, and a film of tris(8-quinolinolato)aluminum (hereinafter abbreviated as "Alq$_3$") was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 60] Green Organic Light Emitting Diode (a Phosphorescent Host)

The OLED was manufactured in the same manner as described in Example 1, except that any one of the compounds P-2 to P-60 of the present invention in the Table 4 below was used as the host material of the a light emitting layer, instead of the inventive compound P-1.

Comparative Example 1

An OLED was manufactured in the same manner as described in Example 1, except that Comparative Compound 1 represented below was used as the host material of the a light emitting layer, instead of the inventive compound P-1.

⟨Comparative Compound 1⟩

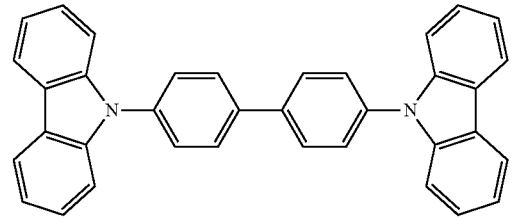

Comparative Example 2

An OLED was manufactured in the same manner as described in Example 1, except that Comparative Compound 2 represented below was used as the host material of the a light emitting layer, instead of the inventive compound P-1.

⟨Comparative Compound 2⟩

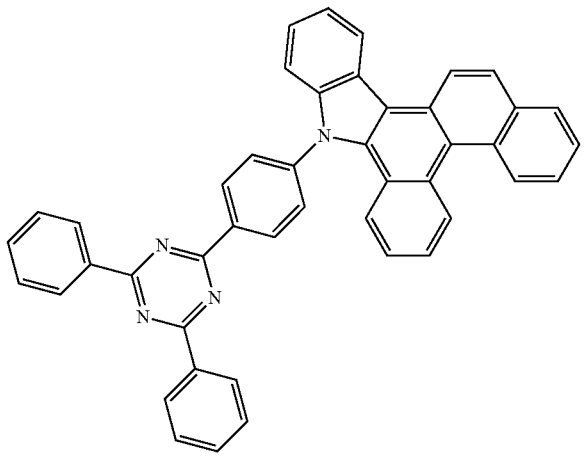

Comparative Example 3

An OLED was manufactured in the same manner as described in Example 1, except that Comparative Compound 3 represented below was used as the host material of the a light emitting layer, instead of the inventive compound P-1.

⟨Comparative Compound 3⟩

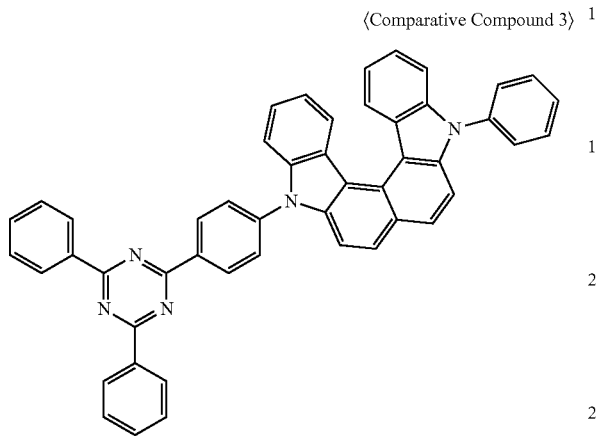

A forward bias DC voltage was applied to each of the OLEDs manufactured through the Examples 1 to 60 and Comparative Example 1 to 3, and electro-luminescence (EL) characteristics of the OLED were measured by PR-650 (Photoresearch). Also, T90 life span was measured by life span measuring equipment (Mcscience) at reference brightness of 300 cd/m². Table 4 below shows evaluation results.

TABLE 4

| | Compound | Voltage (V) | Current Density (mA/cm²) | Brightness (cd/m²) | Efficiency (cd/A) | Life time T(90) | CIE x | CIE y |
|---|---|---|---|---|---|---|---|---|
| Com. Ex (1) | Com. Com 1 | 6.5 | 7.9 | 300.0 | 3.8 | 60.5 | 0.33 | 0.61 |
| Com. Ex (2) | Com. Com 2 | 5.9 | 6.0 | 300.0 | 5.0 | 69.6 | 0.32 | 0.60 |
| Com. Ex (3) | Com. Com 3 | 5.7 | 5.5 | 300.0 | 5.5 | 80.9 | 0.32 | 0.61 |
| Ex. (1) | Com. (P-1) | 5.3 | 4.4 | 300.0 | 6.8 | 128.8 | 0.32 | 0.61 |
| Ex. (2) | Com. (P-2) | 5.3 | 4.4 | 300.0 | 6.8 | 119.7 | 0.33 | 0.61 |
| Ex. (3) | Com. (P-3) | 5.5 | 4.3 | 300.0 | 6.9 | 126.7 | 0.32 | 0.60 |
| Ex. (4) | Com. (P-4) | 5.3 | 4.5 | 300.0 | 6.6 | 118.5 | 0.33 | 0.61 |
| Ex. (5) | Com. (P-5) | 5.4 | 4.3 | 300.0 | 6.9 | 122.7 | 0.32 | 0.60 |
| Ex. (6) | Com. (P-6) | 5.5 | 4.5 | 300.0 | 6.7 | 129.0 | 0.32 | 0.61 |
| Ex. (7) | Com. (P-7) | 5.3 | 4.5 | 300.0 | 6.7 | 117.5 | 0.32 | 0.60 |
| Ex. (8) | Com. (P-8) | 5.4 | 4.6 | 300.0 | 6.6 | 121.7 | 0.33 | 0.60 |
| Ex. (9) | Com. (P-9) | 5.5 | 4.3 | 300.0 | 7.0 | 129.9 | 0.33 | 0.61 |
| Ex. (10) | Com. (P-10) | 5.5 | 4.4 | 300.0 | 6.9 | 128.0 | 0.33 | 0.60 |
| Ex. (11) | Com. (P-11) | 5.4 | 4.6 | 300.0 | 6.5 | 125.4 | 0.33 | 0.60 |
| Ex. (12) | Com. (P-12) | 5.4 | 4.6 | 300.0 | 6.6 | 125.2 | 0.32 | 0.61 |
| Ex. (13) | Com. (P-13) | 5.2 | 4.1 | 300.0 | 7.3 | 132.6 | 0.33 | 0.60 |
| Ex. (14) | Com. (P-14) | 5.2 | 4.2 | 300.0 | 7.1 | 139.2 | 0.33 | 0.61 |
| Ex. (15) | Com. (P-15) | 5.2 | 4.1 | 300.0 | 7.4 | 137.1 | 0.33 | 0.60 |
| Ex. (16) | Com. (P-16) | 5.3 | 4.0 | 300.0 | 7.5 | 151.2 | 0.33 | 0.61 |
| Ex. (17) | Com. (P-17) | 5.3 | 4.3 | 300.0 | 7.0 | 116.4 | 0.33 | 0.60 |
| Ex. (18) | Com. (P-18) | 5.5 | 4.4 | 300.0 | 6.8 | 119.3 | 0.33 | 0.61 |
| Ex. (19) | Com. (P-19) | 5.4 | 4.5 | 300.0 | 6.7 | 121.0 | 0.33 | 0.60 |
| Ex. (20) | Com. (P-20) | 5.4 | 4.3 | 300.0 | 7.0 | 122.7 | 0.33 | 0.61 |
| Ex. (21) | Com. (P-21) | 5.4 | 4.5 | 300.0 | 6.6 | 123.2 | 0.33 | 0.61 |
| Ex. (22) | Com. (P-22) | 5.5 | 4.4 | 300.0 | 6.9 | 127.6 | 0.33 | 0.60 |

TABLE 4-continued

| | Compound | Voltage (V) | Current Density (mA/cm²) | Brightness (cd/m²) | Efficiency (cd/A) | Life time T(90) | CIE x | CIE y |
|---|---|---|---|---|---|---|---|---|
| Ex. (23) | Com. (P-23) | 5.5 | 4.4 | 300.0 | 6.8 | 123.9 | 0.33 | 0.61 |
| Ex. (24) | Com. (P-24) | 5.4 | 4.4 | 300.0 | 6.7 | 116.1 | 0.32 | 0.61 |
| Ex. (25) | Com. (P-25) | 5.3 | 4.6 | 300.0 | 6.5 | 118.4 | 0.33 | 0.61 |
| Ex. (26) | Com. (P-26) | 5.4 | 4.5 | 300.0 | 6.6 | 124.0 | 0.32 | 0.60 |
| Ex. (27) | Com. (P-27) | 5.4 | 4.5 | 300.0 | 6.6 | 126.6 | 0.32 | 0.61 |
| Ex. (28) | Com. (P-28) | 5.3 | 4.3 | 300.0 | 6.9 | 122.7 | 0.33 | 0.60 |
| Ex. (29) | Com. (P-29) | 5.5 | 4.4 | 300.0 | 6.9 | 118.5 | 0.33 | 0.60 |
| Ex. (30) | Com. (P-30) | 5.3 | 4.4 | 300.0 | 6.8 | 119.5 | 0.33 | 0.60 |
| Ex. (31) | Com. (P-31) | 5.6 | 4.8 | 300.0 | 6.3 | 95.4 | 0.32 | 0.60 |
| Ex. (32) | Com. (P-32) | 5.6 | 4.5 | 300.0 | 6.6 | 102.7 | 0.33 | 0.61 |
| Ex. (33) | Com. (P-33) | 5.4 | 4.6 | 300.0 | 6.6 | 126.9 | 0.32 | 0.61 |
| Ex. (34) | Com. (P-34) | 5.5 | 4.6 | 300.0 | 6.6 | 96.3 | 0.32 | 0.61 |
| Ex. (35) | Com. (P-35) | 5.3 | 4.5 | 300.0 | 6.6 | 129.0 | 0.33 | 0.60 |
| Ex. (36) | Com. (P-36) | 5.3 | 4.5 | 300.0 | 6.6 | 122.7 | 0.32 | 0.61 |
| Ex. (37) | Com. (P-37) | 5.4 | 4.6 | 300.0 | 6.5 | 128.1 | 0.32 | 0.60 |
| Ex. (38) | Com. (P-38) | 5.6 | 4.8 | 300.0 | 6.3 | 111.6 | 0.32 | 0.60 |
| Ex. (39) | Com. (P-39) | 5.4 | 4.5 | 300.0 | 6.6 | 119.0 | 0.33 | 0.60 |
| Ex. (40) | Com. (P-40) | 5.5 | 4.5 | 300.0 | 6.6 | 126.0 | 0.32 | 0.61 |
| Ex. (41) | Com. (P-41) | 5.2 | 4.1 | 300.0 | 7.2 | 132.3 | 0.33 | 0.61 |
| Ex. (42) | Com. (P-42) | 5.2 | 4.1 | 300.0 | 7.3 | 135.8 | 0.33 | 0.60 |
| Ex. (43) | Com. (P-43) | 5.2 | 4.2 | 300.0 | 7.2 | 135.3 | 0.33 | 0.61 |
| Ex. (44) | Com. (P-44) | 5.5 | 4.5 | 300.0 | 6.6 | 127.5 | 0.32 | 0.60 |
| Ex. (45) | Com. (P-45) | 5.4 | 4.3 | 300.0 | 7.0 | 127.0 | 0.32 | 0.61 |
| Ex. (46) | Com. (P-46) | 5.5 | 4.6 | 300.0 | 6.6 | 129.8 | 0.32 | 0.60 |
| Ex. (47) | Com. (P-47) | 5.4 | 4.4 | 300.0 | 6.8 | 125.7 | 0.33 | 0.61 |
| Ex. (48) | Com. (P-48) | 5.5 | 4.4 | 300.0 | 6.8 | 116.0 | 0.32 | 0.61 |
| Ex. (49) | Com. (P-49) | 5.6 | 4.8 | 300.0 | 6.3 | 114.6 | 0.32 | 0.61 |
| Ex. (50) | Com. (P-50) | 5.5 | 4.6 | 300.0 | 6.6 | 106.6 | 0.32 | 0.60 |
| Ex. (51) | Com. (P-51) | 5.4 | 4.8 | 300.0 | 6.3 | 109.7 | 0.32 | 0.60 |
| Ex. (52) | Com. (P-52) | 5.7 | 4.8 | 300.0 | 6.3 | 110.4 | 0.33 | 0.61 |
| Ex. (53) | Com. (P-53) | 5.5 | 4.7 | 300.0 | 6.3 | 107.0 | 0.32 | 0.61 |
| Ex. (54) | Com. (P-54) | 5.6 | 4.6 | 300.0 | 6.5 | 96.0 | 0.32 | 0.61 |
| Ex. (55) | Com. (P-55) | 5.5 | 4.7 | 300.0 | 6.3 | 101.5 | 0.32 | 0.60 |
| Ex. (56) | Com. (P-56) | 5.5 | 4.6 | 300.0 | 6.5 | 114.3 | 0.32 | 0.61 |
| Ex. (57) | Com. (P-57) | 5.7 | 4.7 | 300.0 | 6.4 | 103.6 | 0.32 | 0.61 |
| Ex. (58) | Com. (P-58) | 5.6 | 4.6 | 300.0 | 6.5 | 112.7 | 0.32 | 0.61 |
| Ex. (59) | Com. (P-59) | 5.5 | 4.7 | 300.0 | 6.4 | 97.7 | 0.33 | 0.61 |
| Ex. (60) | Com. (P-60) | 5.6 | 4.8 | 300.0 | 6.3 | 114.8 | 0.33 | 0.61 |

[Example 61] Red Organic Light Emitting Diode (a Phosphorescent Host)

Organic light emitting diodes (OLEDs) were fabricated according to a conventional method by using a compound (one of the compounds P-61 to P-92) of the present invention as a phosphorescent host material.

First, an ITO layer (anode) was formed on a glass substrate, and a film of 2-TNATA was vacuum-deposited on the ITO layer to form a hole injection layer with a thickness of 60 nm. Subsequently, NPD was vacuum-deposited with a thickness of 60 nm on the hole injection layer to form a hole transport layer. Subsequently, a light emitting layer with a thickness of 30 nm was deposited on the hole transport layer by doping the hole transport layer with the compound P-61 of the present invention as a host material and bis-(1-phenylisoquinolyl)iridium(III)acetylacetonate (hereinafter abbreviated as "(piq)$_2$Ir(acac)") as a dopant material in a weight ratio of 95:5. Next, a film of BAlq was vacuum-deposited with a thickness of 10 nm on the light emitting layer to form a hole blocking layer, and a film of Alq$_3$ was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 62] to [Example 92] Red Organic Light Emitting Diode (a Phosphorescent Host)

The OLED was manufactured in the same manner as described in Example 61, except that any one of the compounds P-62 to P-92 of the present invention in the Table 5 below was used as the host material of the a light emitting layer, instead of the inventive compound P-61.

Comparative Example 4

An OLED was manufactured in the same manner as described in Example 61, except that the above Comparative Compound 1 was used as the host material of the a light emitting layer, instead of the inventive compound P-61.

Comparative Example 5

An OLED was manufactured in the same manner as described in Example 61, except that the following Comparative Compound 4 was used as the host material of the a light emitting layer, instead of the inventive compound P-61.

⟨Comparative Compound 4⟩

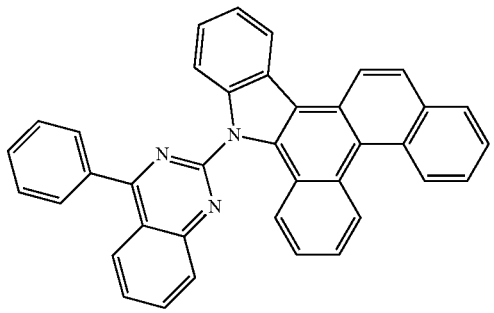

Comparative Example 6

An OLED was manufactured in the same manner as described in Example 61, except that the following Comparative Compound 5 was used as the host material of the a light emitting layer, instead of the inventive compound P-61.

⟨Comparative Compound 5⟩

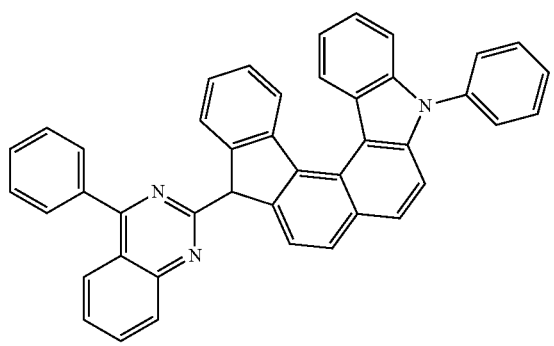

A forward bias DC voltage was applied to each of the OLEDs manufactured through the Examples 61 to 92 and Comparative Examples 4 to 6, and electro-luminescence (EL) characteristics of the OLED were measured by PR-650 (Photoresearch). Also, T90 life span was measured by life span measuring equipment (Mcscience) at a reference brightness of 300 cd/$m^2$. Table 5 below shows evaluation results.

TABLE 5

| | Compound | Voltage (V) | Current Density (mA/$cm^2$) | Brightness (cd/$m^2$) | Efficiency (cd/A) | Life time T(90) | CIE x | CIE y |
|---|---|---|---|---|---|---|---|---|
| com. Ex(4) | Com. Com 1 | 6.1 | 6.0 | 300.0 | 5.0 | 57.1 | 0.66 | 0.32 |
| com. Ex(5) | Com. Com 4 | 5.9 | 5.5 | 300.0 | 5.5 | 71.6 | 0.66 | 0.33 |
| com. Ex(6) | Com. Com 5 | 5.6 | 5.1 | 300.0 | 5.9 | 86.5 | 0.66 | 0.32 |
| Ex. (61) | Com. (P-61) | 4.6 | 3.7 | 300.0 | 8.2 | 152.5 | 0.66 | 0.32 |
| Ex. (62) | Com. (P-62) | 4.6 | 3.7 | 300.0 | 8.1 | 147.0 | 0.66 | 0.32 |
| Ex. (63) | Com. (P-63) | 5.1 | 4.1 | 300.0 | 7.4 | 132.5 | 0.66 | 0.33 |
| Ex. (64) | Com. (P-64) | 4.9 | 4.2 | 300.0 | 7.1 | 123.7 | 0.66 | 0.32 |
| Ex. (65) | Com. (P-65) | 5.0 | 4.2 | 300.0 | 7.2 | 137.2 | 0.66 | 0.32 |
| Ex. (66) | Com. (P-66) | 5.0 | 3.9 | 300.0 | 7.6 | 135.0 | 0.66 | 0.32 |
| Ex. (67) | Com. (P-67) | 5.1 | 4.1 | 300.0 | 7.3 | 139.9 | 0.66 | 0.33 |
| Ex. (68) | Com. (P-68) | 5.0 | 4.0 | 300.0 | 7.4 | 128.8 | 0.66 | 0.32 |
| Ex. (69) | Com. (P-69) | 4.9 | 4.1 | 300.0 | 7.3 | 135.1 | 0.66 | 0.33 |
| Ex. (70) | Com. (P-70) | 4.9 | 4.1 | 300.0 | 7.3 | 136.3 | 0.66 | 0.32 |
| Ex. (71) | Com. (P-71) | 5.1 | 4.0 | 300.0 | 7.5 | 132.7 | 0.66 | 0.33 |
| Ex. (72) | Com. (P-72) | 5.1 | 4.1 | 300.0 | 7.4 | 128.6 | 0.66 | 0.32 |
| Ex. (73) | Com. (P-73) | 4.7 | 3.9 | 300.0 | 7.7 | 148.5 | 0.66 | 0.32 |
| Ex. (74) | Com. (P-74) | 4.7 | 3.9 | 300.0 | 7.8 | 149.7 | 0.66 | 0.33 |
| Ex. (75) | Com. (P-75) | 5.1 | 4.1 | 300.0 | 7.2 | 128.6 | 0.66 | 0.32 |
| Ex. (76) | Com. (P-76) | 5.0 | 4.1 | 300.0 | 7.3 | 136.6 | 0.66 | 0.33 |
| Ex. (77) | Com. (P-77) | 5.0 | 4.1 | 300.0 | 7.3 | 137.6 | 0.66 | 0.33 |
| Ex. (78) | Com. (P-78) | 5.0 | 4.1 | 300.0 | 7.4 | 132.3 | 0.66 | 0.32 |
| Ex. (79) | Com. (P-79) | 4.9 | 4.0 | 300.0 | 7.5 | 136.0 | 0.66 | 0.33 |
| Ex. (80) | Com. (P-80) | 5.0 | 4.1 | 300.0 | 7.4 | 134.5 | 0.66 | 0.32 |
| Ex. (81) | Com. (P-81) | 5.4 | 4.5 | 300.0 | 6.7 | 116.9 | 0.67 | 0.33 |
| Ex. (82) | Com. (P-82) | 5.3 | 4.4 | 300.0 | 6.8 | 114.8 | 0.66 | 0.32 |
| Ex. (83) | Com. (P-83) | 5.3 | 4.4 | 300.0 | 6.8 | 113.7 | 0.66 | 0.33 |
| Ex. (84) | Com. (P-84) | 5.3 | 4.4 | 300.0 | 6.8 | 114.5 | 0.66 | 0.33 |
| Ex. (85) | Com. (P-85) | 5.3 | 4.3 | 300.0 | 7.0 | 106.4 | 0.66 | 0.32 |
| Ex. (86) | Com. (P-86) | 5.3 | 4.4 | 300.0 | 6.8 | 109.2 | 0.66 | 0.33 |
| Ex. (87) | Com. (P-87) | 5.2 | 4.3 | 300.0 | 7.0 | 103.1 | 0.66 | 0.33 |
| Ex. (88) | Com. (P-88) | 5.1 | 4.4 | 300.0 | 6.9 | 102.9 | 0.66 | 0.33 |
| Ex. (89) | Com. (P-89) | 5.2 | 4.4 | 300.0 | 6.8 | 112.4 | 0.66 | 0.33 |
| Ex. (90) | Com. (P-90) | 5.4 | 4.2 | 300.0 | 7.1 | 104.1 | 0.66 | 0.32 |
| Ex. (91) | Com. (P-91) | 5.3 | 4.2 | 300.0 | 7.2 | 104.8 | 0.66 | 0.33 |
| Ex. (92) | Com. (P-92) | 5.3 | 4.3 | 300.0 | 6.9 | 116.4 | 0.66 | 0.32 |

Referring to table 4 and table 5, the Comparative examples 1 and 4 using the comparative compound 1(CBP) as a host material of emitting layer, the Comparative examples 2 and 5 using the comparative compounds 2 and 4 that are a form fused with a naphthyl group and a phenyl group to a carbazole backbone, the Comparative examples 3 and 6 using the comparative compounds 3 and 5 that are a form fused with other carbazole to a carbazole backbone, and the examples 1 to 92 using the compounds of the present invention that are a form fused of two benzocarbazoles, show the results as in the following.

The results of the comparative example 1 using the comparative compound 1(CBP), and the comparative example 2 and the comparative example 4 using the compound that was fused with a simple aryl group to a carbazole, have been showed high driving voltage, low light emitting efficiency and low lifespan. But the results of the comparative example 3 and 5 using the compound that is a form fused of two carbazoles, have been improved a little as driving voltage, light emitting efficiency and lifespan than the comparative examples 2 and 4. However, the excellent properties that have significant effects to the device are not shown.

On the other hands, the compounds of the present invention that are a form fused of two benzocarbazoles show a reduced driving voltage, a predominately increased light emitting efficiency and lifespan compared with the comparative examples 1 to 5.

The reason can be predicted that the core of the compound of present invention which is a form fused two benzocarbazoles, has deep HOMO energy level, therefore a charge balance between a hole and an electron could be achieved, which light emitting in a emitting layer is made more efficiently, and finally light emitting efficiency and lifespan could be increased. Also, thermal damage due to low driving voltage is reduced and high Tg value due to high molecular weight is contributed to improve a lifespan.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound represented by Formula 1 below:

[Formula 1]

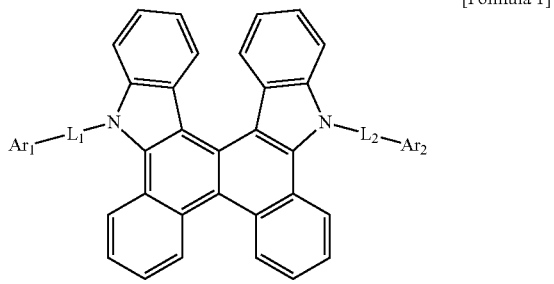

wherein,
Ar$_1$ and Ar$_2$ are independently selected from the group consisting of a C$_6$-C$_{60}$ aryl group, a fluorenyl group, a C$_2$-C$_{60}$ heterocyclic group containing at least one heteroatom selected from the group consisting of O, N, S, Si, and P, a C$_1$-C$_{50}$ alkyl group, a C$_2$-C$_{20}$ alkenyl group, a C$_1$-C$_{30}$ alkoxy group, a C$_6$-C$_{60}$ aryloxy group, C$_3$-C$_{60}$ cycloalkyl group, and —N(R')(R"),
wherein, R' and R" are independently selected from the group consisting of a C$_6$-C$_{60}$ aryl group, a fluorenyl group, and a C$_2$-C$_{60}$ heterocyclic group containing at least one heteroatom selected from the group consisting of O, N, S, Si, and P,
L$_1$ and L$_2$ are independently selected from the group consisting of a single bond, a C$_6$-C$_{60}$ arylene group, a fluorenylene group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, and a bivalent aliphatic hydro carbon, with the proviso that, the arylene group, the fluorenylene group, the heterocyclic group, the fused ring group and the aliphatic hydrocarbon group are optionally substituted by one or more substituents selected from the group consisting of a nitro group, a nitrile group, halogen group, a C$_1$-C$_{20}$ alkyl group, a C$_6$-C$_{20}$ aryl group, a C$_2$-C$_{20}$ heterocyclic group, a C$_1$-C$_{20}$ alkoxy group, and amino group, and with the proviso that the aryl group, fluorenyl group, heterocyclic group, alkyl group, cycloalkyl group, alkenyl group and aryloxy group are optionally substituted by one or more substituents selected from the group consisting of deuterium, halogen, a silane group, a siloxane group, a boron group, a germanium group, a cyano group, a nitro group, a C$_1$-C$_{20}$ alkylthio group, a C$_1$-C$_{20}$ alkoxy group, a C$_1$-C$_{20}$ alkyl group, a C$_2$-C$_{20}$ alkenyl group, a C$_2$-C$_{20}$ alkynyl group, a C$_6$-C$_{20}$ aryl group, a C$_6$-C$_{20}$ aryl group substituted by deuterium, a C$_2$-C$_{20}$ heterocyclic group, a C$_3$-C$_{20}$ cycloalkyl group, a C$_7$-C$_{20}$ arylalkyl group, and a C$_8$-C$_{20}$ arylalkenyl group.

2. The compound as claimed in claim 1, wherein the compound is represented by one of Formulas below:

[Formula 2]

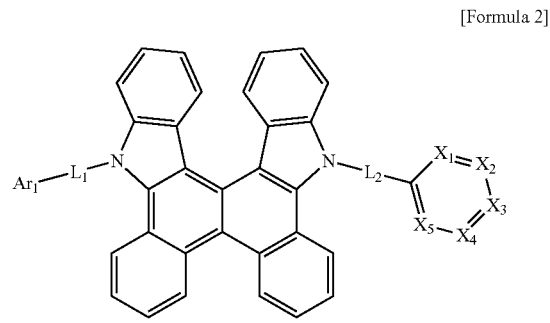

[Formula 3]

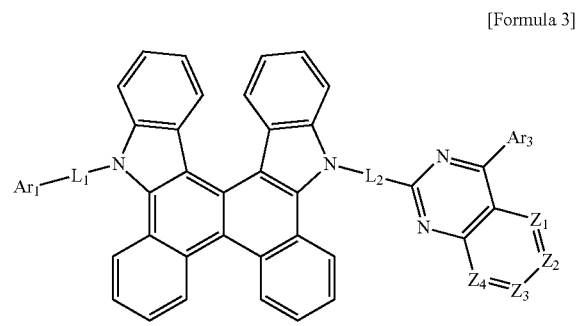

[Formula 4]

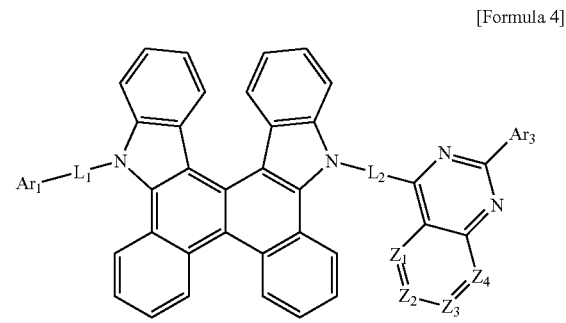

wherein,

Ar$_1$, L$_1$ and L$_2$ are as defined in claim 1,

Ar$_3$ is selected from the group consisting of a C$_6$-C$_{60}$ aryl group, a C$_2$-C$_{20}$ alkenyl group, a C$_2$-C$_{60}$ heterocyclic group containing at least one heteroatom selected from the group consisting of O, N, S, Si, and P, a C$_1$-C$_{50}$ alkyl group, and a fluorenyl group, X$_1$ to X$_5$ and Z$_1$ to Z$_4$ are independently CR$_1$ or N, and, R$_1$ is selected from the group consisting of hydrogen, a C$_6$-C$_{60}$ aryl group, a fluorenyl group, C$_2$-C$_{60}$ heterocyclic group containing at least one heteroatom selected from the group consisting of O, N, S, Si, and P.

3. The compound as claimed in claim 1, being any one of the compounds below:

P-1

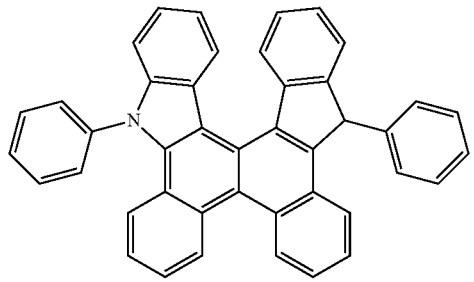

P-2

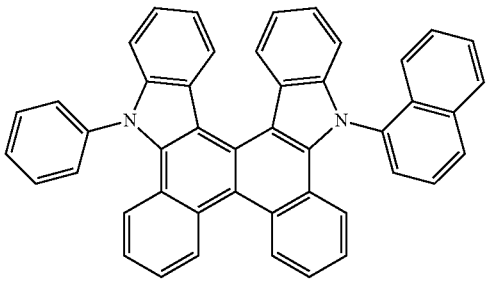

P-3

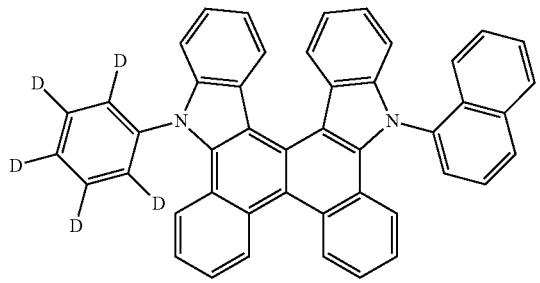

P-4

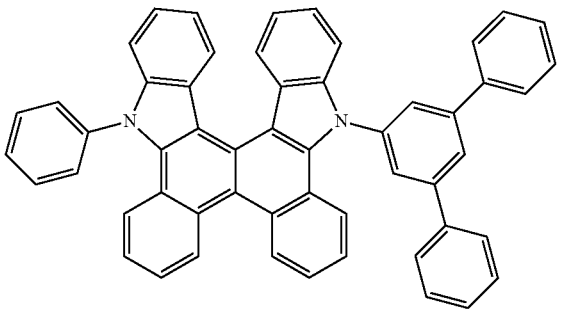

P-5

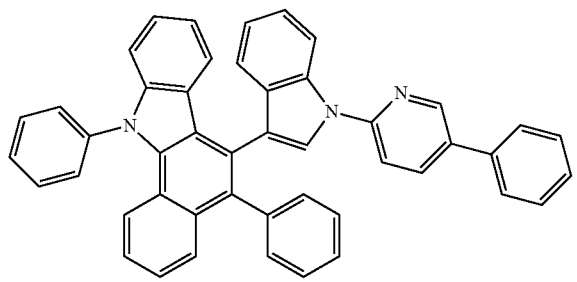

P-6

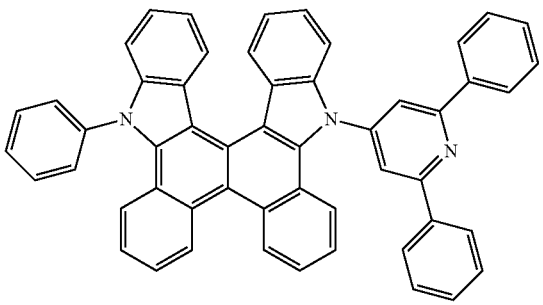

P-7

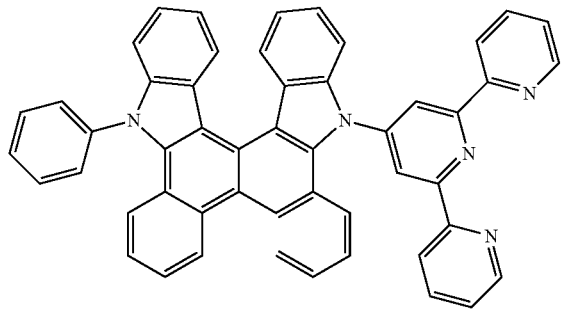

P-8

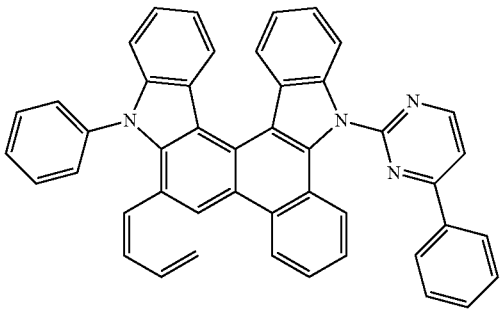

-continued
P-9
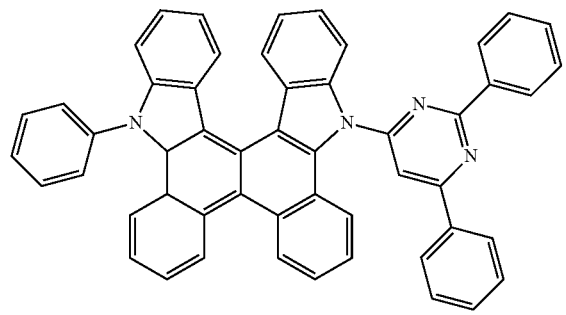
P-10
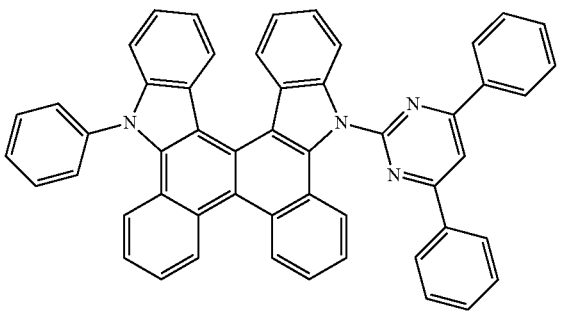
P-11
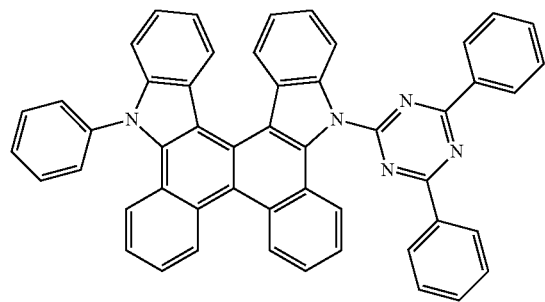
P-12
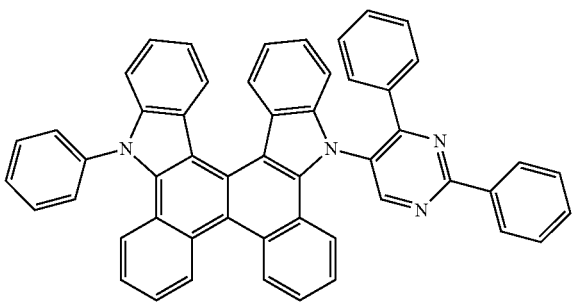
P-13
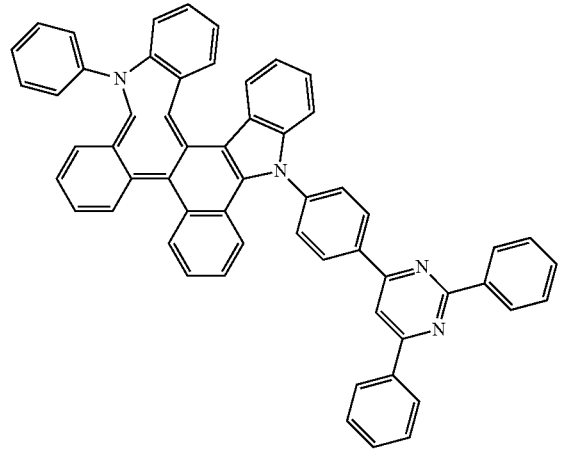
P-14
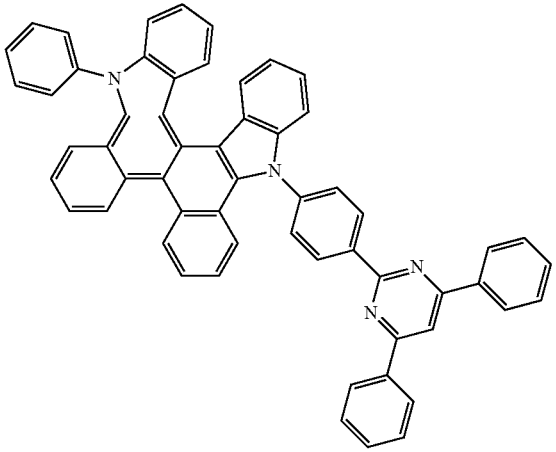
P-15
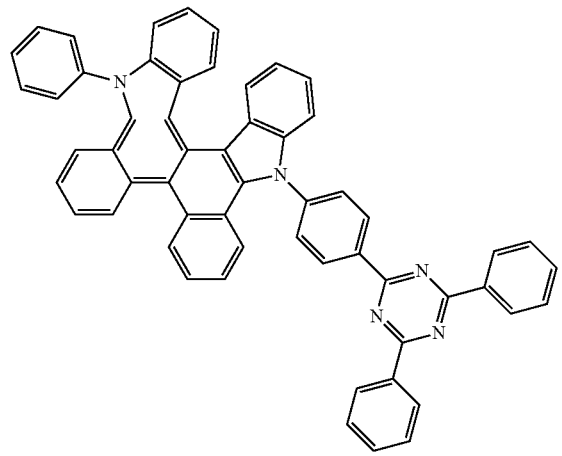
P-16
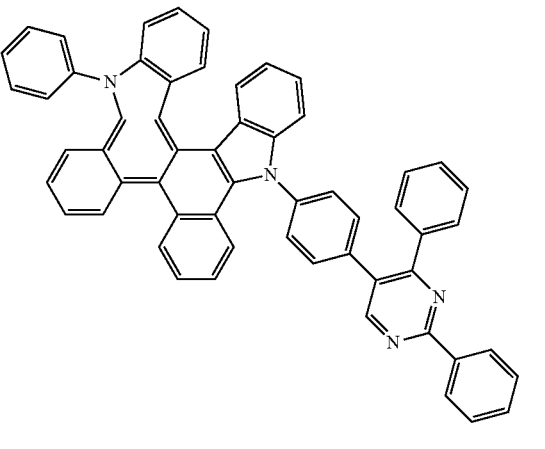

-continued
P-17
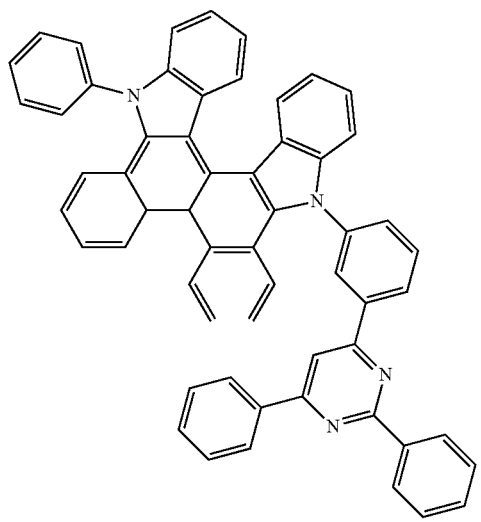
P-18
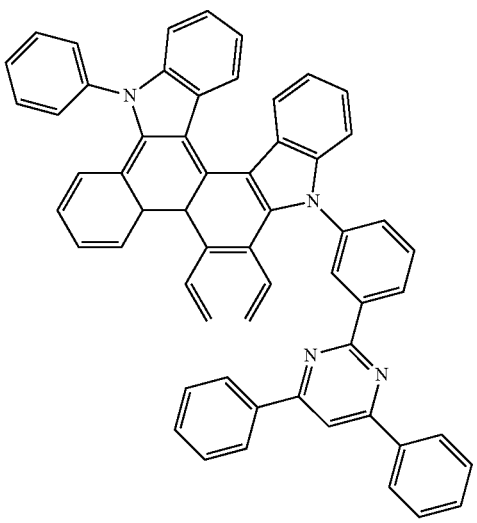
P-19
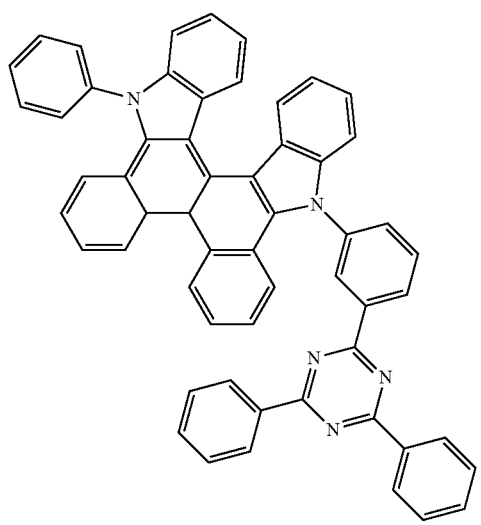
P-20
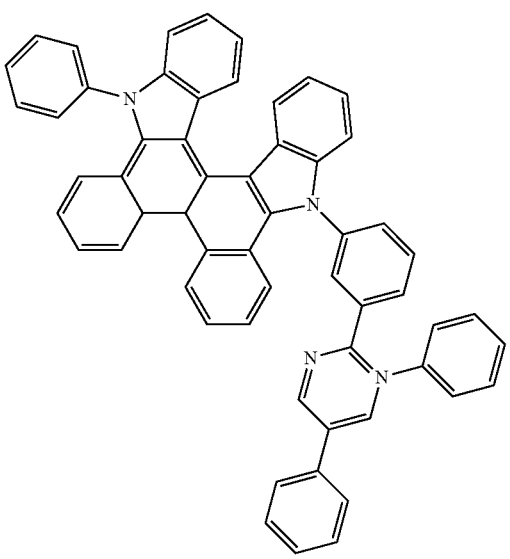
P-21
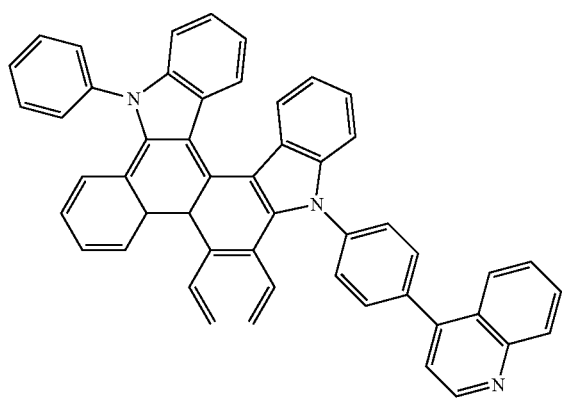
P-22
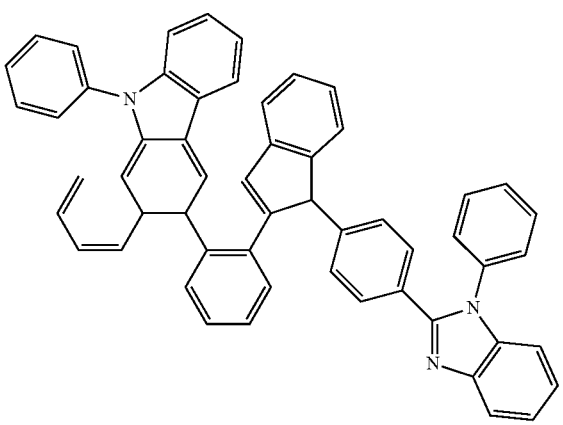

-continued
P-23
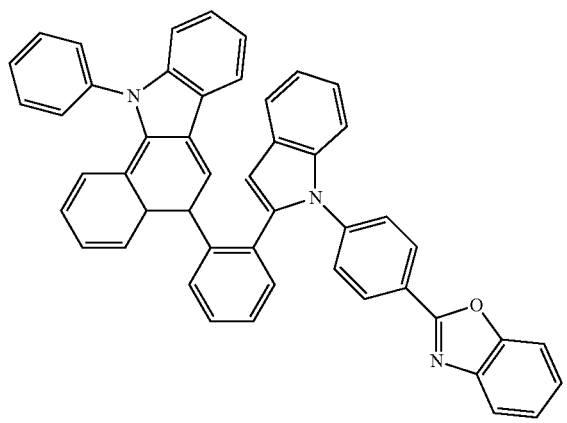
P-24
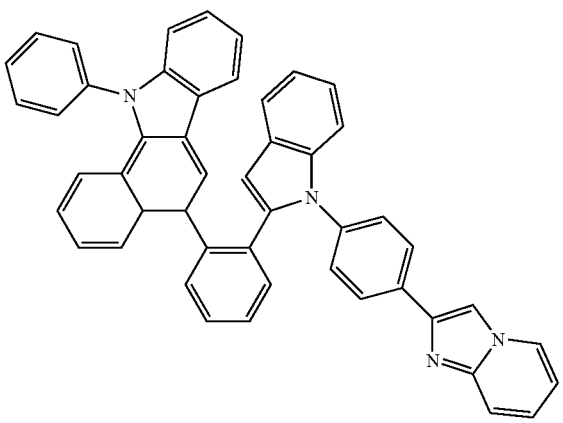
P-25
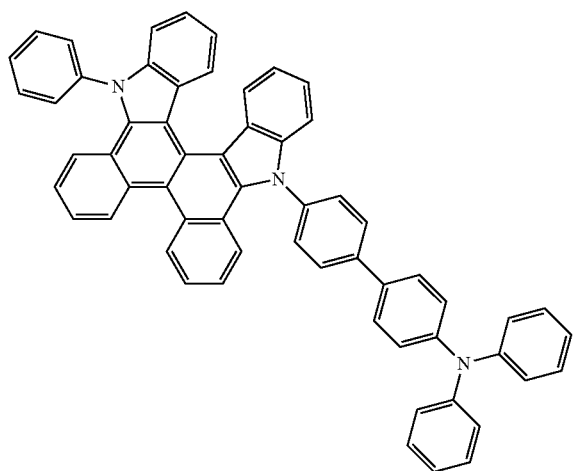
P-26
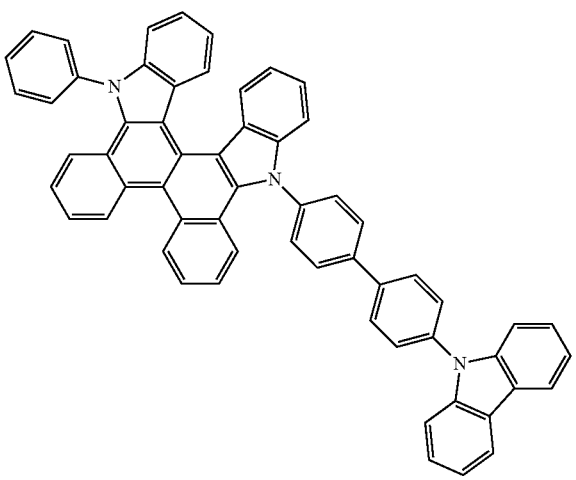
P-27
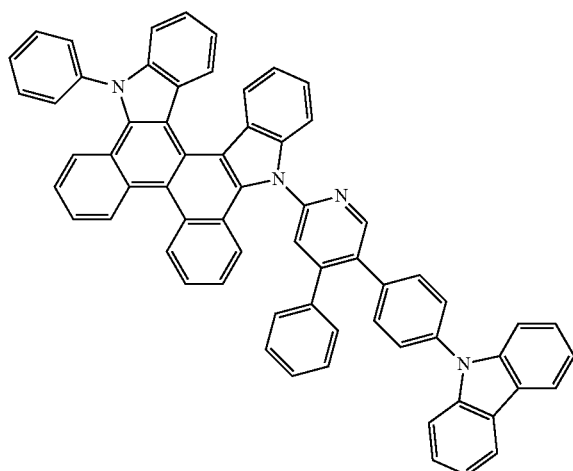
P-28
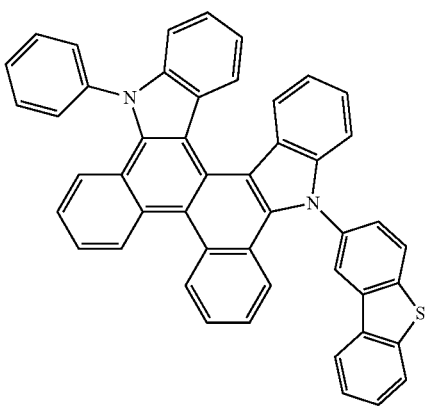

-continued
P-29
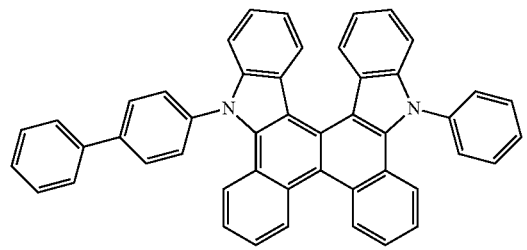
P-30
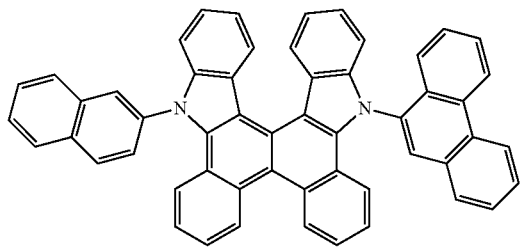
P-31
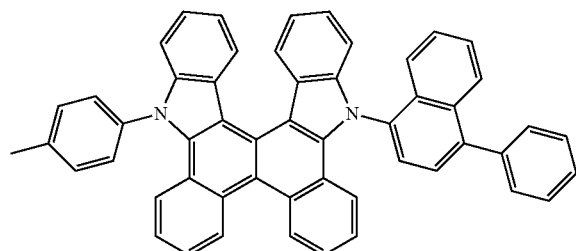
P-32
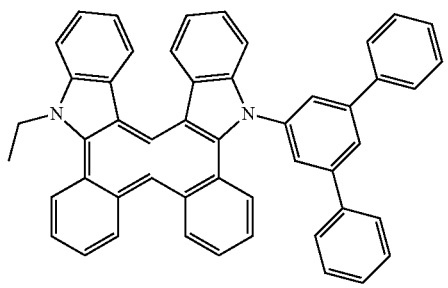
P-33
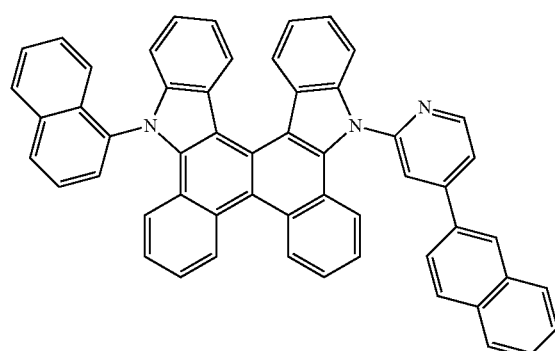
P-34
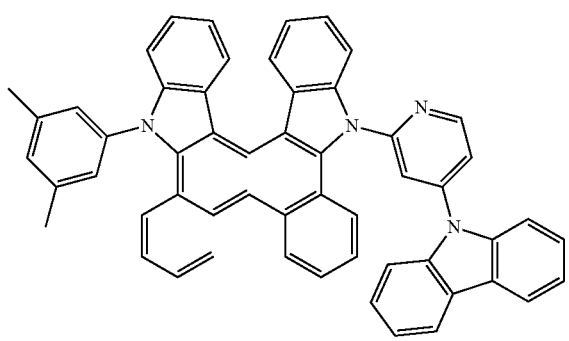
P-35
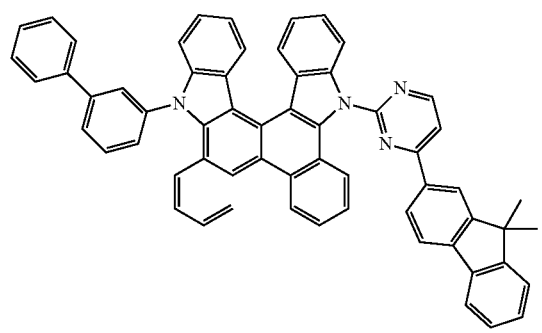
P-36
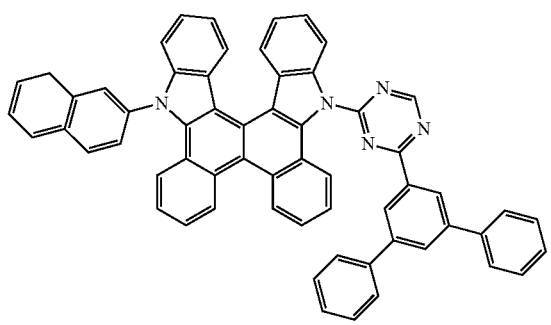
P-37
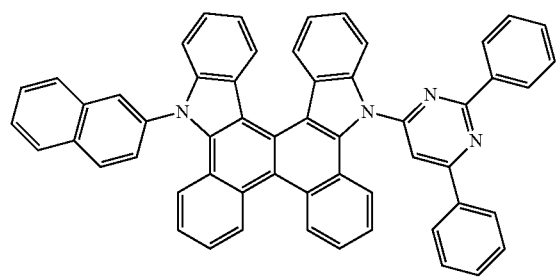
P-38
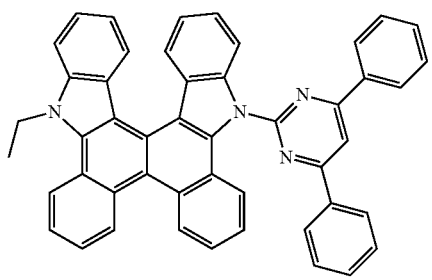

-continued
P-39
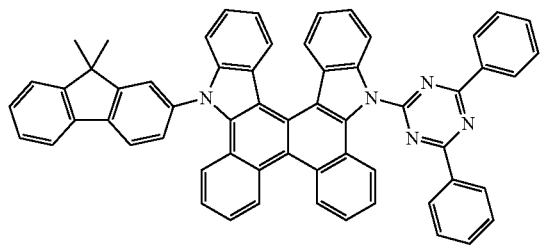
P-40
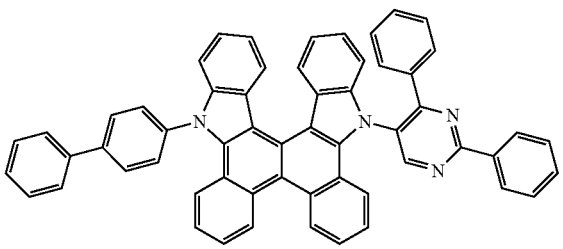
P-41
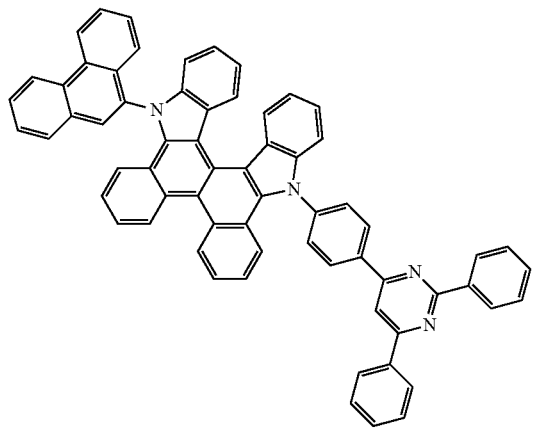
P-42
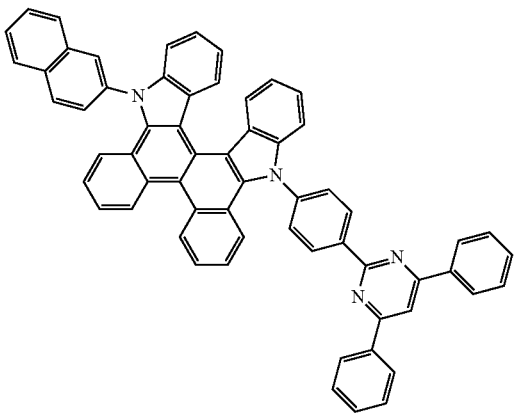
P-43
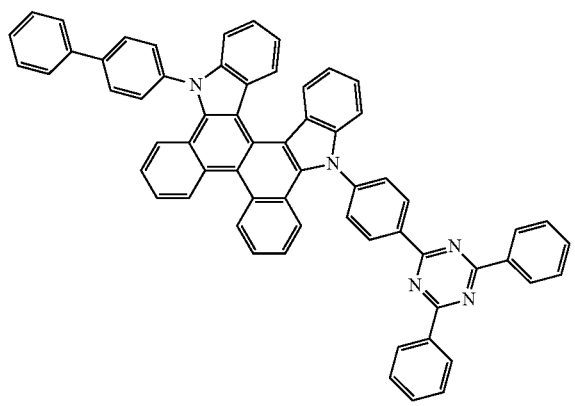
P-44
P-45
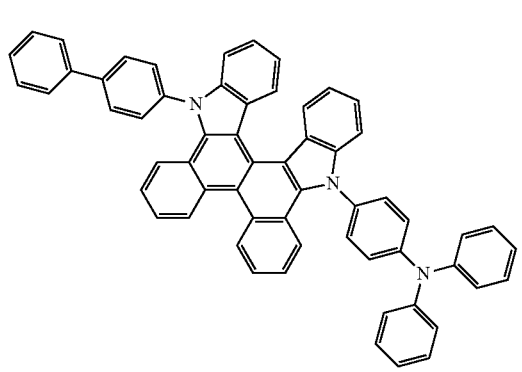
P-46
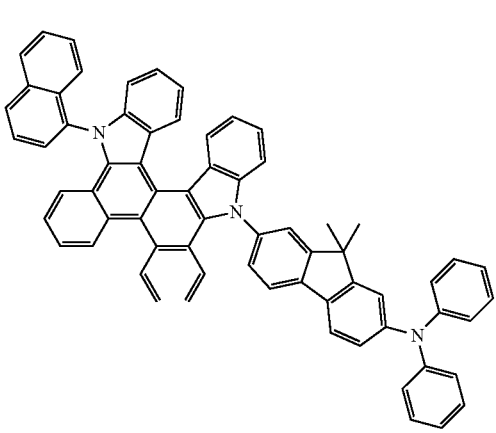

-continued
P-47
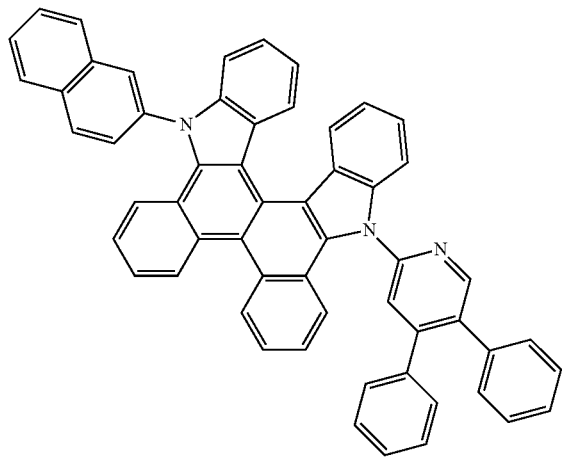
P-48
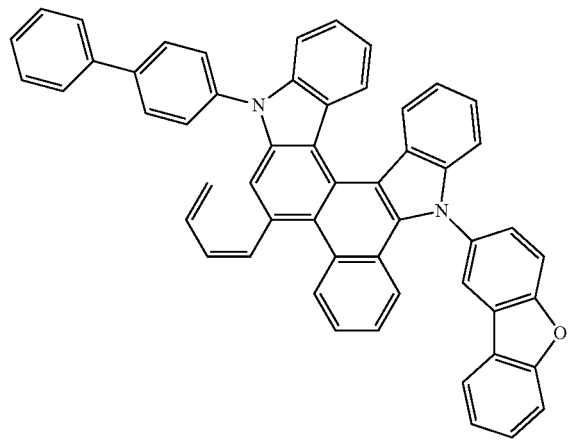
P-49
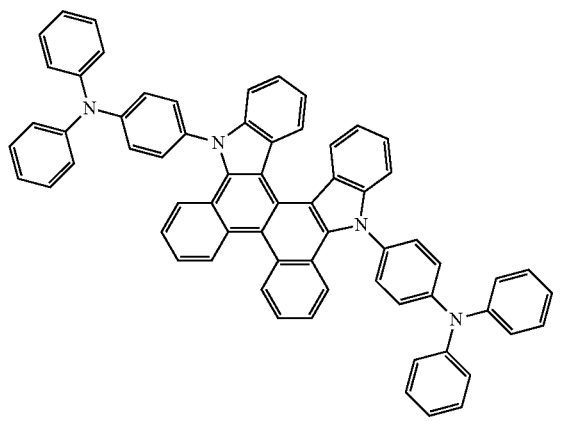
P-50
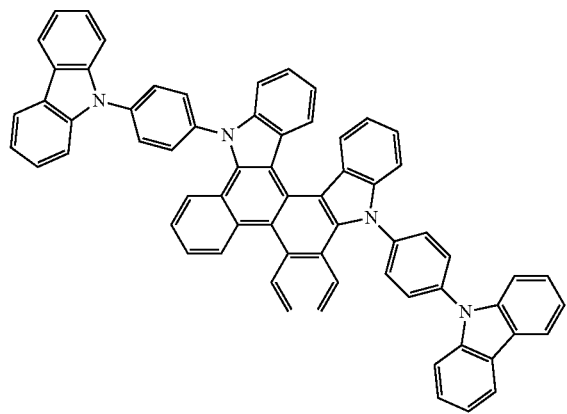
P-51
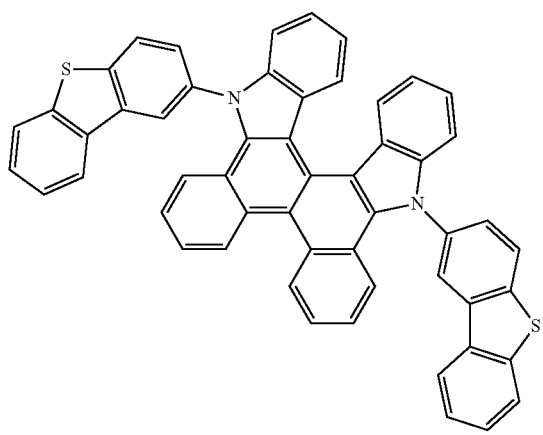

P-52
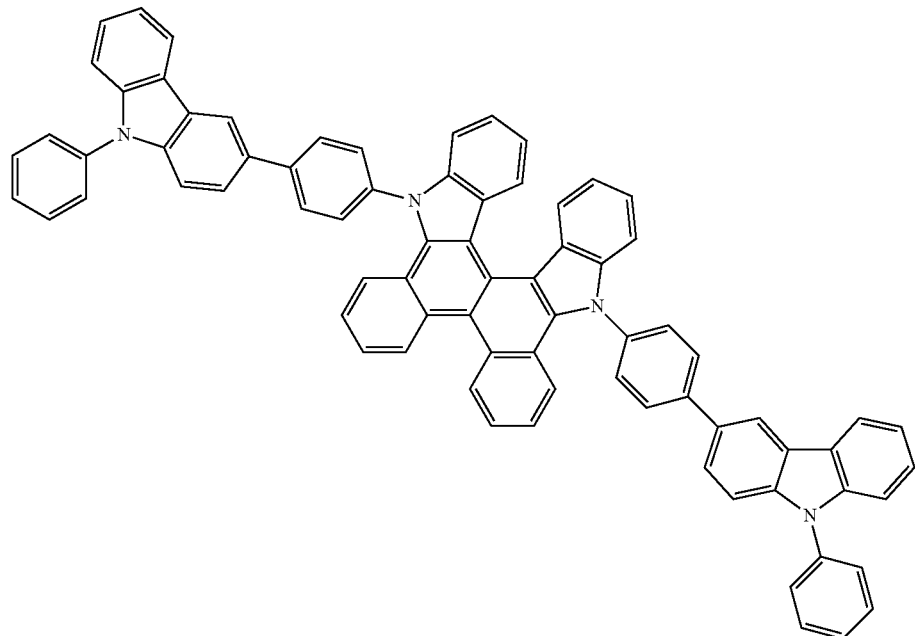
P-53
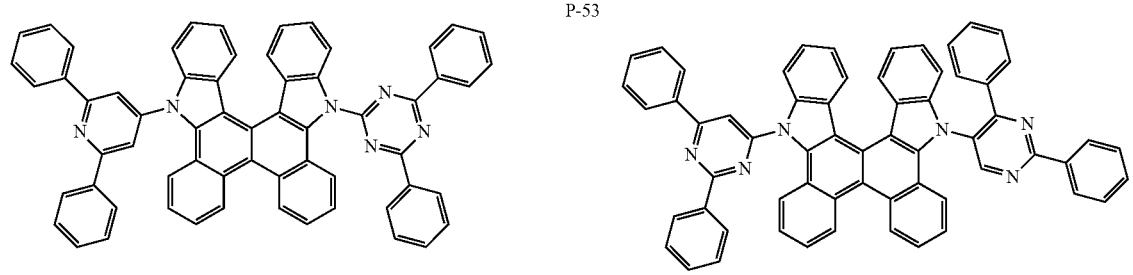
P-54
P-55
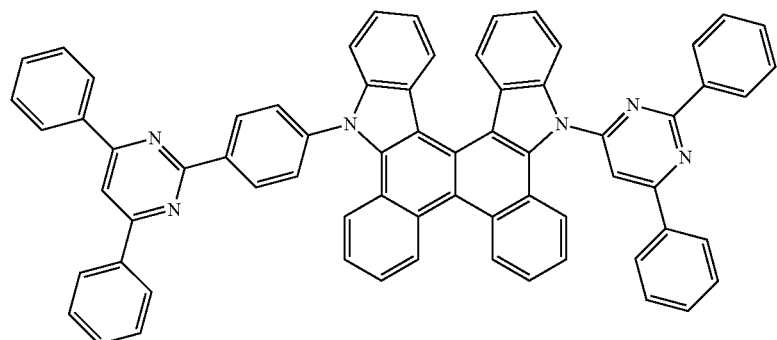
P-56
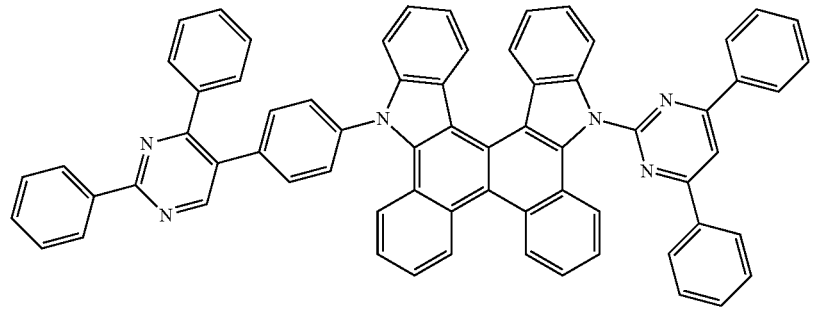

-continued
P-57
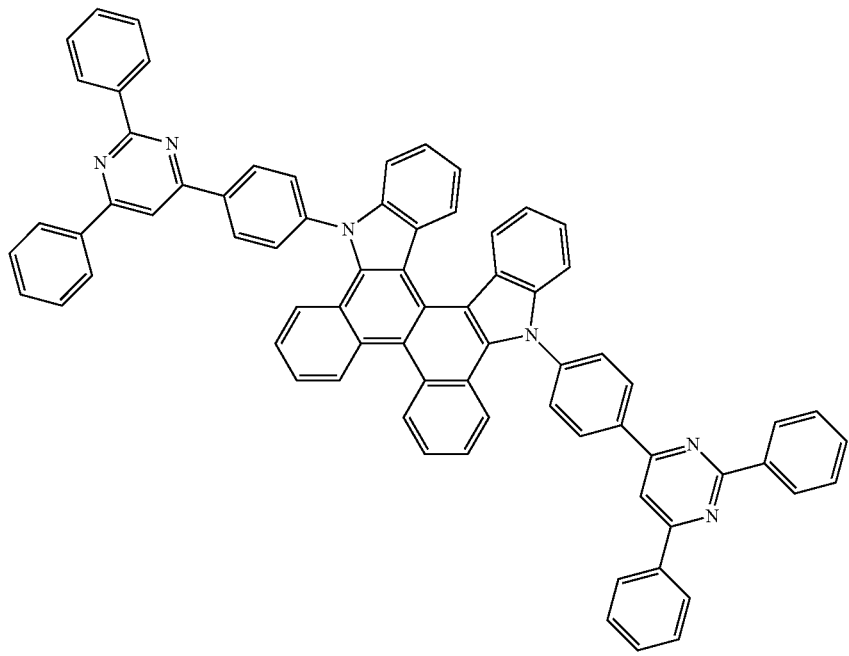
P-58
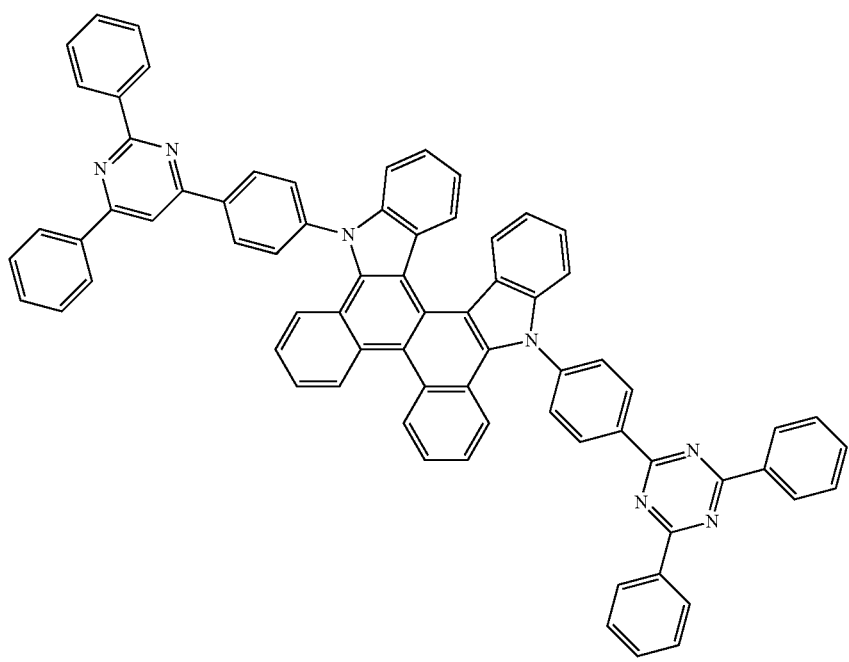

-continued
P-59
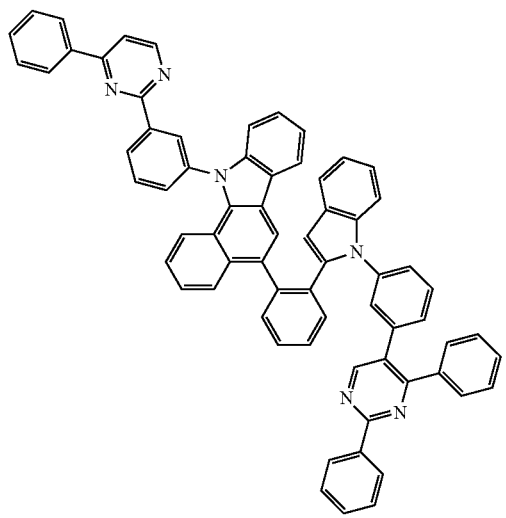
P-60
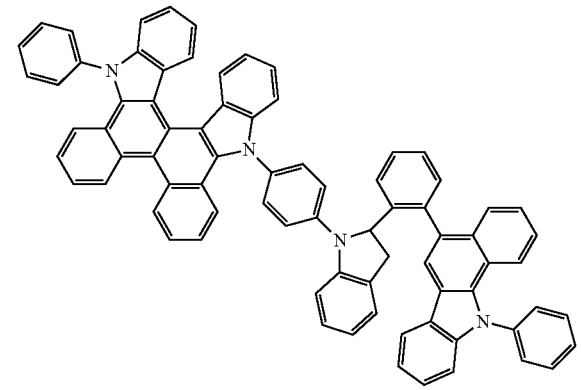
P-61
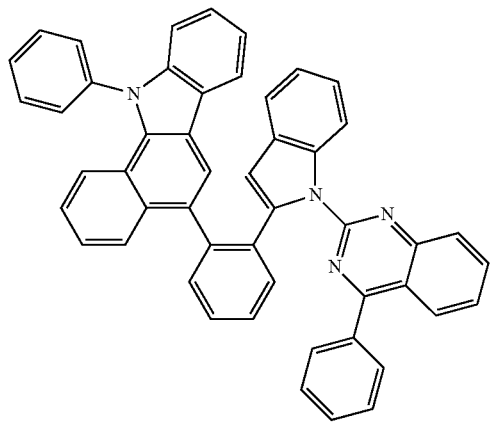
P-62
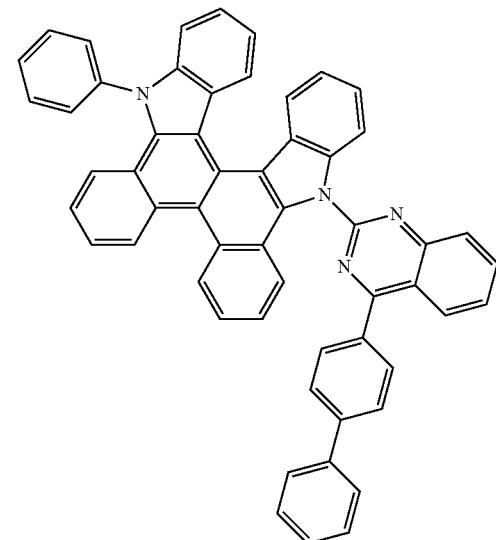
P-63
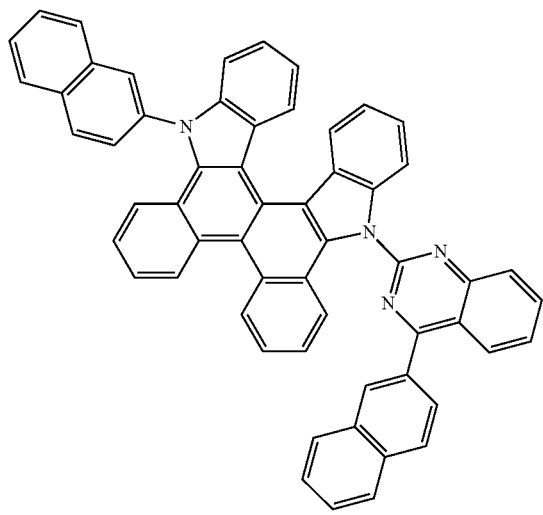
P-64
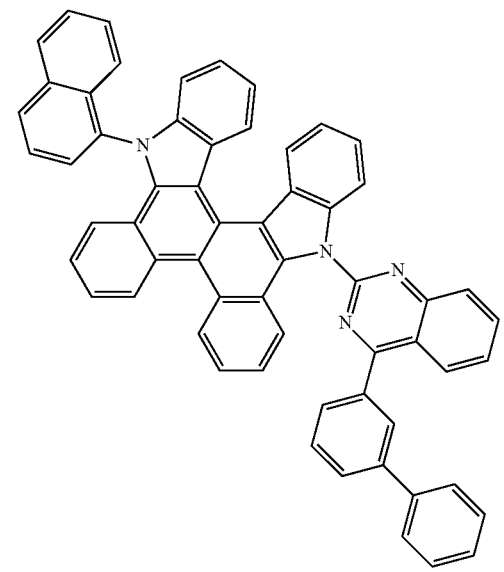

-continued
P-65
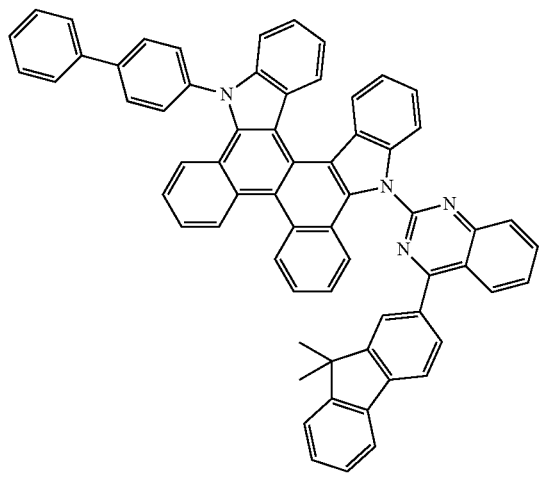
P-66
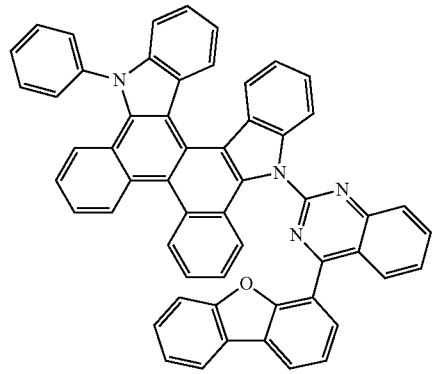
P-67
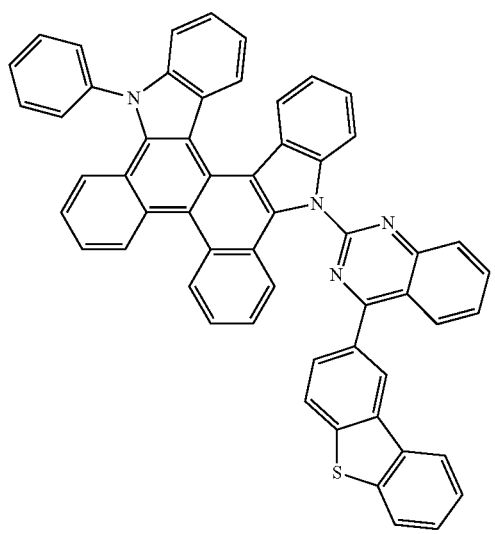
P-68
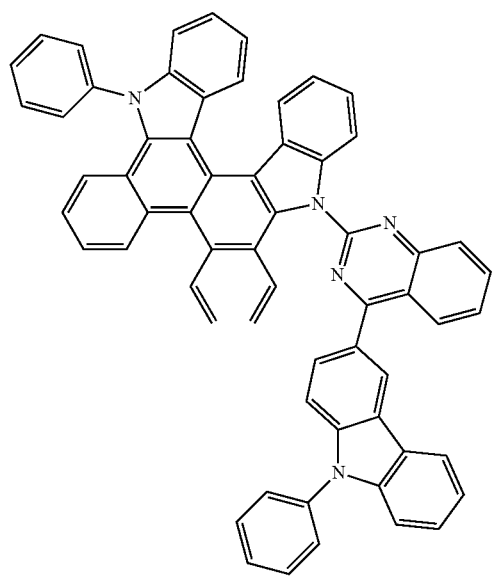
P-69
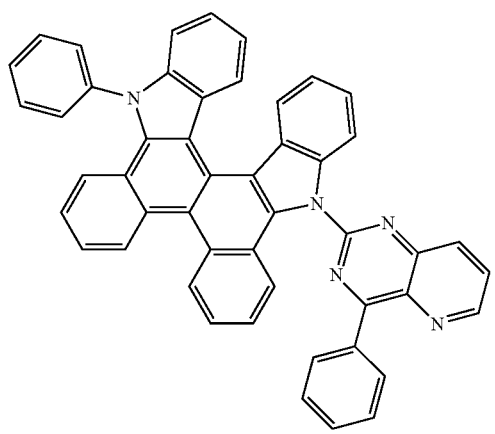
P-70
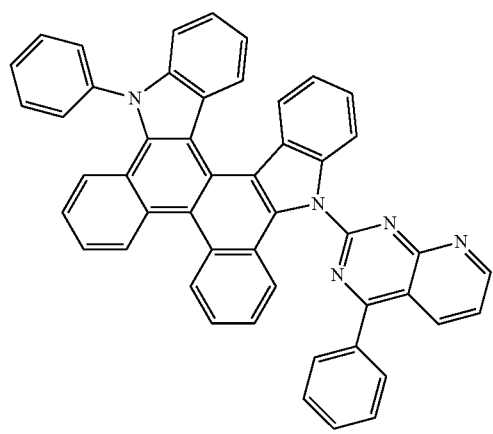

-continued
P-71
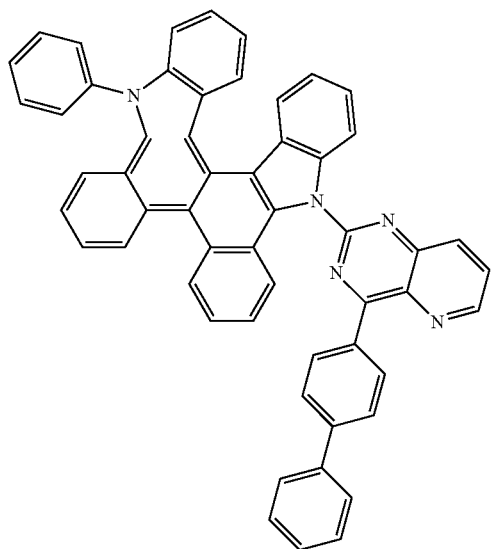
P-72
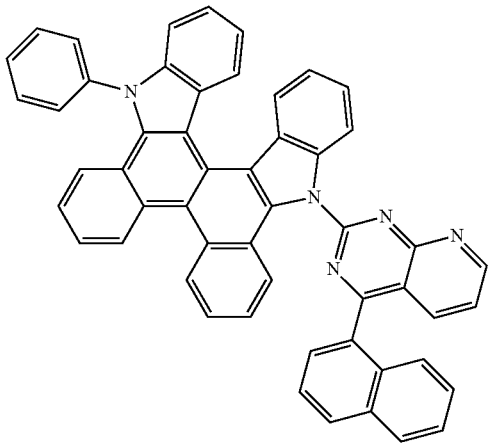
P-73
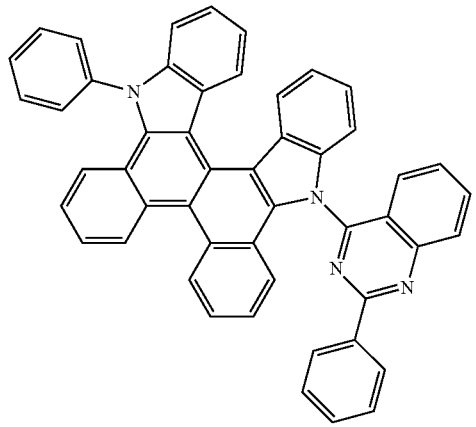
P-74
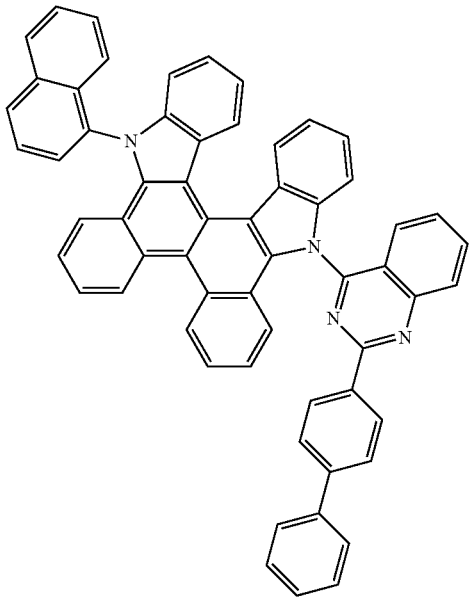

-continued
P-75
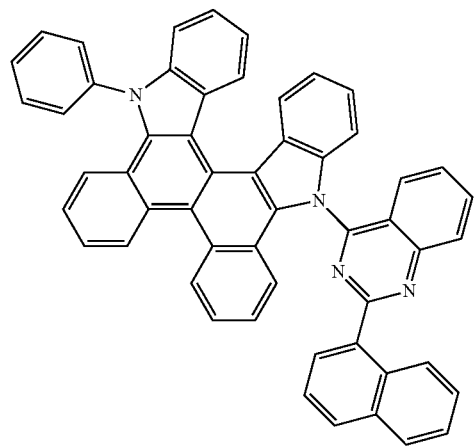
P-76
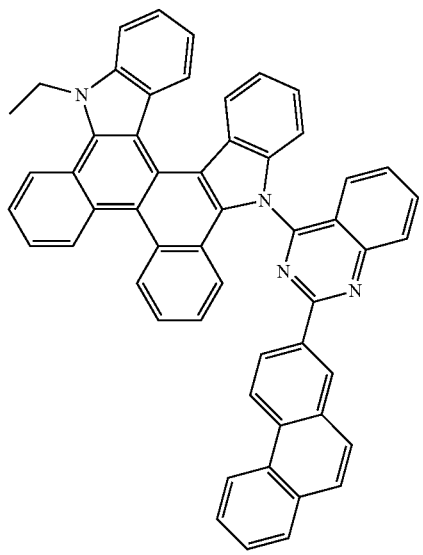
P-77
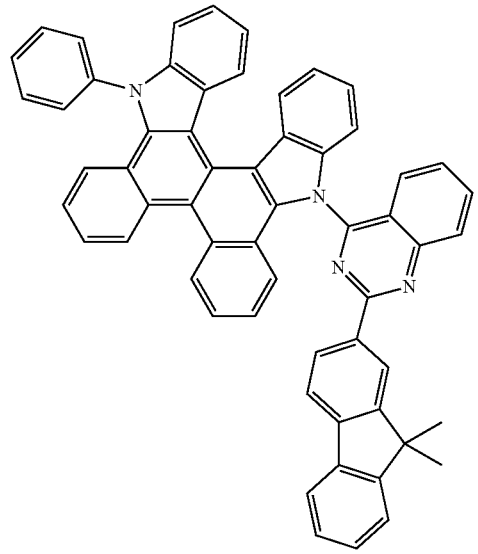
P-78
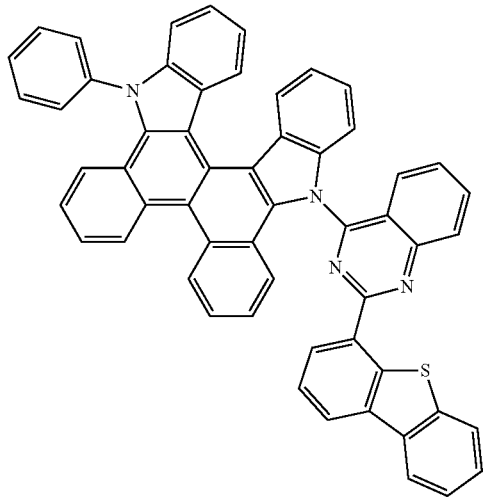

-continued
P-79
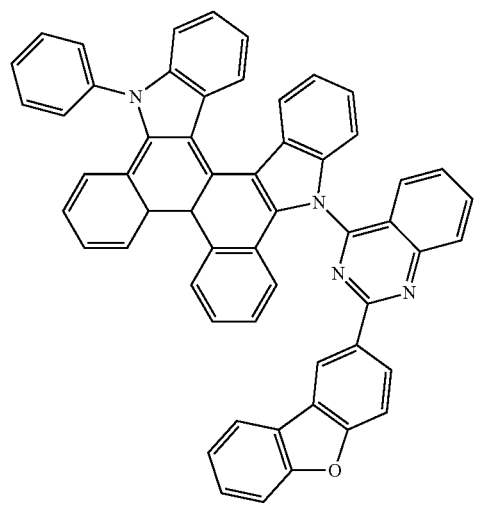
P-80
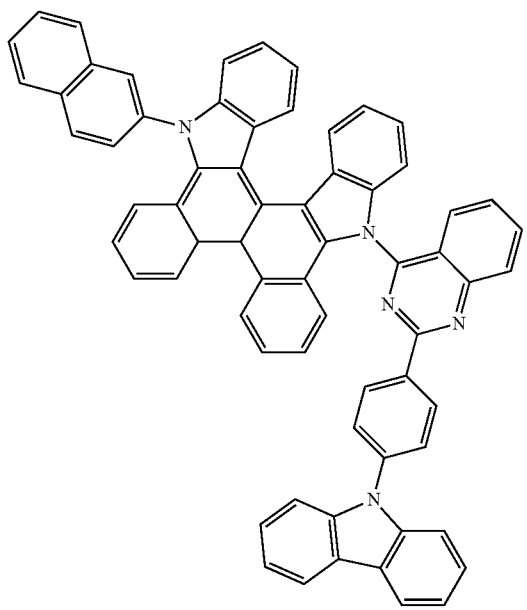
P-81
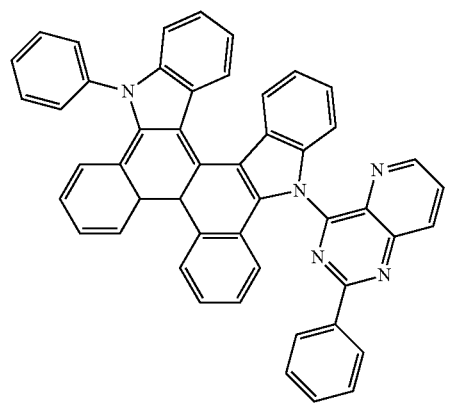
P-82
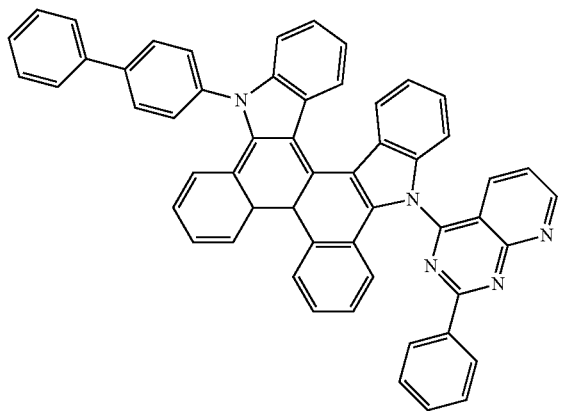
P-83
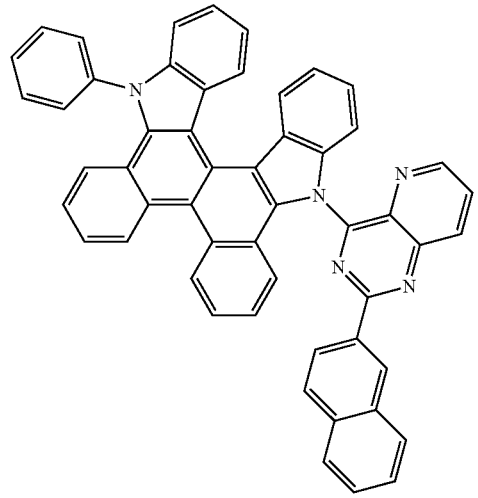
P-84
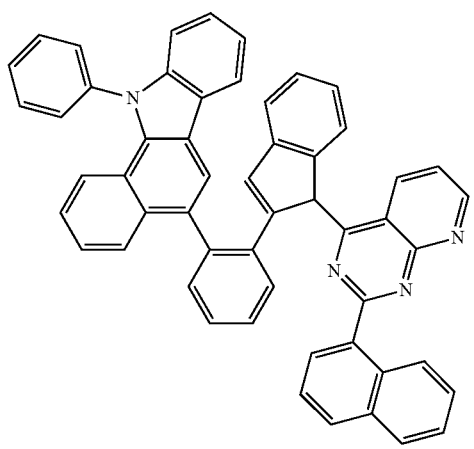

-continued
P-85
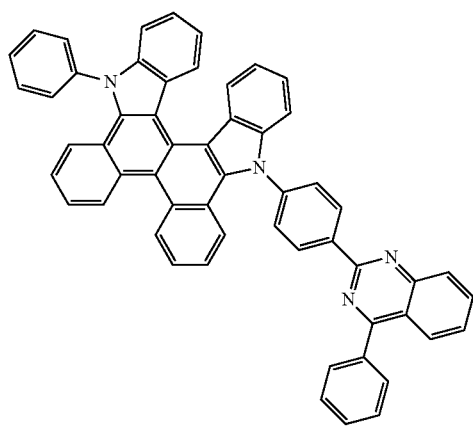
P-86
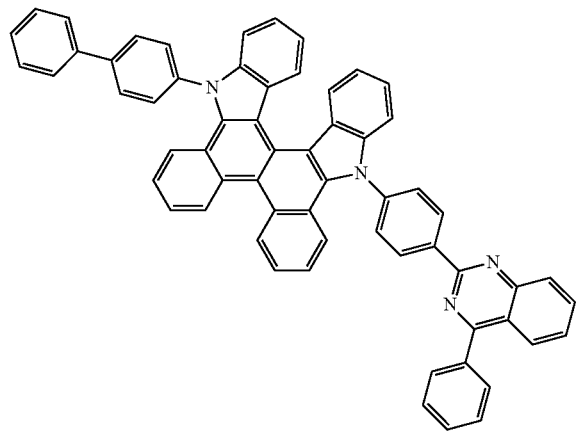
P-87
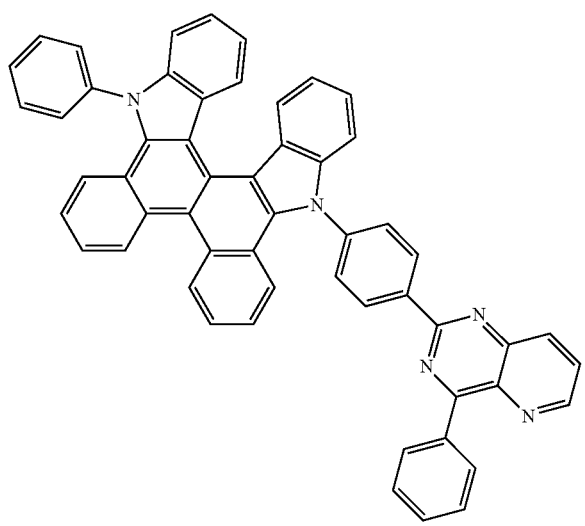
P-88
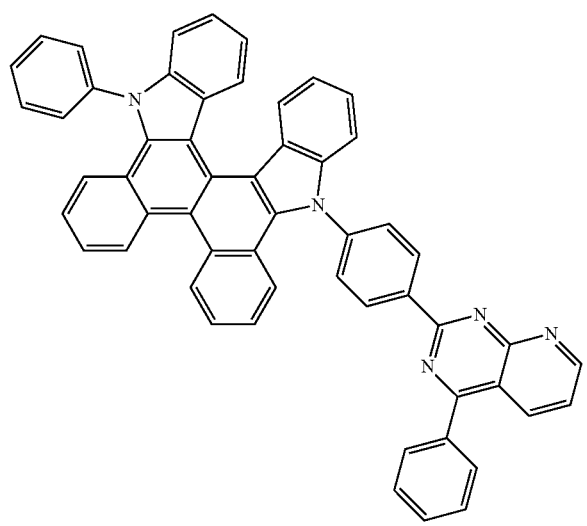
P-89
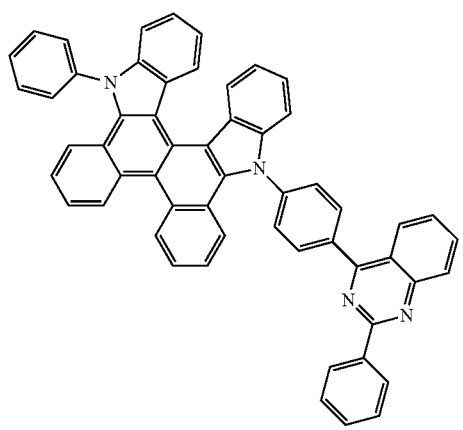
P-90
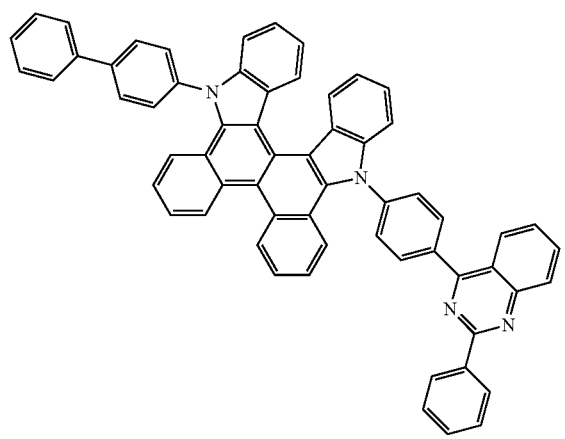

P-91

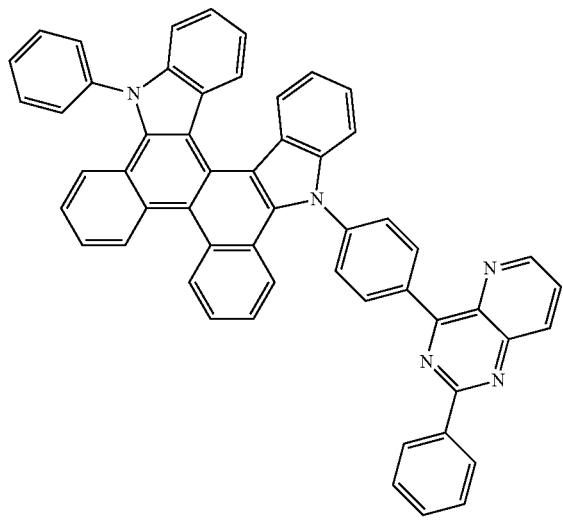

P-92

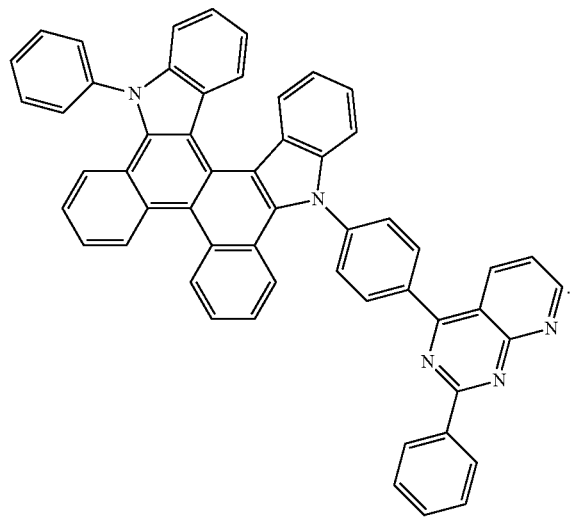

4. An organic electric element comprising a first electrode, a second electrode, and an organic material layer disposed between the first electrode and the second electrode, wherein the organic material layer comprises the compound of claim 1.

5. The organic electric element as claimed in claim 4, wherein the organic material layer is formed by a soluble process.

6. The organic electric element as claimed in claim 4, wherein the organic material layer comprises at least one of a light emitting layer, a hole injection layer, a hole transport layer, an emission-auxiliary layer, an electron injection layer and an electron transport layer.

7. The organic electric element as claimed in claim 6, wherein the light emitting layer comprises the compound.

8. An electronic device comprising a display device, which comprises the organic electric element as claimed in claim 4, and a control unit for driving the display device.

9. The electronic device as claimed in claim 8, wherein the organic electric element comprises at least one of an organic light emitting diode, an organic solar cell, an organic photo conductor, an organic transistor, and an element for monochromatic or white illumination.

* * * * *